US008944069B2

(12) United States Patent
Miller et al.

(10) Patent No.: US 8,944,069 B2
(45) Date of Patent: Feb. 3, 2015

(54) ASSEMBLIES FOR COUPLING INTRAOSSEOUS (IO) DEVICES TO POWERED DRIVERS

(75) Inventors: Larry J. Miller, Spring Branch, TX (US); Eric W. Eisbrenner, San Antonio, TX (US)

(73) Assignee: Vidacare Corporation, Shavano Park, TX (US)

( * ) Notice: Subject to any disclaimer, the term of this patent is extended or adjusted under 35 U.S.C. 154(b) by 883 days.

(21) Appl. No.: 12/407,651

(22) Filed: Mar. 19, 2009

(65) Prior Publication Data

US 2009/0194446 A1    Aug. 6, 2009

Related U.S. Application Data

(63) Continuation-in-part of application No. 11/853,701, filed on Sep. 11, 2007, now Pat. No. 8,656,929.

(60) Provisional application No. 60/825,325, filed on Sep. 12, 2006, provisional application No. 60/910,122, filed on Apr. 4, 2007.

(51) Int. Cl.
*A61B 19/10*    (2006.01)
*A61B 19/02*    (2006.01)
(Continued)

(52) U.S. Cl.
CPC ....... *A61B 19/026* (2013.01); *A61B 2017/0649* (2013.01); *A61B 2017/0046* (2013.01);
(Continued)

(58) Field of Classification Search
CPC ................ A61B 19/081; A61B 19/10; A61B 2019/081; A61B 2019/10
USPC .................... 128/849–855; 606/79–80, 86 R; 600/125, 568; 206/363–370; 383/33–34.1
See application file for complete search history.

(56) References Cited

U.S. PATENT DOCUMENTS

| 1,539,637 A | 5/1925 | Bronner .......................... 443/81 |
| 2,317,648 A | 4/1943 | Siqveland ......................... 32/26 |

(Continued)

FOREIGN PATENT DOCUMENTS

| CA | 2138842 | 6/1996 |
| CA | 2 454 600 | 1/2004 |

(Continued)

OTHER PUBLICATIONS

International PCT Search Report PCT/US03/17167, 8 pages, Mailed Sep. 16, 2003.

(Continued)

*Primary Examiner* — Patricia Bianco
*Assistant Examiner* — Kari Petrik
(74) *Attorney, Agent, or Firm* — Fulbright & Jaworski LLP

(57) ABSTRACT

Medical devices, medical procedure trays, kits and related methods are provided for use to perform medical procedures that require access to the interior of a bone. The devices, trays and methods allow multiple use of non-sterile medical devices with sterile medical devices for performing medical procedures requiring sterile conditions. A coupler assembly, capable of releasably attaching to a non-sterile medical device at one end and releasably attaching to one or more sterile medical devices at another end, and further comprising a containment bag which allows maintaining sterility of a non-sterile medical device which may be used in conjunction with sterile medical devices and procedures. The devices, trays, kits and methods enable the performance of multiple medical procedures with a single insertion into bone. For example, a vertebral procedure such as a vertebroplasty may be performed along with biopsy and/or bone marrow aspiration procedures, thereby reducing patient trauma and costs.

4 Claims, 19 Drawing Sheets

(51) Int. Cl.
*A61B 19/08* (2006.01)
*A61B 17/34* (2006.01)
*A61B 10/02* (2006.01)
  A61B 17/064 (2006.01)
  A61B 17/00 (2006.01)
  A61B 19/00 (2006.01)

(52) U.S. Cl.
CPC ........... *A61B19/0271* (2013.01); *A61B 19/081* (2013.01); *A61B 19/38* (2013.01); *A61B 2019/462* (2013.01); *A61B 19/08* (2013.01); *A61B 17/3472* (2013.01); *A61B 10/025* (2013.01); *A61B 2017/00734* (2013.01); *A61B 19/10* (2013.01); *A61B 2010/0258* (2013.01)
USPC ............. 128/852; 128/853; 600/568; 606/80; 606/86 R

(56) References Cited

U.S. PATENT DOCUMENTS

| | | | |
|---|---|---|---|
| 2,419,045 A | 4/1947 | Whittaker | 128/305 |
| 2,773,501 A | 12/1956 | Young | 128/221 |
| 2,860,635 A | 11/1958 | Wilburn | 604/190 |
| 3,104,448 A | 9/1963 | Morrow et al. | |
| 3,120,845 A | 2/1964 | Horner | 128/310 |
| 3,173,417 A | 3/1965 | Horner | 128/305 |
| 3,175,554 A | 3/1965 | Stewart | 128/2 |
| 3,507,276 A | 4/1970 | Burgess et al. | 128/173 |
| 3,543,966 A | 12/1970 | Ryan et al. | 222/94 |
| 3,750,667 A | 8/1973 | Pshenichny et al. | 604/117 |
| 3,815,605 A | 6/1974 | Schmidt et al. | 128/305 |
| 3,835,860 A | 9/1974 | Garretson | 128/310 |
| 3,893,445 A | 7/1975 | Hofsess | 128/2 B |
| 3,991,765 A | 11/1976 | Cohen | 128/305 |
| 4,021,920 A | 5/1977 | Kirschner et al. | 32/28 |
| 4,099,518 A | 7/1978 | Baylis et al. | 600/567 |
| 4,124,026 A | 11/1978 | Berner et al. | 606/104 |
| 4,142,517 A | 3/1979 | Stavropoulos et al. | 128/2 B |
| 4,170,993 A | 10/1979 | Alvarez | 128/214 R |
| 4,185,619 A | 1/1980 | Reiss | 128/1.1 |
| 4,194,505 A | 3/1980 | Schmitz | 128/218 |
| 4,258,722 A | 3/1981 | Sessions et al. | 128/753 |
| 4,262,676 A | 4/1981 | Jamshidi | 128/753 |
| 4,266,555 A | 5/1981 | Jamshidi | 600/566 |
| 4,306,570 A | 12/1981 | Matthews | 128/754 |
| 4,333,459 A | 6/1982 | Becker | 128/218 |
| 4,359,052 A | 11/1982 | Staub | 606/30 |
| 4,381,777 A | 5/1983 | Garnier | 604/188 |
| 4,399,723 A | 8/1983 | Marleau | 81/437 |
| 4,441,563 A | 4/1984 | Walton, II | 173/163 |
| 4,469,109 A | 9/1984 | Mehl | 128/753 |
| 4,484,577 A | 11/1984 | Sackner et al. | 128/203.28 |
| 4,487,209 A | 12/1984 | Mehl | 600/567 |
| 4,543,966 A | 10/1985 | Islam et al. | 128/754 |
| 4,553,539 A | 11/1985 | Morris | 128/132 D |
| 4,578,064 A | 3/1986 | Sarnoff et al. | 604/191 |
| 4,605,011 A | 8/1986 | Naslund | 128/752 |
| 4,620,539 A | 11/1986 | Andrews et al. | 128/303 |
| 4,646,731 A | 3/1987 | Brower | 128/136 |
| 4,654,492 A | 3/1987 | Koerner et al. | 200/153 P |
| 4,655,226 A | 4/1987 | Lee | 128/754 |
| 4,659,329 A | 4/1987 | Annis | 604/180 |
| 4,692,073 A | 9/1987 | Martindell | |
| 4,711,636 A | 12/1987 | Bierman | 604/180 |
| 4,713,061 A | 12/1987 | Tarello et al. | 604/200 |
| 4,716,901 A | 1/1988 | Jackson et al. | 128/343 |
| 4,723,945 A | 2/1988 | Theiling | 604/232 |
| 4,758,225 A | 7/1988 | Cox et al. | 604/126 |
| 4,762,118 A | 8/1988 | Lia et al. | 600/141 |
| 4,772,261 A | 9/1988 | Von Hoff et al. | 604/51 |
| 4,787,893 A | 11/1988 | Villette | 604/188 |
| 4,793,363 A | 12/1988 | Ausherman et al. | 128/754 |
| 4,838,282 A | 6/1989 | Strasser et al. | 600/567 |
| 4,867,158 A | 9/1989 | Sugg | 128/305 |
| 4,919,146 A | 4/1990 | Rhinehart et al. | 128/752 |
| 4,921,013 A | 5/1990 | Spalink et al. | 137/614.05 |
| 4,922,602 A | 5/1990 | Mehl | 29/460 |
| 4,935,010 A | 6/1990 | Cox et al. | 604/122 |
| 4,940,459 A | 7/1990 | Noce | 604/98 |
| 4,944,677 A | 7/1990 | Alexandre | 433/165 |
| 4,969,870 A | 11/1990 | Kramer et al. | 604/51 |
| 4,986,279 A | 1/1991 | O'Neill | 128/754 |
| 5,002,546 A | 3/1991 | Romano | 606/80 |
| 5,025,797 A | 6/1991 | Baran | 128/754 |
| 5,036,860 A | 8/1991 | Leigh et al. | 128/754 |
| 5,057,085 A | 10/1991 | Kopans | 604/173 |
| 5,074,311 A | 12/1991 | Hasson | 128/754 |
| 5,116,324 A | 5/1992 | Brierley et al. | 604/180 |
| 5,120,312 A | 6/1992 | Wigness et al. | 604/175 |
| 5,122,114 A | 6/1992 | Miller et al. | 604/49 |
| 5,133,359 A | 7/1992 | Kedem | 128/754 |
| 5,137,518 A | 8/1992 | Mersch | 604/168 |
| 5,139,500 A | 8/1992 | Schwartz | 606/96 |
| RE34,056 E | 9/1992 | Lindgren et al. | 128/754 |
| 5,145,369 A | 9/1992 | Lustig et al. | 433/118 |
| 5,172,701 A | 12/1992 | Leigh et al. | 128/753 |
| 5,172,702 A | 12/1992 | Leigh et al. | 128/754 |
| 5,176,415 A | 1/1993 | Choksi | 285/331 |
| 5,176,643 A | 1/1993 | Kramer et al. | 604/135 |
| 5,195,985 A | 3/1993 | Hall | 604/195 |
| 5,203,056 A | 4/1993 | Funk et al. | 24/543 |
| 5,207,697 A | 5/1993 | Carusillo et al. | 606/167 |
| 5,249,583 A | 10/1993 | Mallaby | 128/754 |
| 5,257,632 A | 11/1993 | Turkel et al. | 128/754 |
| 5,261,877 A | 11/1993 | Fine et al. | 604/540 |
| 5,269,785 A | 12/1993 | Bonutti | 606/80 |
| 5,279,306 A | 1/1994 | Mehl | 128/753 |
| 5,312,351 A | 5/1994 | Gerrone | 604/117 |
| 5,312,364 A | 5/1994 | Jacobs | 604/180 |
| 5,312,408 A | 5/1994 | Brown | 606/80 |
| 5,324,300 A | 6/1994 | Elias et al. | 606/180 |
| 5,332,398 A | 7/1994 | Miller et al. | 604/175 |
| 5,333,790 A | 8/1994 | Christopher | 239/391 |
| 5,339,831 A * | 8/1994 | Thompson | 128/852 |
| 5,341,816 A | 8/1994 | Allen | 600/567 |
| 5,341,823 A | 8/1994 | Manosalva et al. | 128/898 |
| 5,348,022 A | 9/1994 | Leigh et al. | 128/753 |
| 5,357,974 A | 10/1994 | Baldridge | 128/754 |
| 5,368,046 A | 11/1994 | Scarfone et al. | 128/754 |
| 5,372,583 A | 12/1994 | Roberts et al. | 604/51 |
| 5,383,859 A | 1/1995 | Sewell, Jr. | 604/164 |
| 5,385,151 A | 1/1995 | Scarfone et al. | 600/567 |
| 5,385,553 A | 1/1995 | Hart et al. | 604/167 |
| 5,400,798 A | 3/1995 | Baran | 128/754 |
| 5,405,348 A | 4/1995 | Anspach et al. | 606/80 |
| 5,405,362 A | 4/1995 | Kramer et al. | 607/5 |
| 5,423,824 A | 6/1995 | Akerfeldt et al. | 606/80 |
| 5,431,655 A | 7/1995 | Melker et al. | 606/79 |
| 5,451,210 A | 9/1995 | Kramer et al. | 604/137 |
| 5,484,442 A | 1/1996 | Melker et al. | 606/79 |
| D369,858 S | 5/1996 | Baker et al. | D24/112 |
| 5,514,097 A | 5/1996 | Knauer | 604/136 |
| 5,526,821 A | 6/1996 | Jamshidi | 128/753 |
| 5,529,580 A | 6/1996 | Kusunoki et al. | 606/170 |
| 5,549,565 A | 8/1996 | Ryan et al. | 604/167.03 |
| 5,554,154 A | 9/1996 | Rosenberg | 606/80 |
| 5,556,399 A | 9/1996 | Huebner et al. | 606/80 |
| 5,558,737 A | 9/1996 | Brown et al. | 156/172 |
| 5,571,133 A | 11/1996 | Yoon | 606/185 |
| 5,586,847 A | 12/1996 | Mattern, Jr. et al. | 408/239 A |
| 5,591,119 A * | 1/1997 | Adair | 600/112 |
| 5,591,188 A | 1/1997 | Waisman | 606/182 |
| 5,595,186 A | 1/1997 | Rubinstein et al. | 600/567 |
| 5,601,559 A | 2/1997 | Melker et al. | 606/79 |
| 5,632,747 A | 5/1997 | Scarborough et al. | 606/79 |
| 5,672,155 A | 9/1997 | Riley et al. | 604/154 |
| 5,713,368 A | 2/1998 | Leigh | 128/753 |
| 5,724,873 A | 3/1998 | Hillinger | 81/451 |
| 5,733,262 A | 3/1998 | Paul | 604/116 |
| 5,752,923 A | 5/1998 | Terwilliger | 600/562 |
| 5,762,639 A | 6/1998 | Gibbs | 604/272 |
| 5,766,221 A | 6/1998 | Benderev et al. | 606/232 |
| 5,769,086 A | 6/1998 | Ritchart et al. | 128/753 |

(56) References Cited

U.S. PATENT DOCUMENTS

| | | | |
|---|---|---|---|
| 5,779,708 A | 7/1998 | Wu | 606/80 |
| 5,800,389 A | 9/1998 | Burney et al. | 604/93 |
| 5,807,275 A | 9/1998 | Jamshidi | 600/567 |
| 5,807,277 A | 9/1998 | Swaim | 600/567 |
| 5,810,826 A | 9/1998 | Akerfeldt et al. | 606/80 |
| 5,817,052 A | 10/1998 | Johnson et al. | 604/51 |
| 5,823,970 A | 10/1998 | Terwilliger | 600/564 |
| D403,405 S | 12/1998 | Terwilliger | D24/130 |
| 5,858,005 A | 1/1999 | Kriesel | 604/180 |
| 5,868,711 A | 2/1999 | Kramer et al. | 604/136 |
| 5,868,750 A | 2/1999 | Schultz | 606/104 |
| 5,873,499 A | 2/1999 | Leschinsky et al. | 222/327 |
| 5,873,510 A | 2/1999 | Hirai et al. | 227/130 |
| 5,885,226 A | 3/1999 | Rubinstein et al. | 600/564 |
| 5,891,085 A | 4/1999 | Lilley et al. | 604/68 |
| 5,911,701 A | 6/1999 | Miller et al. | 604/22 |
| 5,911,708 A | 6/1999 | Teirstein | 604/183 |
| 5,916,229 A | 6/1999 | Evans | 606/171 |
| 5,919,172 A | 7/1999 | Golba, Jr. | 604/272 |
| 5,921,987 A | 7/1999 | Stone | 606/80 |
| 5,924,864 A | 7/1999 | Loge et al. | 433/118 |
| 5,927,976 A | 7/1999 | Wu | 433/82 |
| 5,928,238 A | 7/1999 | Scarborough et al. | 606/79 |
| 5,941,706 A | 8/1999 | Ura | 433/165 |
| 5,941,851 A | 8/1999 | Coffey et al. | 604/131 |
| 5,951,026 A | 9/1999 | Harman, Jr. et al. | 279/143 |
| 5,960,797 A | 10/1999 | Kramer et al. | 128/899 |
| 5,980,545 A | 11/1999 | Pacala et al. | 606/170 |
| 5,993,417 A | 11/1999 | Yerfino et al. | 604/110 |
| 5,993,454 A | 11/1999 | Longo | 606/80 |
| 6,007,496 A | 12/1999 | Brannon | 600/565 |
| 6,017,348 A | 1/2000 | Hart et al. | 606/79 |
| 6,018,094 A | 1/2000 | Fox | 623/11 |
| 6,022,324 A | 2/2000 | Skinner | 600/566 |
| 6,027,458 A | 2/2000 | Janssens | 600/567 |
| 6,033,369 A | 3/2000 | Goldenberg | 600/567 |
| 6,033,411 A | 3/2000 | Preissman | 606/99 |
| 6,042,585 A | 3/2000 | Norman | 606/104 |
| 6,063,037 A | 5/2000 | Mittermeier et al. | 600/567 |
| 6,071,284 A | 6/2000 | Fox | 606/80 |
| 6,080,115 A | 6/2000 | Rubinstein | 600/567 |
| 6,083,176 A | 7/2000 | Terwilliger | 600/562 |
| 6,086,543 A | 7/2000 | Anderson et al. | 600/567 |
| 6,086,544 A | 7/2000 | Hibner et al. | 600/568 |
| 6,096,042 A | 8/2000 | Herbert | 606/80 |
| 6,102,915 A | 8/2000 | Bresler et al. | 606/80 |
| 6,106,484 A | 8/2000 | Terwilliger | 600/568 |
| 6,110,128 A | 8/2000 | Andelin et al. | 600/566 |
| 6,110,129 A | 8/2000 | Terwilliger | 600/567 |
| 6,110,174 A | 8/2000 | Nichter | 606/72 |
| 6,120,462 A | 9/2000 | Hibner et al. | 600/566 |
| 6,135,769 A | 10/2000 | Kwan | 433/80 |
| 6,152,918 A | 11/2000 | Padilla et al. | 606/15 |
| 6,159,163 A | 12/2000 | Strauss et al. | 600/566 |
| 6,162,203 A | 12/2000 | Haaga | 604/272 |
| 6,183,442 B1 | 2/2001 | Athanasiou et al. | 604/154 |
| 6,210,376 B1 | 4/2001 | Grayson | 604/264 |
| 6,217,561 B1 | 4/2001 | Gibbs | 604/264 |
| 6,221,029 B1 | 4/2001 | Mathis et al. | 600/564 |
| 6,228,049 B1 | 5/2001 | Schroeder et al. | 604/93.01 |
| 6,228,088 B1 | 5/2001 | Miller et al. | 606/80 |
| 6,238,355 B1 | 5/2001 | Daum | 600/567 |
| 6,247,928 B1 | 6/2001 | Meller et al. | 433/80 |
| 6,248,110 B1 | 6/2001 | Reiley et al. | 606/93 |
| 6,257,351 B1 | 7/2001 | Ark et al. | 173/178 |
| 6,267,763 B1 | 7/2001 | Castro | 606/86 A |
| 6,273,715 B1 | 8/2001 | Meller et al. | 433/80 |
| 6,273,862 B1 | 8/2001 | Privitera et al. | 600/568 |
| 6,283,925 B1 | 9/2001 | Terwilliger | 600/568 |
| 6,283,970 B1 | 9/2001 | Lubinus | 606/80 |
| 6,287,114 B1 | 9/2001 | Meller et al. | 433/80 |
| 6,302,852 B1 | 10/2001 | Fleming, III et al. | 600/567 |
| 6,309,358 B1 * | 10/2001 | Okubo | 600/466 |
| 6,312,394 B1 | 11/2001 | Fleming, III | 600/567 |
| 6,315,737 B1 | 11/2001 | Skinner | 600/566 |
| 6,325,806 B1 | 12/2001 | Fox | 606/80 |
| 6,328,701 B1 | 12/2001 | Terwilliger | 600/567 |
| 6,328,744 B1 | 12/2001 | Harari et al. | 606/80 |
| 6,358,252 B1 | 3/2002 | Shapira | 606/80 |
| 6,382,212 B1 | 5/2002 | Borchard | 128/849 |
| 6,402,701 B1 | 6/2002 | Kaplan et al. | 600/567 |
| 6,419,490 B1 | 7/2002 | Kitchings Weathers, Jr. | 433/165 |
| 6,425,888 B1 | 7/2002 | Embleton et al. | 604/290 |
| 6,428,487 B1 | 8/2002 | Burdorff et al. | 600/568 |
| 6,443,910 B1 | 9/2002 | Krueger et al. | 600/567 |
| 6,458,117 B1 | 10/2002 | Pollins, Sr. | 604/523 |
| 6,468,248 B1 | 10/2002 | Gibbs | 604/164.01 |
| 6,478,751 B1 | 11/2002 | Krueger et al. | 600/566 |
| 6,488,636 B2 | 12/2002 | Bryan et al. | 600/565 |
| 6,523,698 B1 | 2/2003 | Dennehey et al. | 210/435 |
| 6,527,736 B1 | 3/2003 | Attinger et al. | 604/43 |
| 6,527,778 B2 | 3/2003 | Athanasiou et al. | 606/80 |
| 6,540,694 B1 | 4/2003 | Van Bladel et al. | 600/564 |
| 6,547,511 B1 | 4/2003 | Adams | 414/46.4 |
| 6,547,561 B2 | 4/2003 | Meller et al. | 433/80 |
| 6,550,786 B2 | 4/2003 | Gifford et al. | 279/75 |
| 6,554,779 B2 | 4/2003 | Viola et al. | 600/568 |
| 6,555,212 B2 | 4/2003 | Boiocchi et al. | 428/295.4 |
| 6,572,563 B2 | 6/2003 | Ouchi | 600/564 |
| 6,575,919 B1 | 6/2003 | Reiley et al. | 600/567 |
| 6,582,399 B1 | 6/2003 | Smith et al. | 604/152 |
| 6,585,622 B1 | 7/2003 | Shum et al. | 482/8 |
| 6,595,911 B2 | 7/2003 | LoVuolo | 600/30 |
| 6,595,979 B1 | 7/2003 | Epstein et al. | 604/506 |
| 6,613,054 B2 | 9/2003 | Scribner et al. | 606/93 |
| 6,616,632 B2 | 9/2003 | Sharp et al. | 604/117 |
| 6,620,111 B2 | 9/2003 | Stephens et al. | 600/567 |
| 6,626,848 B2 | 9/2003 | Nueenfeldt | 600/564 |
| 6,626,887 B1 | 9/2003 | Wu | 604/512 |
| 6,638,235 B2 | 10/2003 | Miller et al. | 600/566 |
| 6,656,133 B2 | 12/2003 | Voegele et al. | 600/568 |
| 6,689,072 B2 | 2/2004 | Kaplan et al. | 600/567 |
| 6,702,760 B2 | 3/2004 | Krause et al. | 600/564 |
| 6,702,761 B1 | 3/2004 | Damadian et al. | 600/576 |
| 6,706,016 B2 | 3/2004 | Cory et al. | 604/117 |
| 6,716,192 B1 | 4/2004 | Orosz, Jr. | 604/117 |
| 6,716,215 B1 | 4/2004 | David et al. | 606/80 |
| 6,716,216 B1 | 4/2004 | Boucher et al. | 606/86 |
| 6,730,043 B2 | 5/2004 | Krueger et al. | 600/567 |
| 6,730,044 B2 | 5/2004 | Stephens et al. | 600/568 |
| 6,749,576 B2 | 6/2004 | Bauer | 600/567 |
| 6,752,768 B2 | 6/2004 | Burdorff et al. | 600/568 |
| 6,752,816 B2 | 6/2004 | Culp et al. | 606/170 |
| 6,758,824 B1 | 7/2004 | Miller et al. | 600/568 |
| 6,761,726 B1 | 7/2004 | Findlay et al. | 606/182 |
| 6,796,957 B2 | 9/2004 | Carpenter et al. | 604/93.01 |
| 6,846,314 B2 | 1/2005 | Shapira | 606/80 |
| 6,849,051 B2 | 2/2005 | Sramek et al. | 600/565 |
| 6,855,148 B2 | 2/2005 | Foley et al. | 606/86 |
| 6,860,860 B2 | 3/2005 | Viola | 600/564 |
| 6,875,183 B2 | 4/2005 | Cervi | 600/567 |
| 6,875,219 B2 | 4/2005 | Arramon et al. | 606/92 |
| 6,884,245 B2 | 4/2005 | Spranza | 606/79 |
| 6,887,209 B2 | 5/2005 | Kadziauskas et al. | 600/565 |
| 6,890,308 B2 | 5/2005 | Islam | 600/564 |
| 6,905,486 B2 | 6/2005 | Gibbs | 604/264 |
| 6,930,461 B2 | 8/2005 | Rutkowski | 318/567 |
| 6,942,669 B2 | 9/2005 | Kurc | 606/80 |
| 6,969,373 B2 | 11/2005 | Schwartz et al. | 604/170.03 |
| 7,001,342 B2 | 2/2006 | Faciszewski | 600/564 |
| 7,008,381 B2 | 3/2006 | Janssens | 600/564 |
| 7,008,383 B1 | 3/2006 | Damadian et al. | 600/567 |
| 7,008,394 B2 | 3/2006 | Geise et al. | 615/6.15 |
| 7,018,343 B2 | 3/2006 | Plishka | 600/564 |
| 7,025,732 B2 | 4/2006 | Thompson et al. | 600/654 |
| 7,063,672 B2 | 6/2006 | Schramm | 600/564 |
| 7,063,703 B2 | 6/2006 | Reo | 606/79 |
| 7,137,985 B2 | 11/2006 | Jahng | 606/61 |
| 7,186,257 B2 | 3/2007 | Kim | 606/96 |
| 7,207,949 B2 | 4/2007 | Miles et al. | 600/554 |
| 7,226,450 B2 | 6/2007 | Athanasiou et al. | 606/80 |
| 7,229,401 B2 | 6/2007 | Kindlein | 600/7 |
| 7,278,972 B2 | 10/2007 | Lamoureux et al. | 600/567 |
| 7,331,930 B2 | 2/2008 | Faciszewski | 600/567 |

(56) References Cited

U.S. PATENT DOCUMENTS

| | | | |
|---|---|---|---|
| 7,513,722 B2 | 4/2009 | Greenberg et al. | 408/202 |
| 7,670,328 B2 | 3/2010 | Miller | 604/506 |
| 7,699,850 B2 | 4/2010 | Miller | 606/80 |
| 7,811,260 B2 | 10/2010 | Miller et al. | 604/188 |
| 7,815,642 B2 | 10/2010 | Miller | 606/79 |
| 7,850,620 B2 | 12/2010 | Miller et al. | 600/568 |
| 7,951,089 B2 | 5/2011 | Miller | 600/566 |
| 7,988,643 B2 | 8/2011 | Hoffmann et al. | 600/567 |
| 8,038,664 B2 | 10/2011 | Miller et al. | 604/506 |
| 8,217,561 B2 | 7/2012 | Fukuzawa et al. | 313/141 |
| 8,419,683 B2 | 4/2013 | Miller et al. | 604/117 |
| 8,480,632 B2 | 7/2013 | Miller et al. | 604/188 |
| 8,506,568 B2 | 8/2013 | Miller | 606/80 |
| 8,641,715 B2 | 2/2014 | Miller | 606/80 |
| 8,656,929 B2 | 2/2014 | Miller et al. | 128/898 |
| 8,668,698 B2 | 3/2014 | Miller et al. | 606/80 |
| 8,684,978 B2 | 4/2014 | Miller et al. | 604/235 |
| 8,690,791 B2 | 4/2014 | Miller | 600/562 |
| 8,715,287 B2 | 5/2014 | Miller | 606/80 |
| 2001/0014439 A1 | 8/2001 | Meller et al. | 433/50 |
| 2001/0047183 A1 | 11/2001 | Privitera et al. | 606/170 |
| 2001/0053888 A1 | 12/2001 | Athanasiou et al. | 604/154 |
| 2002/0042581 A1 | 4/2002 | Cervi | 600/567 |
| 2002/0055713 A1 | 5/2002 | Gibbs | 604/164.01 |
| 2002/0120212 A1 | 8/2002 | Ritchart et al. | 600/567 |
| 2002/0138021 A1 | 9/2002 | Pflueger | 600/565 |
| 2002/0151902 A1 | 10/2002 | Riedel et al. | 600/567 |
| 2003/0028146 A1 | 2/2003 | Aves | 604/164.06 |
| 2003/0032939 A1 | 2/2003 | Gibbs | 604/510 |
| 2003/0036747 A1 | 2/2003 | Ie et al. | 606/1 |
| 2003/0050574 A1 | 3/2003 | Krueger | 600/567 |
| 2003/0078586 A1 | 4/2003 | Shapira | 606/80 |
| 2003/0114858 A1 | 6/2003 | Athanasiou et al. | 606/80 |
| 2003/0125639 A1 | 7/2003 | Fisher et al. | 600/564 |
| 2003/0153842 A1 | 8/2003 | Lamoureux et al. | 600/564 |
| 2003/0191414 A1 | 10/2003 | Reiley et al. | 600/567 |
| 2003/0195436 A1 | 10/2003 | Van Bladel et al. | 600/584 |
| 2003/0195524 A1 | 10/2003 | Barner | 606/119 |
| 2003/0199787 A1 | 10/2003 | Schwindt | 600/568 |
| 2003/0199879 A1 | 10/2003 | Spranza | 606/79 |
| 2003/0216667 A1 | 11/2003 | Viola | 600/564 |
| 2003/0225344 A1 | 12/2003 | Miller | 600/568 |
| 2003/0225364 A1 | 12/2003 | Kraft et al. | 604/35 |
| 2003/0225411 A1 | 12/2003 | Miller | 606/80 |
| 2004/0019297 A1 | 1/2004 | Angel | 600/564 |
| 2004/0019299 A1 | 1/2004 | Ritchart et al. | 600/567 |
| 2004/0034280 A1 | 2/2004 | Privitera et al. | 600/170 |
| 2004/0049128 A1 | 3/2004 | Miller et al. | 600/566 |
| 2004/0049205 A1* | 3/2004 | Lee et al. | 606/130 |
| 2004/0064136 A1 | 4/2004 | Papineau et al. | 606/41 |
| 2004/0073139 A1 | 4/2004 | Hirsch et al. | 600/564 |
| 2004/0092946 A1 | 5/2004 | Bagga et al. | 606/93 |
| 2004/0127814 A1 | 7/2004 | Negroni | 600/567 |
| 2004/0153003 A1 | 8/2004 | Cicenas et al. | 600/564 |
| 2004/0158172 A1 | 8/2004 | Hancock | 600/564 |
| 2004/0158173 A1 | 8/2004 | Voegele et al. | 600/568 |
| 2004/0162505 A1 | 8/2004 | Kaplan et al. | 600/567 |
| 2004/0191897 A1 | 9/2004 | Muschler | 435/325 |
| 2004/0210161 A1 | 10/2004 | Burdorff et al. | 600/566 |
| 2004/0215102 A1 | 10/2004 | Ikehara et al. | 600/562 |
| 2004/0220497 A1 | 11/2004 | Findlay et al. | 600/562 |
| 2005/0027210 A1 | 2/2005 | Miller | 600/567 |
| 2005/0040060 A1 | 2/2005 | Andersen et al. | 206/363 |
| 2005/0075581 A1 | 4/2005 | Schwindt | 600/568 |
| 2005/0085838 A1 | 4/2005 | Thompson et al. | 606/170 |
| 2005/0101880 A1 | 5/2005 | Cicenas et al. | 600/567 |
| 2005/0113716 A1 | 5/2005 | Mueller, Jr. et al. | 600/568 |
| 2005/0119660 A1 | 6/2005 | Bourlion et al. | 606/80 |
| 2005/0124915 A1 | 6/2005 | Eggers et al. | 600/568 |
| 2005/0131345 A1 | 6/2005 | Miller | 604/117 |
| 2005/0148940 A1 | 7/2005 | Miller | 604/187 |
| 2005/0165328 A1 | 7/2005 | Heske et al. | 600/566 |
| 2005/0165403 A1 | 7/2005 | Miller | 606/79 |
| 2005/0165404 A1 | 7/2005 | Miller | 606/80 |
| 2005/0171504 A1 | 8/2005 | Miller | 604/506 |
| 2005/0182394 A1 | 8/2005 | Spero et al. | 606/21 |
| 2005/0200087 A1 | 9/2005 | Vasudeva et al. | 279/143 |
| 2005/0203439 A1 | 9/2005 | Heske et al. | 600/566 |
| 2005/0209530 A1 | 9/2005 | Pflueger | 600/567 |
| 2005/0215921 A1 | 9/2005 | Hibner et al. | 600/566 |
| 2005/0228309 A1 | 10/2005 | Fisher et al. | 600/562 |
| 2005/0261693 A1 | 11/2005 | Miller et al. | 606/80 |
| 2006/0011506 A1 | 1/2006 | Riley | 206/570 |
| 2006/0015066 A1 | 1/2006 | Turieo et al. | 604/136 |
| 2006/0036212 A1 | 2/2006 | Miller | 604/48 |
| 2006/0052790 A1 | 3/2006 | Miller | 606/80 |
| 2006/0074345 A1 | 4/2006 | Hibner | 600/566 |
| 2006/0079774 A1 | 4/2006 | Anderson | 600/442 |
| 2006/0089565 A1 | 4/2006 | Schramm | 600/568 |
| 2006/0122535 A1 | 6/2006 | Daum | 600/565 |
| 2006/0129082 A1 | 6/2006 | Rozga | 604/6.04 |
| 2006/0144548 A1 | 7/2006 | Beckman et al. | 163/1 |
| 2006/0149163 A1 | 7/2006 | Hibner et al. | 600/566 |
| 2006/0167377 A1 | 7/2006 | Ritchart et al. | 600/566 |
| 2006/0167378 A1 | 7/2006 | Miller | 600/566 |
| 2006/0167379 A1 | 7/2006 | Miller | 600/566 |
| 2006/0184063 A1 | 8/2006 | Miller | 600/568 |
| 2006/0189940 A1 | 8/2006 | Kirsch | 604/164.1 |
| 2006/0206132 A1 | 9/2006 | Conquergood et al. | 606/180 |
| 2007/0016100 A1 | 1/2007 | Miller | 600/567 |
| 2007/0049945 A1 | 3/2007 | Miller | 606/86 |
| 2007/0149920 A1 | 6/2007 | Michels et al. | 604/93.01 |
| 2007/0213735 A1 | 9/2007 | Saadat et al. | 606/79 |
| 2007/0270775 A1 | 11/2007 | Miller et al. | 604/506 |
| 2008/0015467 A1 | 1/2008 | Miller | 600/566 |
| 2008/0015468 A1 | 1/2008 | Miller | 600/568 |
| 2008/0045857 A1 | 2/2008 | Miller et al. | 600/566 |
| 2008/0045860 A1 | 2/2008 | Miller et al. | 600/567 |
| 2008/0045861 A1 | 2/2008 | Miller et al. | 600/567 |
| 2008/0045965 A1 | 2/2008 | Miller et al. | 606/80 |
| 2008/0140014 A1 | 6/2008 | Miller et al. | 604/180 |
| 2008/0177200 A1 | 7/2008 | Ikehara et al. | 600/567 |
| 2008/0215056 A1 | 9/2008 | Miller et al. | 606/80 |
| 2008/0221580 A1 | 9/2008 | Miller et al. | 606/80 |
| 2009/0069716 A1 | 3/2009 | Freeman et al. | 600/583 |
| 2009/0093677 A1 | 4/2009 | Smith | 600/114 |
| 2009/0194446 A1 | 8/2009 | Miller et al. | 206/438 |
| 2011/0046507 A1 | 2/2011 | Herndon | 600/547 |

FOREIGN PATENT DOCUMENTS

| | | | |
|---|---|---|---|
| CN | 2320209 | 5/1999 | |
| CN | 2664675 | 12/2004 | |
| DE | 10057931 | 11/2007 | |
| EP | 517000 | 12/1992 | A61M 5/168 |
| EP | 0807412 | 11/1997 | |
| EP | 0807412 A1 | 11/1997 | A61B 17/32 |
| EP | 1099450 | 10/2000 | |
| EP | 1314452 | 5/2003 | |
| EP | 1447050 | 8/2004 | |
| EP | 1421907 | 6/2010 | |
| FR | 853349 | 3/1940 | |
| FR | 2457105 | 5/1979 | |
| FR | 2516386 | 11/1981 | |
| GB | 2130890 A | 6/1984 | |
| JP | 1052433 | 8/1984 | |
| JP | 59119808 | 8/1984 | |
| JP | 61032663 | 9/1986 | |
| JP | 2001505076 | 4/2001 | |
| WO | WO/92/08410 | 5/1992 | |
| WO | 93/07819 | 4/1993 | A61B 17/32 |
| WO | 96/31164 | 10/1996 | A61B 17/34 |
| WO | 98/06337 | 2/1998 | A61B 17/16 |
| WO | WO/98/52638 | 11/1998 | |
| WO | 99/18866 | 4/1999 | A61B 17/34 |
| WO | 99/52444 | 10/1999 | A61B 17/00 |
| WO | WO/00/009024 | 2/2000 | |
| WO | 00/56220 | 9/2000 | A61B 10/00 |
| WO | WO/01/78590 | 10/2001 | |
| WO | 02/41792 A1 | 5/2002 | A61B 17/16 |
| WO | 0241792 | 5/2002 | A61B 17/16 |
| WO | 02096497 | 12/2002 | A61M 31/00 |
| WO | WO/03/015637 | 2/2003 | |
| WO | WO/2005/072625 | 8/2005 | |

(56) References Cited

FOREIGN PATENT DOCUMENTS

| WO | 2005110259 | 11/2005 | ............ | A61B 17/88 |
|----|------------|---------|--------------|------------|
| WO | 2005112800 | 12/2005 | ............ | A61B 17/34 |
| WO | WO/2008/033874 | 3/2008 | | |
| WO | 2008081438 | 7/2008 | | |
| WO | WO/2011/123703 | 10/2011 | | |

OTHER PUBLICATIONS

International PCT Search Report PCT/US03/17203, 8 pages, Mailed Sep. 16, 2003.
International PCT Search Report PCT/US2004/037753, 6 pages, Mailed Apr. 19, 2005.
Communication relating to the results of the partial International Search Report for PCT/US2005/002484, 6 pages, Mailed May 19, 2005.
International PCT Search Report and Written Opinion PCT/US2004/037753, 16 pages, Mailed Jul. 8, 2005.
International PCT Search Report and Written Opinion PCT/US2005/002484, 15 pages, Mailed Jul. 22, 2005.
Cummins, Richard O., et al, "ACLS-Principles and Practice", ACLS-The Reference Textbook, American Heart Association, pp. 214-218, 2003.
Riley et al., "A Pathologist's Perspective on Bone Marrow Aspiration Biopsy: I. Performing a Bone Marrow Examination," Journal of Clinical Laboratory Analysis 18, pp. 70-90, 2004.
International Preliminary Report on Patentability PCT/US2005/002484, 9 pages, Mailed Aug. 3, 2006.
Official Action for European Application No. 03756317.8 (4 pages), Dec. 28, 2006.
International Search Report and Written Opinion for International Application No. PCT/US2006/025201 (18 pages), Jan. 29, 2007.
Pediatrics, Official Journal of the American Academy of Pediatrics, Pediatrics, 2005 American Heart Association Guidelines for Cardiopulmonary Resuscitation and Emergency Cardiovascular Care of Pediatric and Neonatal Patients:Pediatric Advanced Life Support, Downloaded from www.pediatrics.org, Feb. 21, 2007.
Liakat A. Parapia, Trepanning or trephines: a history of bone marrow biopsy, British Journal of Haematology, pp. 14-19 2007, Date 2007.
Australian Exam Report on Patent Application No. 2003240970, 2 pages, Oct. 15, 2007.
Pediatric Emergency, Intraosseous Infusion for Administration of Fluids and Drugs, www.cookgroup.com, 1 pg, 2000.
Michael Trotty, "Technology (A Special Report)—The Wall Street Journal 2008 Technology Innovation Awards—This years winners include: an IV alternative, a better way to make solar panels, a cheap, fuel efficient car and a better way to see in the dark", The Wall Street Journal, Factiva, 5 pages, 2008.
Buckley et al., CT-guided bone biopsy: Initial experience with commercially available hand held Black and Decker drill, European Journal of Radiology 61, pp. 176-180, 2007.
Hakan et al., CT-guided Bone BiopsyPerformed by Means of Coaxial Bopsy System with an Eccentric Drill, Radiology, pp. 549-552, Aug. 1993.
European Search Report 08158699.2-1265, 4 pages, Aug. 2008.
International Search Report and Written Opinion, PCT/US2007/078204, 14 pages, Mailing Date May 15, 2008.
International Search Report and Written Opinion, PCT/US08/52943, 8 pages, Mailing Date Sep. 26, 2008.
European Office Action Communication, Application No. 08158699.2-1265/1967142, 10 pages, Nov. 4, 2008.
Gunal et al., Compartment Syndrome After Intraosseous Infusion: An Expiremental Study in Dogs, Journal of Pediatric Surgery, vol. 31, No. 11, pp. 1491-1493, Nov. 1996.
International Search Report, PCT/US2007/072217, 20 pages, Mailing Date Mar. 31, 2008.
International Search Report, PCT/US2007/072209, 18 pages, Mailing Date Apr. 25, 2008.
International Search Report, PCT/US2006/025201, 12 pages, Mailing Date Feb. 7, 2008.
Communication Pursuant to Article 94(3) EPC, Application No. 05 712 091.7-1265, 4 pages, Apr. 8, 2008.
Notification of the First Chinese Office Action, Application No. 200580003261.8, 3 pages, Mar. 21, 2008.
International Search Report and Written Opinion, PCT/US08/500346, 12 pages, Mailing Date May 22, 2008.
PCT Invitation to Pay Additional Fees, PCT/US2007/072209, 9 pages, Mailing Dec. 3, 2007.
"Proven reliability for quality bone marrow samples", Special Procedures, Cardinal Health, 6 pages, 2003.
F.A.S.T. 1 Intraosseous Infusion System with Depth-Control Mechanism Brochure, 6 pages, 2000.
BioAccess.com, Single Use Small Bone Power Tool—How It Works, 1 pg, Printed Jun. 9, 2008.
International Search Report and Written Opinion, PCT/US2007/078203, 15 pages, Mailing Date May 13, 2008.
International Search Report and Written Opinion, PCT/US2007/072202, 17 pages, Mailing Date Mar. 25, 2008.
International Search Report and Written Opinion, PCT/US2007/078207, 13 pages, Mailing Date Apr. 7, 2008.
International Search Report and Written Opinion, PCT/US2007/078205, 13 pages, Mailing date Sep. 11, 2007.
European Office Action EP03731475.4, 4 pages, Oct. 11, 2007.
U.S. Appl. No. 11/427,501 Non Final Office Action, 14 pages, Mailed Aug. 7, 2008.
Non-Final Office Action, U.S. Appl. No. 10/449,476, 8 pages, Mailed Oct. 29, 2008.
International Preliminary Report on Patentability, PCT/US2007/072202, 10 pages, Mailed Jan. 15, 2009.
International Preliminary Report on Patentability, PCT/US2007/072217, 11 pages, Mailed Feb. 12, 2009.
Åström, K.G., "Automatic Biopsy Instruments Used Through a Coaxial Bone Biopsy System with an Eccentric Drill Tip," Acta Radiologica, 1995; 36:237-242, May 1995.
Åström, K. Gunnar O., "CT-guided Transsternal Core Biopsy of Anterior Mediastinal Masses," Radiology 1996; 199:564-567, May 1996.
Extended European Search Report for European application 07842284.7. Mailed Mar. 16, 2011.
Extended European Search Report for European application 07842285.4. Mailed Mar. 17, 2011.
Extended European Search Report for European application 07842286.2. Mailed Mar. 18, 2011.
Extended European Search Report for European application 07842288.8. Mailed Mar. 16, 2011.
International Preliminary Report on Patentability for international application PCT/US2007/078203. Dated Mar. 26, 2009.
International Preliminary Report on Patentability for international application PCT/US2007/078207. Dated Mar. 26, 2009.
International Preliminary Report on Patentability for international application PCT/US2007/078205. Dated Mar. 26, 2009.
International Preliminary Report on Patentability for international application PCT/US2007/078204. Dated Apr. 2, 2009.
Notice of Allowance in U.S. Appl. No. 11/042,912, mailed Sep. 24, 2013.
Notice of Allowance in U.S. Appl. No. 11/620,927 mailed Jun. 3, 2014.
Notice of Allowance in U.S. Appl. No. 11/853,678, mailed Oct. 11, 2013.
Notice of Allowance in U.S. Appl. No. 11/853,678, mailed Nov. 8, 2013.
Notice of Allowance in U.S. Appl. No. 12/331,979, mailed Dec. 23, 2013.
Notice of Allowance in U.S. Appl. No. 12/427,310, mailed Nov. 29, 2013.
Notice of Allowance in U.S. Appl. No. 12/899,696, mailed Nov. 12, 2013.
Notice of Allowance issued in U.S. Appl. No. 11/253,959, mailed May 20, 2013.
Notice of Allowance issued on Mar. 4, 2014 in U.S. Appl. No. 11/253,467.
Office Action for Chinese application 200780001188.X with English translation. Mailed Nov. 9, 2010.

(56) References Cited

OTHER PUBLICATIONS

Office Action for Chinese application 200780001190.7 with English translation. Mailed Jun. 2, 2010.
Office Action for Chinese application 200780001196.4 with English translation. Mailed Jul. 12, 2010.
Office Action for Chinese application 200780001198.3 with English translation. Mailed Apr. 27, 2010.
Office Action for European application 07842284.7. Mailed May 3, 2012.
Office Action for European application 07842285.4. Mailed May 3, 2012.
Office Action for European application 07842286.2. Mailed Apr. 30, 2012.
Office Action for European application 07842288.8. Mailed May 3, 2012.
Response to Office Action for European application 07842284.7. Filed Nov. 9, 2012.
Response to Office Action for European application 07842285.4. Filed Nov. 13, 2012.
Response to Office Action for European application 07842286.2. Filed Nov. 8, 2012.
Response to Office Action for European application 07842288.8. Filed Nov. 9, 2012.
Response to Official Letter for European application 07842284.7. Filed Oct. 14, 2011.
Response to Official Letter for European application 07842285.4. Filed Oct. 14, 2011.
Response to Official Letter for European application 07842286.2. Filed Oct. 14, 2011.
Response to Official Letter for European application 07842288.8. Filed Oct. 14, 2011.

* cited by examiner

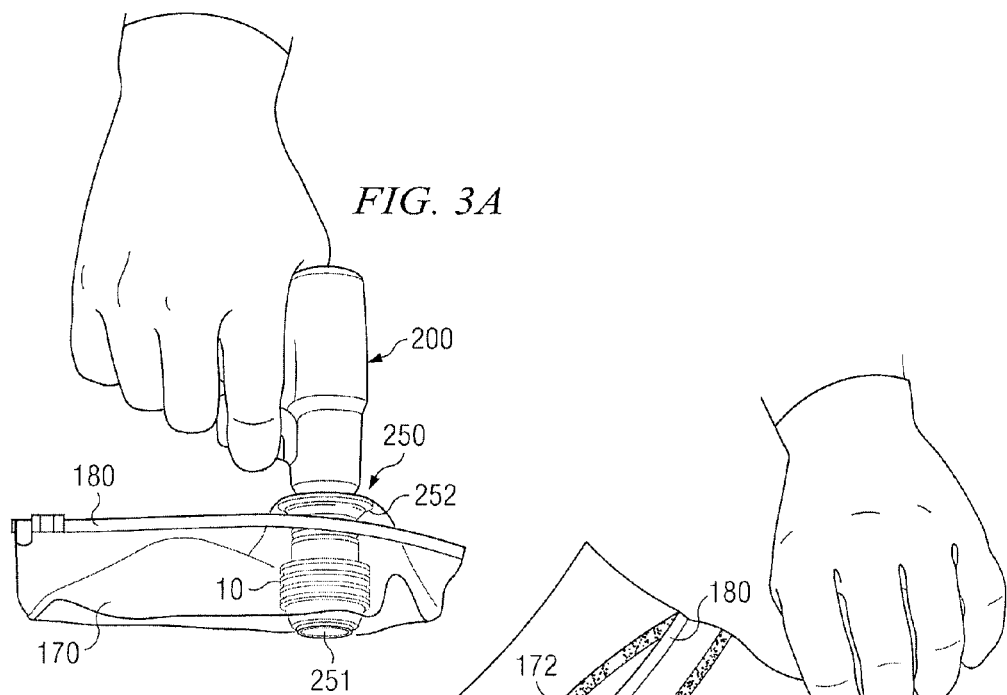
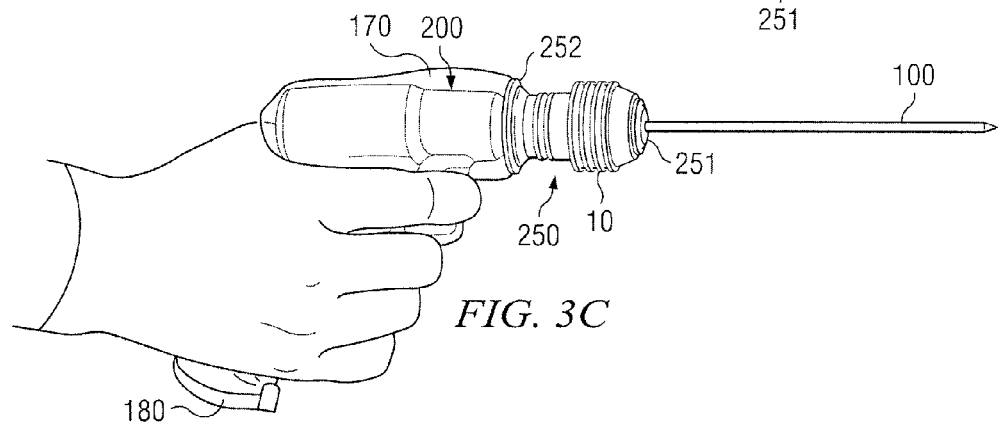

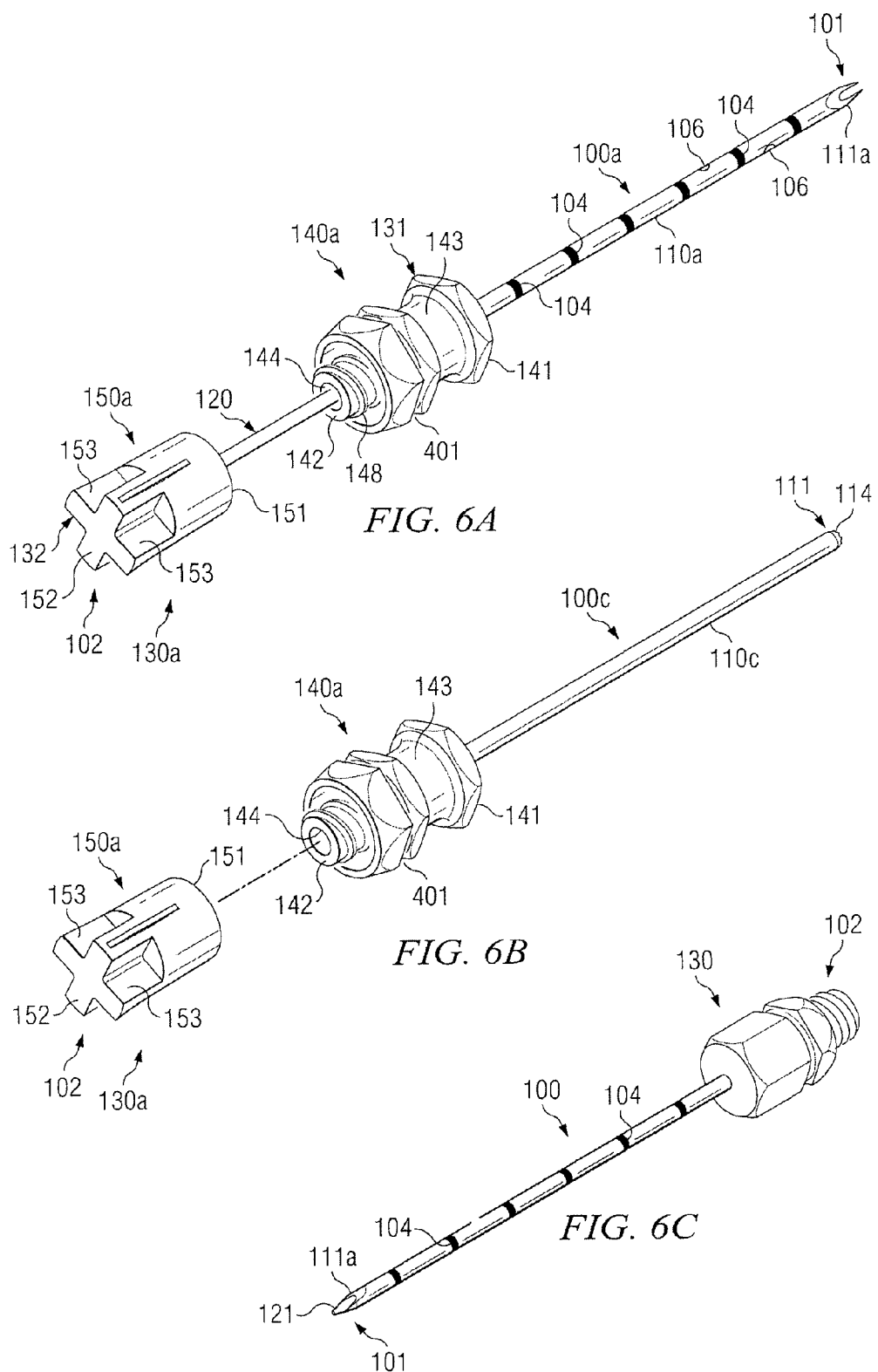

US 8,944,069 B2

ASSEMBLIES FOR COUPLING INTRAOSSEOUS (IO) DEVICES TO POWERED DRIVERS

RELATED APPLICATION

This application claims priority under 35 U.S.C. 120 to and is a continuation-in-part application of U.S. patent application Ser. No. 11/853,701, filed Sep. 11, 2007, now U.S. Pat. No. 8,656,929, which claims the benefit of U.S. Provisional Patent Application Ser. No. 60/825,325 entitled "Apparatus and Methods for Biopsy and Aspiration of Bone Marrow" filed Sep. 12, 2006, and claims the benefit of U.S. Provisional Patent Application Ser. No. 60/910,122 entitled "Powered Driver Intraosseous Device and Methods To Access Bone Marrow" filed Apr. 4, 2007. The contents of these applications are incorporated herein in their entirety by this reference.

TECHNICAL FIELD

The present disclosure is related generally to non-surgical medical procedures such as diagnosis, evaluation and treatment of bones, including factures, vertebral fractures, and/or other disease or injury to a patient's spine and to medical devices associated with such procedures. The disclosure also relates to medical procedure trays and kits for use in conjunction with diagnostic and therapeutic medical procedures for bone related disorders.

BACKGROUND OF THE DISCLOSURE

There are many clinical conditions that require access to bone tissues, such as bone marrow. In some cases it is important to access and retrieve bone tissue and/or bone marrow for diagnosis or treatment of conditions such as but not limited to, osteoporosis, degenerative bone diseases, fractures, vertebral fractures, cancers of any type and hematologic disease of any origin. For example, it may be necessary to access bone tissues and/or bone marrow to obtain a sample or specimen for diagnostic testing.

In other cases it may be necessary to introduce a medicament or a therapeutic agent directly into bone tissue or bone marrow that may be useful to treat or ameliorate a clinical condition. For example, it may be necessary to treat diseases with bone marrow or stem cell transplants to restore functioning blood cells. Such conditions may include, but are not limited to, acute leukemia, brain tumors, breast cancer, Hodgkin's disease, multiple myeloma, neuroblastoma, non-Hodgkin's lymphomas, ovarian cancer, sarcoma and testicular cancer. In other cases, it may be necessary to treat conditions such as osteoporosis, degenerative bone disorders, or fractures by introducing a medicament into the bone or bone marrow.

Gaining access to bone and associated bone marrow for a small biopsy specimen and/or aspiration of a larger quantity of bone marrow and/or to introduce a medicament may be difficult, traumatic and occasionally dangerous, depending on each selected target area for harvesting bone and/or associated bone marrow, operator expertise and patient. Currently available devices and techniques for gaining access to a bone and associated bone marrow may include an intraosseous (IO) needle with a removable trocar disposed therein. Various shapes and sizes of handles may be used to apply manual pressure and to manually rotate the IO needle and removable trocar as a set. Such manual IO devices often require substantial force to break through the outer cortex of a bone. Exertion of such force may cause pain to a patient and may sometimes damage the bone and/or IO device. Such force may especially cause damage when harvesting bone marrow from children with softer bone structures or from any patient with bones deteriorated by disease (osteoporosis, cancer, fractures).

Occasionally a core specimen of bone and/or bone marrow may not be successfully retrieved using a standard biopsy needle. Thus, multiple insertions at different sites may be necessary to obtain a satisfactory bone and/or bone marrow biopsy specimen. Risks to health care personnel may be higher because of increased handling of blood contaminated sharp instruments. Accidental needle sticks and missed target areas may further complicate procedures and increase risks to health care personnel and/or patients.

Conventional bone marrow transplant techniques may require multiple penetration sites (up to 20 per patient) in order to obtain enough bone marrow to perform a routine bone marrow transplant. This procedure is often labor intensive. Conventional biopsy needles and/or aspiration needles are typically inserted with considerable manual force. This force may cause loss of control or operator fatigue. When the biopsy needle or aspiration needle is in place, an associated trocar is generally removed and a syringe attached to one end of the needle to aspirate a few cubic centimeters of bone marrow. The biopsy or aspiration needle is then withdrawn. A new insertion site may be penetrated, often about a centimeter from the first insertion site. The procedure may be repeated multiple times. There is a need for better apparatus and methods for accessing bone tissue.

Vertebroplasty may often be performed with a patient sedated but awake, in a x-ray suite or an operating room. During vertebroplasty, a bone cement is typically injected under pressure directly into a fractured vertebra. Once in position, the cement may harden in about ten minutes or less, depending upon the type of cement, congealing the fragments of the fractured vertebra and providing immediate stability.

SUMMARY OF THE DISCLOSURE

In accordance with the teachings of the present disclosure, apparatus, devices, medical procedure trays, medical kits, and therapeutic and diagnostic methods are provided for gaining access to bone tissue and/or for vascular access through bone tissue. Access to bone tissue may be used for providing a medicament or a therapeutic agent to bone tissues and/or to obtain clinical samples by techniques such as aspiration and/or biopsy of bone marrow. In some embodiments, the present disclosure provides methods, apparatus, medical procedure trays and kits for access to vertebral bones for therapeutic and diagnostic purposes.

One aspect of the present disclosure may include an intraosseous (IO) device such as an IO needle set and a coupler assembly, with a non-sterile driver (manual or power driven) operable to insert the IO device into a bone and/or associated bone marrow. The coupler assembly may comprise one end operable to releasably attach to an IO device and another end operable to releasably attach to a non-sterile driver. Use of a non-sterile driver may be facilitated by a containment bag or sterile glove that is comprised in the coupler assembly and is used to prevent direct contact of the non-sterile driver with sterile needles and a patient during a medical procedure such as diagnostic evaluation and/or providing one or more therapeutic agents to bone. A non-sterile driver may be used repeatedly in conjunction with disposable sterile IO needle sets and couplers.

One aspect of the present disclosure may include placing a powered driver within a containment bag or sterile enclosure that may be attached to the first end of a coupler assembly, to provide isolation between the powered driver and an exterior environment and maintain a fluid barrier with adjacent portions of driver housing. The containment bag may be formed from relatively flexible, lightweight, clear plastic-type materials. The containment bag may comprise a flexible stay on one side that may be opened to slide in a powered driver. The containment bag may further comprise a flap and an adhesive strip that may be used to seal in the powered driver prior to use, such that a sterile person does not contact the non-sterile driver. The containment bag may be attached to the coupler attachment by an adhesive such as hot glue. However, a wide variety of connecting mechanisms such as, port assemblies, connectors, receptacles, fittings, hubs, hub assemblies, latching mechanisms and/or other types of connecting devices incorporating teachings of the present disclosure may be satisfactorily used to attach a container bag with the coupler assembly.

The end of the coupler assembly at which a containment bag may be attached may be proximate a tortuous path. A tortuous path may be a non-linear path and may comprise sharp curves and/or sharp bends such that bacteria, viruses and/or other pathogens that may be present on a non-sterile powered driver cannot easily traverse to cause contamination of a sterile IO device attached at the other end of the coupler assembly. A tortuous path may also prevent contamination by bodily fluids that may contain pathogens of non-sterile and sterile components of medical devices and/or exposure of personnel performing the medical procedures of the disclosure to such contaminants.

A further aspect of the present disclosure may include a coupler assembly further operable to releasably engage an intraosseous device with portions of a drive shaft extending from one end of a powered driver. The coupler assembly may allow the powered driver to rotate or "spin" an intraosseous device at an insertion site (power in). The coupler assembly may also allow the powered driver to rotate or "spin" an intraosseous device during removal from the insertion site (power out). This feature of the present disclosure may also be referred to as "power in and power out."

Connectors as set forth above may also be used to releasably engage the coupler with a powered driver and/or the intraosseous device. In some embodiments, a coupler may comprise a spinner which may be used to releasably attach an intraosseous device to the second end of the coupler assembly.

IO devices and needle sets that may be attached to a coupler assembly may include one or more of the following: IO needles/devices/systems operable to provide access to a bone; IO needles/devices/systems operable to provide one or more therapeutic agents to bone; IO needles/devices/systems operable to access vertebral bones; IO needles/devices/systems operable to obtain a sample of bone and/or bone marrow such as a biopsy needle system or a bone marrow aspiration system. One or more types of IO needles/devices/systems may be operable to be releasably attached to the coupler assemblies of the disclosure based in part by the application for which the devices, systems and/or methods may be used for.

In some aspects, the present disclosure may include medical procedure trays comprising one or more IO needle sets and/or other intraosseous devices, a coupler assembly comprising a sterile containment bag, and optionally comprising a non-sterile power driver.

In accordance with the teachings of the present disclosure, one or more therapeutic agents may be delivered to a bone of a patient in need thereof. A therapeutic agent delivered using the methods, devices, medical procedure trays, and/or medical kits of the disclosure may have direct effects on bone tissue or bone marrow such as but not limited to inducing bone tissue regeneration, bone strengthening, bone growth, regeneration of bone marrow, growth inhibition of cancerous cells in bone or bone marrow or combinations thereof. Alternatively, therapeutic agents may be delivered via the bone, using the devices and methods of this disclosure, to the vasculature or other effector sites and may mediate their therapeutic effects at such other sites. Some non-limiting exemplary therapeutic agents that may have direct effects on bone tissue include bone/surgical cements, bone morphogenetic factors, cartilage-derived morphogenetic factors, osteogenic factors, differentiating factors, anti-resorption agents, hormones, growth hormones, nucleic acid constructs encoding one or more of such agents, or pharmaceutical chemicals.

One aspect of the present disclosure may include a therapeutic method that may comprise accessing bone, such as a fractured bone, by inserting an intraosseous needle or needle set into a bone using a non-sterile driver and coupler assembly where the intraosseous needle is operable to deliver a therapeutic agent, such as a surgical or bone cement, to the fractured bone; and delivering the therapeutic agent to the bone. In some aspects, the one or more therapeutic agents may stabilize, and/or strengthen, and/or regenerate and/or rebuild a fractured bone.

In an exemplary procedure, an intraosseous needle set may be used to initially cut through bone using a powered driver and coupler assembly (power in). An intraosseous needle set may include a cannula having a single lumen and a trocar or stylet operable to be slidably disposed within the lumen of the cannula. Various types of connections including, but not limited to, Luer lock connections may be used to releasably engage a trocar within a cannula. After insertion of a cannula into the bone a trocar maybe filled with surgical cement and maybe slidably disposed into the lumen of the cannula to inject or deliver the surgical cement into the fractured bone. After the surgical cement is delivered the trocar may be slidably removed followed by withdrawal of the cannula using the powered driver (power out).

Some non-limiting exemplary uses for methods, devices, and medical procedure trays of the present disclosure may include use during various types of procedures for strengthening or repairing fractured bones, procedures for strengthening or repairing bones that are weakened (by osteoporosis, aging, degenerative bone diseases or cancer), for ameliorating and/or relieving pain due to compression fractures (such as spinal compression fractures), vertebroplasty procedures to inject bone cements into spinal bones, procedures for the delivery of one or more therapeutic agents to a bone, stem cell transplant procedures. Bones of any kind, such as but not limited to, vertebral bones, neck bones, sternum, rib, clavicle, femoral, pelvic, wrist and the distal ends of the long bones may be accessed, evaluated and treated by the present devices and methods.

In some aspects, the present disclosure provides medical procedure trays comprising intraosseous devices for use in vertebroplasty methods. In some aspects, a medical procedures tray of the disclosure may be comprised of several smaller trays. For example, one tray may comprise an IO device/needle sets (e.g., designed to penetrate and deliver a therapeutic agent to bone); another tray may comprise another intraosseous device (e.g., designed to obtain a biological specimen from bone or designed to deliver another therapeutic agent); yet another tray may comprise a coupler assembly comprising a sterile containment bag. All these trays may be then packaged into one bigger tray. Typically all the devices will be sterilized and packaged with appropriate sterile techniques. The tray may also optionally comprise a non-sterile powered driver which may be packaged in a separate section of the tray or provided separately with the tray.

A vertebral procedure tray may comprise an IO needle set designed to penetrate into vertebral bones and deliver at least one therapeutic agent into the vertebral bone. A vertebral needle set may include a cannula having a lumen and a trocar or stylet operable to be slidably disposed within the lumen of the cannula and/or a cutting tip. The vertebral IO needles may be releasably attached to a first end of the coupler assembly while the non-sterile power driver may be attached to a second end of the coupler assembly.

As vertebral procedures require imaging, such as fluoroscopy imaging or x-ray imaging techniques, to position a vertebral needle at the correct insertion site and/or to monitor the injection of bone cement into a vertebral body, one aspect of the present disclosure relates to vertebral needles comprising a small hub for providing the least obstruction to visually viewing the needle and bone. Some embodiments, relate to the designing small IO needle hubs that allow for a clear view to an operator while performing a medical procedure as set forth in the present disclosure.

A vertebral/medical procedure tray as set forth above may also comprise a bone and/or bone marrow biopsy system, having a biopsy needle or biopsy needle set that may be releasably attached to the first end of the coupler assembly. The biopsy needle set may include a trocar operable to be slidably or releasably disposed within the lumen of the vertebral needle set cannula. A single helical thread may be provided at one end of a biopsy needle to enhance capture of a biopsy specimen by screwing the single helical thread into associated cancellous bone to capture a bone marrow specimen or bone marrow core. A mandrel may be used to wind the helical thread of a biopsy needle.

Another exemplary vertebral/medical procedure tray as set forth above may further comprise a bone marrow aspiration system having an aspiration needle set that may be releasably attached to the first end of a coupler assembly, operable to insert the aspiration needle set into a bone and associated bone marrow. The aspiration needle set may include a cannula having a single lumen and a trocar or stylet operable to be slidably disposed within the lumen of the cannula. The aspiration needle trocar or stylet may also be introduced into the same cannula as the other IO device/needle set of the tray. A medical and/or vertebral procedures tray may comprise an IO device and/or needle set for delivering a therapeutic agent (e.g., a bone cement, a pharmaceutical) to a bone; and a coupler assembly as set forth above, and optionally a biopsy needle set and/or an IO aspiration needle set.

The aspiration system and/or biopsy system trays may comprise containers to store the aspiration/biopsy samples and may also comprise suitable containers for sharp disposal. Medical procedure trays comprising aspiration systems and/or biopsy systems may be used in connection with detection of various bone diseases, including bone degenerative diseases, osteoporosis, fractures, bone cancers, detection of spread of metastatic cancers, detection of spread of infections, and other bone diseases.

In some embodiments, a medical procedure tray comprising an aspiration tray and/or a biopsy tray in addition to another IO device tray may be used to insert an IO needle comprising a cannula into a bone to provide access to bone; releasably inserting a biopsy and/or aspiration stylet or trocar to obtain a biological bone sample for analysis; releasably inserting another IO needle trocar into the same cannula to deliver a therapeutic agent in to the bone. In some aspects of this disclosure, a diagnostic test may be performed at the same time as a therapeutic procedure thereby reducing the need for multiple insertions of devices into bone and reducing trauma associated with such procedures.

Various teaching of the present disclosure may be used with other types of intraosseous devices and other types of medical procedures outside the field of providing bone or vascular access for treatment of a patient. Examples of such procedures may include, but are not limited to, placement of wires and screws associated with replacement of joints and internal fixation of bone fractures and many other orthopedic procedures. Teachings of the present disclosure may also be incorporated into various gastroenterology-urology biopsy devices and procedures. Therapeutic and diagnostic methods and devices of the disclosure may be used in both acute care and out-patient facilities.

Another aspect of the present disclosure may include a medical kit for diagnosis, evaluation and/or treatment of bone. In some embodiments, the present disclosure provides a vertebroplasty kit comprising an intraosseous needle set operable to penetrate vertebral bones and deliver surgical cement into the vertebral body. A kit of the disclosure may also include a biopsy system and/or an aspiration system and for simultaneously obtaining a biopsy and/or bone marrow sample of bone. A kit of the disclosure may comprise containers to store the biopsy/aspiration samples. A biological bone sample may be obtained from the same site as the site of delivery of therapeutic agent (e.g. cement) or may be obtained from a different site or a different bone.

A kit of the disclosure may also include one or more sharps containers. A coupler assembly, operable to be releasably coupled to a powered driver, the coupler assembly comprising a sterile container bag may be included. A coupler assembly may have a means disposed on a first end to releasably attach a powered driver to the coupler assembly and may have an additional means on a second end to releasably attach one or more intraosseous needles or biopsy needles to the coupler. A powered driver may be optionally provided with a kit of the disclosure or the kit may be usable with commercially available powered drivers. A kit may optionally comprise one or more surgical cements and/or therapeutic agents.

A further aspect of the present disclosure may include a biopsy kit along with an intraosseous procedure kit (for example, vertebroplasty kit), further having a biopsy needle and an ejector or ejector rod operable to remove a bone and/or bone marrow specimen from a biopsy needle. A funnel (sometimes referred to as an "ejector funnel") may also be included within the biopsy kit. The funnel may accommodate insertion of the ejector into one end of the biopsy needle. The funnel may include a reduced inside diameter portion formed in accordance with teachings of the present disclosure. For some embodiments, interior portions of the funnel may function as a "one way connector" which may allow the funnel to function as a sharps protector for one end of the biopsy needle disposed therein.

Each component of a kit of the disclosure may be packaged in one or more containers. In some embodiments, a kit may comprise one or more components in a first container and/or one or more components in a second container and so on. Several smaller containers may be comprised in a bigger container. Each container or the entire set of containers may be sealed by a paper or plastic covering.

Apparatus and methods incorporating teachings of the present disclosure may:

Reduced physical requirements to insert an IO device into bone and associated bone marrow.

Better control of an IO device during insertion.

Increased speed to complete an IO procedure.

Reduced discomfort to patients.

Simple, intuitive systems and procedures for an operator.

Multiple use of a non-sterile powered driver.

Availability of components to perform one or more medical procedures at the same time by providing components in a medical procedure tray and/or kit.

Kits with components for procedures such as vertebroplasty.

Kits that may further comprise components for biopsy and/or aspiration procedures and/or diagnostic and/or other therapeutic procedures.

Reduced requirement for multiple medical procedures, multiple insertions and multiple scheduling for patients.

This summary contains only a limited number of examples of various embodiments and features of the present disclosure. Additional examples of embodiments and features will be discussed in the Detailed Description of the Disclosure.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 3A is a schematic drawing showing an isometric view of a user attaching a non-sterile powered driver to a sterile coupler assembly attached to a sterile container bag in accordance with teachings of the present disclosure;

FIG. 3B is a schematic drawing showing still another isometric view of a user raising a sterile container bag of FIG. 3A with a flap and adhesive strip to enclose the non-sterile powered driver coupled with a sterile coupler assembly in accordance with teachings of the present disclosure;

FIG. 3C is a schematic drawing showing an isometric view of a non-sterile powered driver enclosed in a sterile container bag comprising a flap and an adhesive strip, wherein the powered driver is releasably coupled with a sterile coupler assembly and is further releasably attached to an intraosseous device assembly, in accordance with teachings of the present disclosure;

FIG. 6A is a schematic drawing showing an exploded of one example of an intraosseous needle incorporating teachings of the present disclosure;

FIG. 6B is a schematic drawing showing an isometric view of an intraosseous biopsy needle incorporating teachings of the present disclosure;

FIG. 6C is a schematic drawing showing an isometric view of another intraosseous needle incorporating teachings of the present disclosure;

DETAILED DESCRIPTION OF THE DISCLOSURE

Figure 1A:
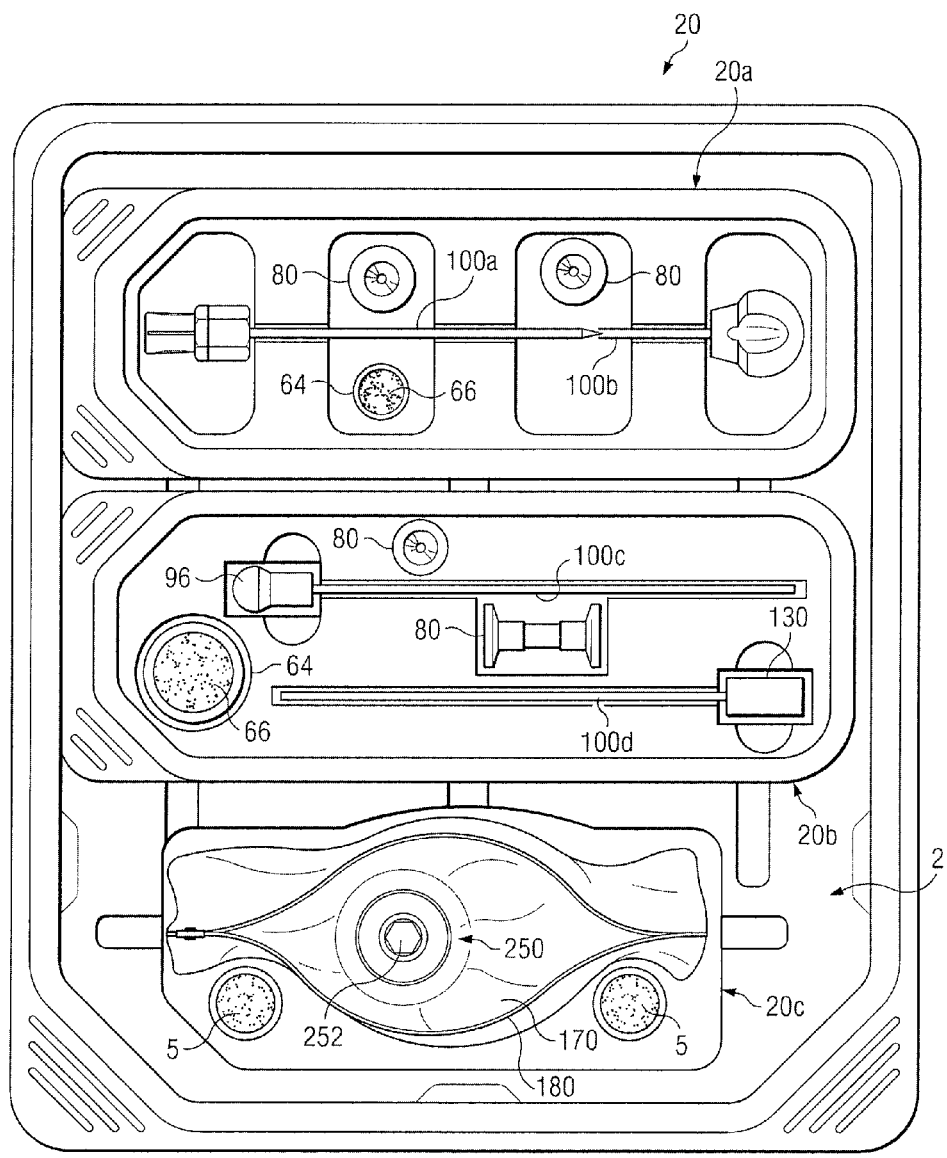
FIG. 1A is a schematic drawing showing a plan view of one example of a medical procedures tray comprising an intraosseous needle set and a biopsy needle set, each needle set disposed in a separate tray, and a coupler assembly operable to be releasably attached to each needle set and to a non-sterile medical device (e.g., a powered driver, not expressly shown), the coupler assembly further attached to a sterile container bag and disposed in another tray incorporating teachings of the present disclosure.

Apparatus, medical procedure trays, kits and methods incorporating teaching of the present disclosure may by used for diagnostic evaluation and/or for the treatment of various bone related ailments. Preferred embodiments of the disclosure and various advantages may be understood by reference to FIGS. 1A-10D, wherein like numbers refer to same and like parts.

In some embodiments, teachings of the present disclosure may be used for therapy and/or repair of fractures, such as but not limited to, vertebral fractures, or treatment of damaged bones in a patient's spine. Fractures of the spine are often due to osteoporosis, a progressive loss of bone tissue which depletes both collagen and calcium salts from bone. The bone tissue continues to weaken and is prone to fractures by cracking of the vertebral bones or by collapsing (compression) of the vertebral bones. People with osteoporosis rarely have any symptoms until the bone fractures occur. Vertebral compression fractures may also be caused by softening of bones due to aging or due to spreading of cancers to the vertebra or due to other cancers that can weaken bone. Compression of bony building blocks of the spine (vertebrae) causes a collapse of the vertebrae much like a sponge collapses under the pressure of one's hand. A fracture that collapses a spinal vertebra is called a vertebral compression fracture. Although in some instances vertebral compression fractures may occur without pain, these fractures often result in a severe "band-like" pain that radiates from the spine around both sides of the body. Over many years, spinal fractures reduce the height of the spine and the affected person becomes shorter. Conventional treatment of vertebral compression fractures includes pain medication, resting, avoiding injury, and using support braces. Therapies such as vertebroplasty, which involves stabilization of a fractured vertebral body by injection of a surgical cement, have been used to treat or ameliorate the symptoms associated with vertebral fractures.

Vertebroplasty is a non-surgical procedure, often performed by a radiologist, and involves inserting a surgical/bone cement into the center of the collapsed spinal vertebra in order to stabilize and strengthen the crushed bone. The surgical/bone cement is a glue-like material (such as poly-methylmethacrylate (PMMA)) and maybe typically inserted with a needle and syringe through anesthetized skin into the midportion of the vertebra under the guidance of specialized x-ray equipment. Upon insertion the cement hardens and forms a cast-like structure within the broken bone. The casting effect on the broken bone typically provides pain relief and the newly hardened vertebra protected from further collapse. Apart from pain relief, vertebroplasty allows better mobility to patients.

In some embodiments, the present disclosure provides medical devices, medical procedure trays, kits and methods for performing vertebroplasty or other procedures associated with spinal treatments. A medical procedure tray for performing vetrebroplasty and/or other spinal procedure may comprise an intraosseous (IO) device for penetrating vertebral bones such as an vertebral IO needle set, a coupler assembly, and a driver (manual or power driven) which may be non-sterile. The coupler assembly may comprise a containment bag or sterile glove that may be used to prevent direct contact of a non-sterile driver with a sterile IO device, operator and patient during a medical procedure. The coupler assembly may be operable to releasably engage an intraosseous device with portions of a drive shaft extending from one end of a powered driver, to obtain a device similar to that depicted in FIG. 3C or 4A. The coupler design allows for multiple use of a non-sterile driver for such procedures in conjunction with disposable sterile IO needle sets and couplers. The powered driver may be used to insert an intraosseous device at an insertion site (power in) and also allow the powered driver to "spin" the intraosseous device during removal from the insertion site (power out). An intraosseous needle set may comprise a cannula having a lumen and a trocar or a stylet operable to be slidably disposed within the lumen of the cannula.

A vertebroplasty method using the devices, kits or trays of the present disclosure may comprise: 1) penetrating a vertebral bone (fractured/compressed vertebral bone) using an intraosseous needle comprising a cutting tip and a cannula having a lumen using a powered driver and coupler assembly in a "power in" mode, the power driver suitably contained in a containment bag; 2) detaching the powered driver and coupler assembly from the IO needle inserted into the bone; 3) filling a trocar or stylet operable to be slidably disposed within the lumen of the cannula with surgical cement; 4) slidably disposing the trocar or stylet with surgical cement into the cannula; 5) injecting the surgical cement into the fractured bone; 6) detaching the trocar or stylet from the cannula; 7) reattaching the powered driver and coupler assembly to the cannula; and 8) withdrawing the cannula from the vertebral bone using the powered driver in a "power out" mode.

Typically a vertebroplasty procedure in accordance to the teachings of the disclosure, may utilize a bi-plane fluoroscopy imaging equipment to achieve accurate needle placement and delivery of accurate amounts of bone cement. Penetration of bone and depth of insertion of a needle may be guided by fluoroscopy or other imaging methods. In some embodiments, an operator may stop penetration when a decrease in resistance is felt, which may be indicative of passage through the hard cortex of bone into inner bone tissues. In some embodiments, for medical procedures that may require imaging or other visualization to guide an operator to insert an IO needle/device into a specific insertion site, hubs of the needle may be designed to be small and unobtrusive to the visualization method. For other embodiments one or more biopsy samples may be taken after inserting an intraosseous needle into a vertebral bone and prior to injecting cement and/or therapeutic agents into the vertebral bone.

Various spinal procedures or other medical procedures may be combined with suitable cleaning, disinfecting the insertion site prior to insertion of a needle. A patient may be locally or completely anesthetized based on the need. The site of insertion may be appropriately dressed and cared for after the procedure.

The term "containment bag" as used in this application may include any sterile sleeve, sterile envelope, sterile glove, sterile enclosure, sterile bag or any other device incorporating teachings of the present disclosure and operable to allow engaging a non-sterile device with a sterile device and conducting a medical procedure requiring a sterile field or sterile environment.

For some applications a non-sterile powered driver (or manual driver) may be placed in a containment bag incorporating teachings of the present disclosure and engaged with a sterile intraosseous device for use during various medical procedures requiring a sterile field or sterile environment. Such containment bags may be attached to a coupler assembly or any other device incorporating teachings of the present disclosure to prevent the non-sterile powered driver from contaminating the sterile intraosseous (IO) device during and after engagement of the non-sterile powered driver with the IO device.

The term "driver" as used in this application may include any type of powered driver (or manual driver) satisfactory for inserting an intraosseous (IO) device into a selected portion of a patient's bone. Such powered drivers often rotate a drive shaft extending therefrom. However, various teachings of the present disclosure may be used with powered drivers that reciprocate an associated drive shaft (not expressly shown).

Various techniques may be satisfactorily used to releasably engage or attach an IO device with a powered driver in accordance with teachings of the present disclosure. For example a wide variety of coupler assemblies, port assemblies, connectors, receptacles, fittings, hubs, hub assemblies, latching mechanisms and/or other types of connecting devices incorporating teachings of the present disclosure may be satisfactorily used to releasably engage an IO device with a powered driver.

Various types of coupler assemblies incorporating teachings of the present disclosure may be satisfactorily used to releasably engage one end of a shaft extending from a driver with one end of an intraosseous device. For some embodiments the powered driver may include a drive shaft having one end with a generally hexagonal cross section operable to be releasably engaged with a latch mechanism disposed in one end of a coupler assembly. For some embodiments a coupler assembly incorporating teachings of the present disclosure may be referred to as a "hands free" coupler, a quick disconnect or quick release coupler and/or port assembly.

Respective latch mechanisms may be disposed proximate a first end and a second end of a coupler assembly in accordance with teachings of the present disclosure. Pushing one end of a drive shaft extending from a powered driver into the second end of the coupler assembly may result in an annular recess disposed in the one end of the drive shaft "snapping" into releasable engagement with the respective latch mechanism. Pushing one end of an intraosseous device into the first end of the coupler assembly may result in an annular recess in the one end of the intraosseous device "snapping" into releasable engagement with the respective latch mechanism.

For some embodiments, a coupler assembly or port assembly may be engaged with a containment bag or sterile sleeve in accordance with teachings of the present disclosure. Coupler assemblies and/or hub assemblies incorporating teachings of the present disclosure allow easy separation of an associated powered driver from an IO device such that the IO device may remain in place in a patient to allow bone marrow aspiration or removal of bone and/or bone marrow biopsy specimens. Such coupler assemblies and/or port assemblies may also allow an associated powered driver to "spin" or rotate an attached IO device while withdrawing an IO device from an insertion site or changing the depth of penetration of an IO device in a target area. Rotating the IO device during withdrawal or changing depth (power out) may substantially improve patient comfort and reduce potential trauma to bone and soft body tissue proximate an insertion site.

A powered driver may be used to insert an IO device incorporating teachings of the present disclosure into a selected target area or target site in ten seconds or less. However, various teachings of the present disclosure are not limited to use with powered drivers. Manual drivers and spring powered drivers may also be used with IO devices incorporating teachings of the present disclosure.

Examples of manual drivers are shown in copending patent application Ser. No. 11/042,912 entitled Manual Intraosseous Device filed Jan. 25, 2005 (now U.S. Pat. No. 8,641,715).

The term "fluid" may be used in this application to include liquids such as, but not limited to, blood, water, saline solutions, IV solutions, plasma or any mixture of liquids, particulate matter, dissolved medication and/or drugs associated with biopsy or aspiration of bone marrow or communication of fluids with bone marrow or other target sites. The term "fluid" may also be used in this patent application to include any body fluids and/or liquids containing particulate matter such as bone marrow and/or cells which may be withdrawn from a target area.

The terms "harvest" and "harvesting" may be used in this application to include bone and/or bone marrow biopsy and bone marrow aspiration. Bone and/or bone marrow biopsy (sometimes referred to as "needle biopsy") may be generally described as removing a relatively small piece or specimen of bone and/or bone marrow from a selected target area for biopsy purposes. Bone marrow aspiration (sometimes referred to as "bone marrow sampling") may be generally described as removing larger quantities of bone marrow from a selected target area. Relatively large quantities of bone marrow may be used for diagnostic, transplantation and/or research purposes. For example some stem cell research techniques may require relatively large quantities of bone marrow.

The terms "insertion site," "penetration site," and "installation site" may be used in this application to describe a location on a bone at which an intraosseous device may be inserted or drilled into the bone and associated bone marrow. Insertion sites, penetration sites and installation sites are generally covered by skin and soft tissue. For example, for a vertebral procedure an insertion site may be a vertebral disc bone.

The term "intraosseous (IO) device" may be used in this application to include, but is not limited to, any hollow needle, hollow drill bit, penetrator assembly, bone penetrator, catheter, cannula, trocar, stylet, inner penetrator, outer penetrator, IO needle, biopsy needle, aspiration needle, IO needle set, biopsy needle set or aspiration needle set operable to penetrate and/or provide access to an intraosseous space or interior portions of a bone. Such IO devices may be formed, at least in part, from metal alloys such as 304 stainless steel and other biocompatible materials associated with needles and similar medical devices.

Various types of IO devices may be formed in accordance with teachings of the present disclosure. Examples of such IO devices may include, but are not limited to, IO needle sets for delivering therapeutic agents, IO needle sets for delivering a bone cement, vertebral IO needles, biopsy needles, biopsy needle sets, aspiration needles and aspiration needle sets. However, a wide variety of other IO devices may be formed in accordance with one or more teachings of the present disclosure. Such IO devices may or may not include a trocar and/or a stylet.

For some applications, a trocar and/or a stylet may be inserted into a generally hollow, longitudinal bore or lumen in an associated catheter or cannula. The first end of the second hub may be releasably engaged with second end of the first hub to releasably dispose the stylet or trocar within the longitudinal bore of the cannula or catheter. The present disclosure is not limited to IO needle sets such as therapeutic agent delivery IO needle sets, vertebral IO needles, aspiration needle sets, or biopsy needle sets as discussed in this application.

The term "target area" may be used in this application to describe selected portions of a bone cavity or locations in a bone cavity into which a therapeutic agent may be delivered or from which associated bone tissue and/or bone marrow may be harvested in accordance with teachings of the present disclosure.

Many currently available techniques for providing a therapeutic agent and obtaining a bone sample and/or harvesting bone and/or bone marrow may require more than one penetration into a bone and associated bone marrow to retrieve an adequate sample of bone and/or bone marrow. Separate diagnostic and therapeutic procedures are normally required even for diagnosis and therapy to the same bone, thereby requiring multiple insertions into the same bone at different times.

Further, multiple penetration sites may be required in the same bone if a biopsy specimen is not satisfactorily retrieved at the first penetration site. Medical personnel may need to insert an IO needle into several different penetration sites on the same bone to obtain adequate quantities of bone marrow for transplant or stem cell research. For example obtaining sufficient quantities of bone marrow from a patient's pelvis may require six or more insertion sites. Multiple insertions may be extremely painful for a patient and may deter some people from donating bone marrow. Multiple insertions may also cause fatigue in medical personnel performing such procedures with manual IO devices. Multiple scheduling for therapeutic procedures separate from diagnostic procedures also adds to trauma and cost for a patient.

For some applications, an IO needle or other IO device may be formed with a first end operable to penetrate bone and/or associated bone marrow. A connector or hub may be attached to a second end of the IO needle or other IO device. Such connectors or hubs may be operable to releasably engage the IO needle or IO device with a powered driver, a manual driver and/or a coupler assembly.

IO needle sets and other IO devices incorporating teachings of the present disclosure may include a first IO device such as a cannula, catheter or outer penetrator and a second IO device such as a stylet, trocar, syringe, or inner penetrator. Various types of cutting surfaces may be formed proximate a first end of the first IO device and a first end of the second IO device. The cutting surface of the first IO device and the cutting surface of the second IO device may cooperate with each other to penetrate bone and/or associated bone marrow.

A first connector or first hub may be used to releasably engage the first IO needle or IO device with the second IO needle or IO device. For example an IO needle set may include a first connector or a first hub with a generally hollow cannula, catheter or outer penetrator attached thereto and extending from a first end of the first hub. A second end of the first hub may be operable to be releasably engaged with a first end of a second connector or a second hub. A stylet, trocar or inner penetrator may also be attached to and extend from the first end of the second hub. The second end of the first hub may include an opening sized to allow inserting the stylet, trocar or inner penetrator through the opening and a lumen in the cannula, catheter or outer penetrator.

A second end of the second hub may be operable to be releasably engaged with a first end of a coupler assembly incorporating teachings of the present disclosure. One end of a shaft extending from a powered driver or a manual driver may be releasably engaged with a second end of the coupler assembly.

In some embodiments of the present disclosure, the dimensions of the hubs may be designed to be unobtrusive or minimally obtrusive to an imaging method that may be used to image the site of insertion and a medical procedure being performed such as the delivery of a medicament to a specific site.

Additional details concerning powered drivers, connectors, hubs, and IO devices may be found in co-pending patent application entitled "Powered Driver Intraosseous Device and Methods To Access Bone Marrow," Ser. No. 12/061,944, filed Apr. 3, 2008, which claims priority from a provisional patent application with the same title filed on Apr. 4, 2007.

Various features of the present disclosure may be described with respect to powered driver 200, coupler assemblies 250 and 250*a*, hub assemblies 130 (130*a*, 130*b*, 130*c* and 130*d*), hubs, 96, 140, 150, IO needle sets 100, 100*a*, 100*b*, 100*c* and 100*d*, including IO needles, vertebral needles, IO biopsy needles, IO aspiration needles, and containment bag 170.

However, the present disclosure is not limited to such powered drivers, coupler assemblies, hub assemblies, IO needle sets, and/or containment bags. A wide variety of intraosseous devices, hub assemblies, coupler assemblies and/or containment bags may be formed in accordance with teachings of the present disclosure with various dimensions and/or configurations.

Figure 1B:
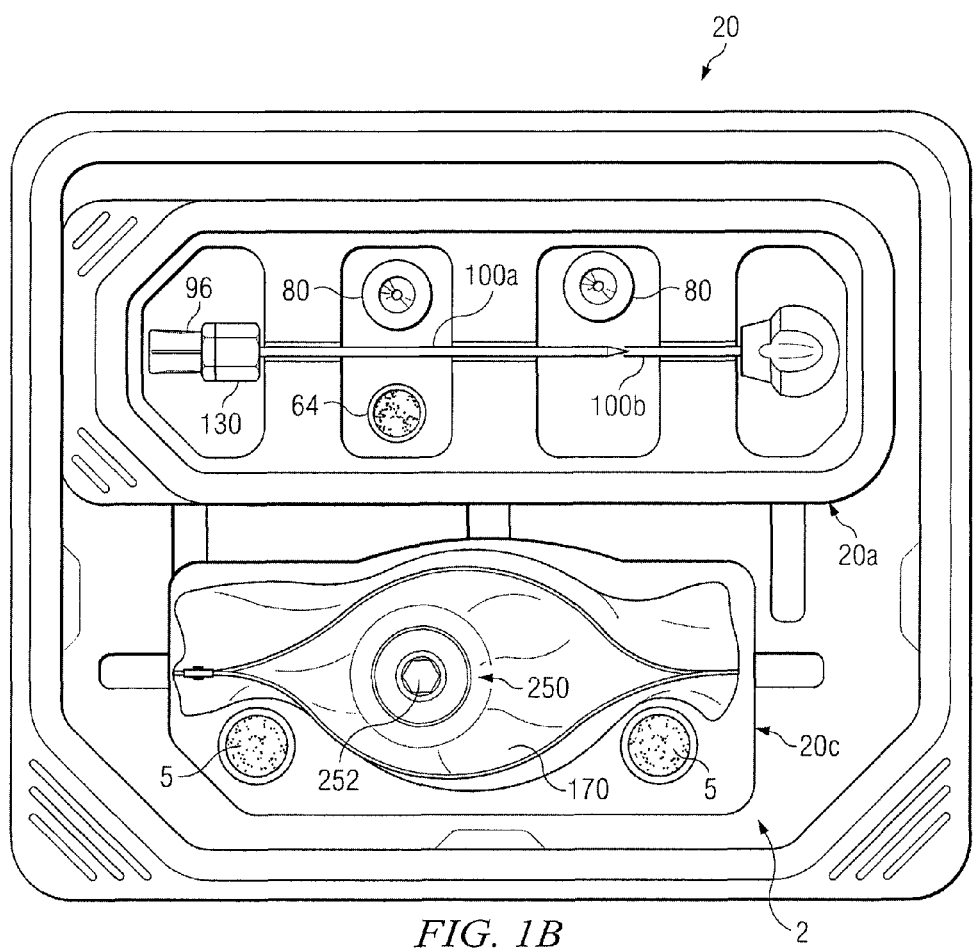
FIG. 1B is a schematic drawing showing a plan view of one example of a medical procedures tray comprising an intraosseous needle set enclosed in a tray and a coupler assembly operable to be releasably attached to the needle set and to a powered driver (not shown), the coupler assembly further attached to a sterile container bag incorporating teachings of the present disclosure.

FIGS. 1A and 1B show some examples of medical procedure trays and/or kits which may contain one or more intraosseous devices and/or other components incorporating teachings of the present disclosure. For example, medical procedure tray 20 as shown in FIG. 1A may include a first tray 20a comprising an intraosseous needle set with needles 100a and 100b (e.g., an IO needle set for penetration and delivery of a medicament to a vertebral bone), funnel 80 and sharps container 64; a second tray 20b comprising an intraosseous biopsy needle set with needles 100c and 100d, funnel 80 and sharps container 64 incorporating various teachings of the present disclosure; and a third tray 20c comprising a coupler assembly 250, containment bag 170, feet 5 and second end of the coupler assembly 252 that may be releasably attached to power driver 200 (not expressly shown). Feet 5 provide support for tray 20c. Trays 20a, 20b and 20c may be enclosed in tray 20 and covered with a detachable paper or plastic wrap 2. In some embodiments, an additional tray comprising an IO aspiration system for obtaining bone marrow may also be comprised in tray 20 (not expressly depicted).

For delivery of a therapeutic agent to bone and/or for removal of a biological specimen from a bone the needles 100b or 100d as depicted in FIGS. 1A and 1B may also be referred to as an "ejector rod." An ejector rod, such as 100b or 100d, may be slidably disposed into a hollow cannula 100 of an IO needle to deliver a medicament or obtain a biological sample from a bone. In the case of a biopsy ejector rod, a helical thread, operable to be wound back by a mandrel, may be disposed in the cannula. Upon contact with bone tissue the helical thread may be would back to retrieve the biopsy sample.

The length of ejectors 100b or 100d may be selected to be greater than the length of a lumen in an associated IO needle. Handle or hub 96 may be disposed on second end 92 of ejectors 100b or 100d. See FIG. 1D. The dimensions and configuration of first end 91 of ejector rod 100b or 100d may be selected to be compatible with inserting first end 91 through an opening in the first end 111 of an associated IO and/or biopsy needle 100. Various types of ejectors, ejector rods, funnels and/or ejector funnels may also be used with an IO needle, a vertebral needle, an IO biopsy needle, IO aspirator needle and/or other intraosseous devices incorporating teachings of the present disclosure.

Medical procedure tray 20 as shown in FIG. 1B may include first tray 20a comprising an intraosseous needle set 100a and 100b (for example, vertebral IO needles), funnels 80 and sharps container 64; and second tray 20c comprising a coupler assembly 250, containment bag 170, feet 5 and second end of the coupler assembly 252 that may be releasably attached to power driver 200 (not expressly shown). IO needle sets 100 may comprise one or more cannulas, stylets, trocars, and/or cutting needle tips. Feet 5 provide support for tray 20c. Trays 20a, 20b and 20c may be enclosed in tray 20 and covered with a detachable paper or plastic wrap 2.

Medical procedure trays and/or kits formed in accordance with teachings of the present disclosure may provide a support or base for various components such as one or more of the following: IO devices and needles 100, coupler assembly 250, funnel 80 and/or sharps protector 64 to allow an operator or user to perform various functions without requiring that the operator or user hold or manipulate the respective component. For example medical procedure tray 20c as shown in FIGS. 1A and 1B may position and support coupler assembly 250 such that one end of a powered driver 200 may be inserted (pushed) into releasable engagement with second end 252 of coupler assembly 250. The powered driver 200 may then be used to withdraw coupler assembly 250 from medical procedure tray 20c without requiring an operator or user to directly hold or manipulate coupler assembly 250.

Figure 1C:
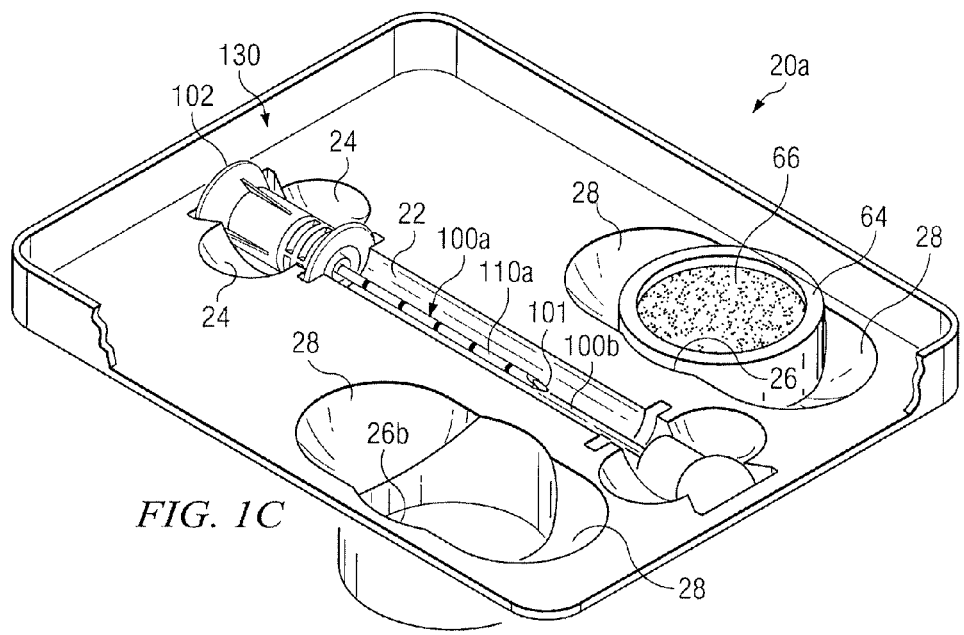
FIG. 1C is a schematic drawing showing an isometric view of one example of a medical procedures tray comprising an intraosseous needle set depicting details of the tray incorporating teachings of the present disclosure.
Figure 1D:
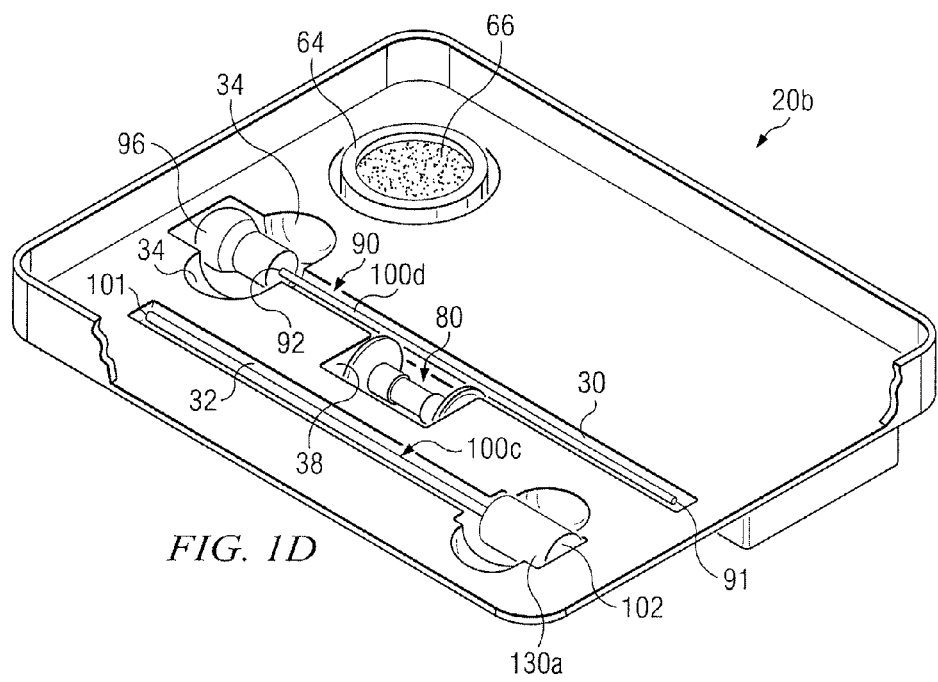
FIG. 1D is a schematic drawing showing an isometric view of one example of a medical procedures tray comprising an intraosseous biopsy needle set depicting details of the tray incorporating teachings of the present disclosure.
Figure 1E:
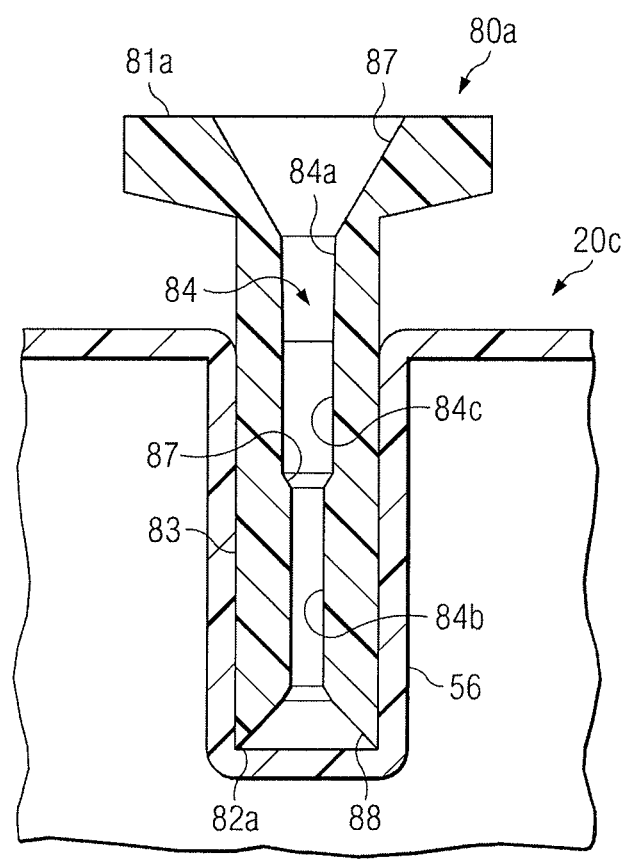
FIG. 1E is a schematic drawing in section with portions broken away showing one example funnel of a medical procedures tray incorporating the teachings of the present disclosure.

FIG. 1E depicts a detailed structure of funnels 80 of FIGS. 1A, 1B, 1C and 1D. Funnel 80a, as in FIG. 1E, may be positioned and supported within medical procedure trays 20a or 20b such that one end of an intraosseous device may be inserted (pushed) into funnel 80a. Funnel 80a may be withdrawn from medical procedure tray 20a and/or 20b without requiring that an operator or user directly hold or manipulate funnel 80a.

Funnel 80a may be slidably disposed in holder 56 in medical procedure tray 20a in a generally vertical position. See FIGS. 1A, 1B, 1C and 1D. As a result, first end 81a of funnel 80a may be oriented in a position to allow inserting one end of IO biopsy needles such as the cannula depicted herein as 100a or 100c therein. Longitudinal passageway 84 proximate first end 81a may include a sticking tapered portion operable to maintain contact with one end of an IO set such as the outer cannula 100a or 100c. An IO needle set or cannula may then be manipulated to pull funnel 80a from holder 56. Funnel 80a may serve as a sharps protector for the one end of an intraosseous device inserted therein.

For some applications, funnels formed in accordance with teachings of the present disclosure may include a respective first opening formed at a first end and a respective second opening at a second end of the funnel. The first opening and the second opening may have different inside diameters. For example, the first opening may be sized to accommodate inserting an IO needle, a vertebral needle and/or a biopsy needle therein while the second opening may have a reduced inside diameter which prevents inserting the needle therein. The second opening may be sized to only accommodate one end of an associated ejector rod. For some applications, a longitudinal passageway may extend between the first end and the second end of the funnel. Tapered surfaces may be formed within the longitudinal passageway adjacent to the first end. The tapered surfaces may function as a "one way" connector such that when an IO needle, a vertebral needle, and/or an IO biopsy needle is inserted therein, the funnel will be securely engaged with the first end of the needle. The funnel may then function as a sharps protector for the first end of the needle.

Each sharps protector 64 may also be positioned and supported within medical procedure trays 20a and/or 20b to allow inserting (pushing) one end of an intraosseous device or any other medical device requiring sharps protection into sharps protector 64 without requiring that an operator or user to directly hold or manipulate the associated sharps protector 64. Medical procedure trays 20, 20a, 20b 20c, coupler assemblies 250 and other components formed in accordance with teachings of the present disclosure may substantially reduce the number of opportunities for an accidental "needle stick" and/or dropping, contaminating or other problems associated with handling and manipulating various components disposed within an associated medical procedure tray.

Medical procedure trays and kits formed in accordance with teachings of the present disclosure may have a wide variety of configurations and/or dimensions. For some applications, a kit holding intraosseous devices in accordance with teachings of the present disclosure may have an overall length of approximately four and one-half inches, a width of approximately three inches and a depth of approximately two inches. Various heat sealing techniques may be satisfactorily used to place a removable cover (not expressly shown) over a medical procedure tray or kit incorporating teachings of the present disclosure.

Sharps protectors 64 may include hard foam or claylike material 66 disposed therein. Intraosseous devices such as vertebral needle sets, other IO needle sets, aspiration needle sets and biopsy needle sets typically have respective sharp tips and/or cutting surface operable to penetrate skin, soft tissue and bone. The sharp tips and/or cutting surface of such intraosseous devices may be inserted into hard foam or claylike material 66 after completion of a medical procedure using the respective intraosseous device.

For some applications, medical procedure tray 20 or 20a may be referred to variously as a "vertebral procedure tray," and/or "vertebroplasty tray," and/or a "tray for providing access to deliver therapeutic agents to bone," and/or a "therapeutic and diagnostic procedures tray." For some applications, medical procedure tray 20b may sometimes be referred to as "bone and/or bone marrow biopsy procedure trays" or "biopsy procedure trays" or "bone marrow biopsy kits." For some applications, medical procedure tray 20a may be referred to as a "bone marrow aspiration tray," "aspiration procedure tray" or "bone marrow aspiration kit". For some applications, medical procedures tray 20c may be referred to as "coupler assembly tray" or "sterile glove tray."

Medical procedure trays 20a, 20b and/or 20c may be formed from various polymeric materials compatible with sterile packaging and storage of various components disposed within each medical procedure tray. For some applications ethylene oxide sterilization techniques may be used during assembly and packaging of medical procedure trays 20a, 20b and 20c. However, other sterilization procedures may be used as appropriate.

In some embodiments, medical procedures trays of the disclosure may be stored at temperatures ranging from between about −20° C. to about 50° C.

Respective covers (not expressly shown) may be placed over each medical procedure tray 20a, 20b and 20c as part of an associated sterilization and packaging process. Such covers may be removed prior to use of various components disposed within each medical procedure tray. A respective cover 2 may be placed on the main tray 20 that comprises two or more of trays 20a, 20b and/or 20c.

Medical procedure tray, vertebroplasty tray, vertebral procedure tray, diagnostic and therapeutic tray, or tray for providing a medicament to a bone, 20a (see FIG. 1C) may include elongated slot 22 with appropriate dimensions for an associated intraosseous device such as, but not limited to, IO needle set 100, or 100a and 100b. The dimensions and configuration of slot 22 may be selected to accommodate the combined length of hub assembly 130 and cannula 110a extending therefrom. One end of slot 22 may be sized to accommodate the dimensions and configuration of hub assembly 130. Enlarged openings or finger slots 24 may also be provided to accommodate inserting and removing IO needle set 100 from slot 22. Various details associated with IO needle set 100 will be discussed later with respect to FIG. 6A-8E.

In FIGS. 1C and 1D, sharps protector 64 may be disposed within holder 26 of medical procedure tray 20a or 20b. A pair of finger slots 28 may also be formed in tray 20a or 20b to accommodate inserting and removing sharps protector 64 from holder 26a. Holder 26b may also be formed in tray 20a along with associated finger slots 28. An additional sharps protector or other components may be disposed within holder 26b. The dimensions/configurations of slot 22 and holders 26a and 26b may be varied as desired for respective components which will be disposed therein.

Medical procedure trays 20b (See FIG. 1D) may include elongated slots 30 and 32. The dimensions and configuration of elongated slot 30 may be selected to accommodate placing ejector 110d therein. The dimensions and configuration of elongated slot 32 may be selected to accommodate placing an intraosseous device such as a biopsy system with biopsy needle set 100c and 100d therein (as depicted) or an aspiration system with an aspiration needle (not depicted).

One end of elongated slot 30 may have configuration and dimensions selected to accommodate the configuration and dimensions of handle 96 disposed on second end 92 of injector rod 100d (See FIG. 1D). A pair of finger slots 34 may be formed as part of elongated slot 30 to allow installing and removing ejector 100d. One end of elongated slot 32 may be operable to accommodate the configuration and dimensions associated with hub assembly 130a of IO biopsy needle set 100c. A pair of finger slots 36 may also be provided as part of elongated slot 32 to accommodate inserting and removing IO biopsy needle set 100c from elongated slot 32.

Tray 20b may also include holder 38 disposed adjacent to elongated slot 30. Holder 38 may have a configuration and dimensions compatible with releasably placing funnel 80 therein. One or more specimen or sample containers or cups (not expressly shown) may be provided in biopsy tray 20b. Biopsy specimen or sample containers may include a cavity sized to receive a biopsy specimen from biopsy needle set 100c and 100d. Funnel holders 38 may be formed in biopsy procedure tray 20b adjacent to ejector 100d to ensure that funnel 80 is readily available to assist with removing a biopsy specimen from biopsy needle set 100d.

Figure 2A:
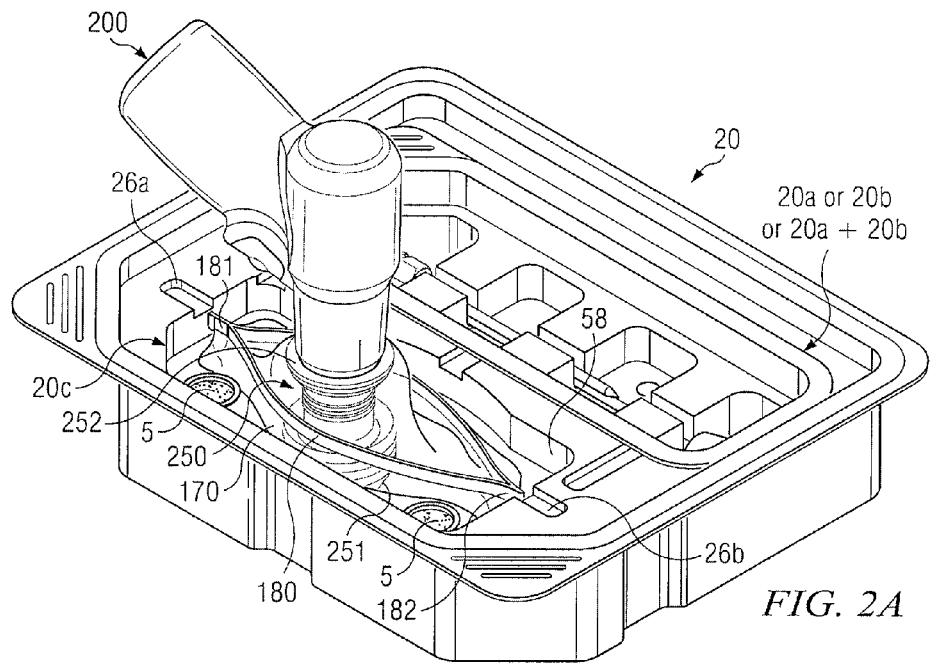
FIG. 2A is a schematic drawing showing an isometric view of one example of a medical procedure tray that may include an intraosseous needle set and/or a biopsy needle set enclosed, each optionally enclosed in a separate tray, and a coupler assembly attached to a sterile container bag disposed in another tray, the coupler operable to be releasably attached to a powered driver (one example of a non-sterile medical device) as depicted in accordance with teachings of the present disclosure.
Figure 2B:
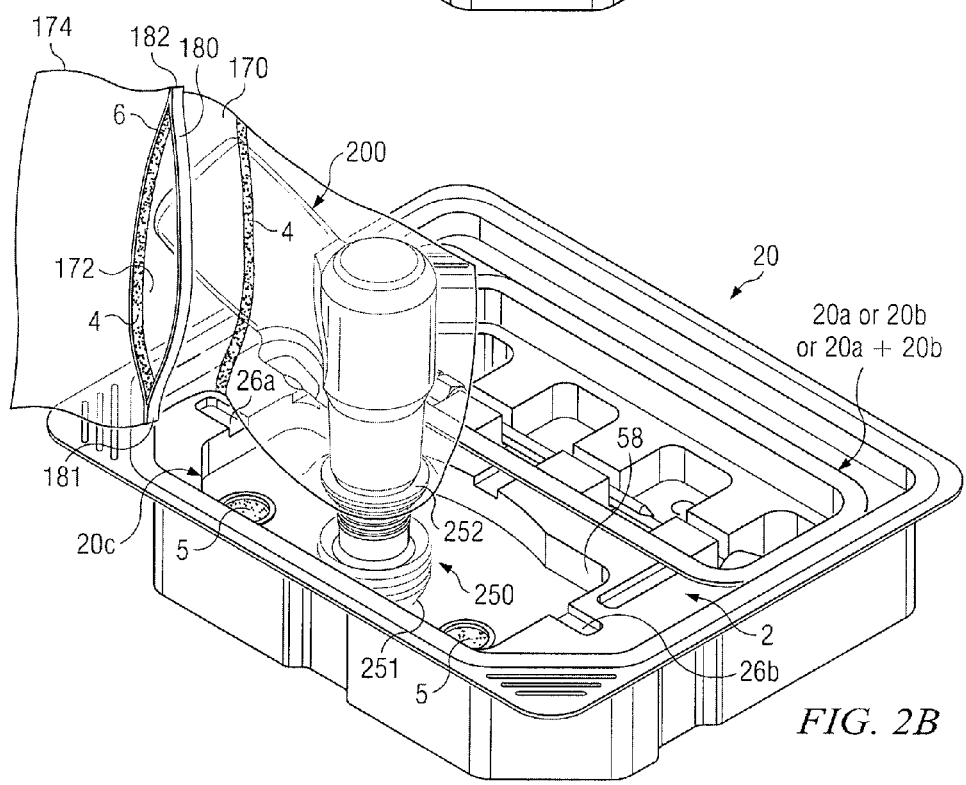
FIG. 2B is a drawing of a medical procedures tray showing one example of a sterile container bag with a non-sterile powered driver disposed therein and the driver attached releasably to a sterile coupler assembly in accordance with teachings of the present disclosure.

Medical procedure trays 20 as shown in FIGS. 2A and 2B represent other example of a medical procedure tray formed in accordance with teachings of the present disclosure. FIGS. 2A and 2B depict trays that comprise medical procedure tray 20c and either trays 20a and 20b; or 20c and 20a or 20b. Containment bag 170 and power driver 200 are also shown. FIG. 2B shows power driver 200 being enclosed in containment bag 170. Containment bag 170 may comprise a flexible stay 180, a flap 174, and may further comprise an adhesive strip 4 all of which may be used to contain a non-sterile power driver 200 and prevent contamination of IO devices, IO needles or coupler by the non-sterile power driver. Containment bag 170 may also prevent contamination of the power driver 200 by pathogens in bodily fluids that may leak out during a medical procedure. The configuration and dimensions of flexible stay 180 may be selected to accommodate inserting and removing a powered driver or other non-sterile medical device therefrom.

A combined medical procedure tray(s) (such as 20 in FIG. 1A or 20 in FIG. 1B) may be sterilized after being assembled. One benefit of such sterilization may include, but is not limited to, providing a sterilized containment bag which may be used to engage a non-sterile medical device with a sterile medical device in accordance with teachings of the present disclosure.

One of the benefits of the present disclosure may include being able to releasably engage one end 211 of a powered driver 200 with one end 252 of a coupler assembly 250, releasably engage one end 102 of an IO needle 100 (such as a vertebral needle or a biopsy needle) with an opposite end 251 of the coupler assembly 250, insert "power in" another end 101 of the IO needle 100 into a selected target area, deliver one or more medicaments into the target area using one or more components of an IO device or needle set 100, "power out" the IO needle 100 with a high degree of confidence that a specimen (such as a biopsy sample) will be disposed therein and insert the other end 101 of the IO needle into a funnel to provide both sharps protection and removal/storage of the specimen. Any direct contact between an operator and the IO needle may be limited to pushing one end of the IO needle into a respective end of the coupler assembly.

Another benefit of the present disclosure is to insert "power in" a first IO needle (such as a cannula) into a bone to provide access to the bone followed by slidably inserting a second IO needle (such as a trocar) into the first IO needle. The second needle may be operable to deliver a therapeutic agent to bone or may be operable to obtain a specimen from bone. The second needle may be slidably removed from the first IO needle. In one example, a second needle may be a biopsy needle that may be inserted into the cannula of a first needle to obtain a biopsy and slidably removed after the sample is obtained. Another needle, a third IO needle (a trocar) operable to deliver a therapeutic agent may then be slidably inserted into the first needle (cannula) and a therapeutic agent may be delivered. Multiple needles may be inserted for different diagnostic/therapeutic purposes repeatedly through the first cannula needle without the need for multiple insertions into bone. Upon completion of the medical procedures the first needle may then be "powered out". In some embodiments, the medical procedure devices and trays and methods of the present disclosure may be used to perform multiple procedures with one insertion into the bone.

A pair of holders or clamps 26, 26a, 26b (FIGS. 2A and 2B) may also be formed in medical procedure tray 20c adjacent to holder for coupler assembly 250. Such clamps 26a and 26b may be designed to respectively accommodate first end 181 and second end 182 of flexible stay 180 disposed on opening 172 of containment bag 170. Coupler assembly 250 may also be installed in holder 58 of coupler assembly tray 20c with first end 251 down and second end 252 looking up. FIGS. 2A and 2B shows a power driver 200 being placed on second end 252 of a coupler assembly 250 in exemplary tray 20, where exemplary tray 20 comprises tray 20c as described above and may comprise trays 20a and 20b or tray 20a or may even comprise a tray 20d (not depicted). FIG. 2B depicts a raised bag 170 covering powered driver 200, showing features of the containment bag 170 including flap 174, opening 172, flexible stay 180, respective ends 181 and 182 of the flexible stay, and adhesive strip 4 in an exemplary medical procedures tray as described earlier in this paragraph. However, the present disclosure is not limited to using flaps and adhesive materials to close an opening in a containment bag and other means may be used to close and seal a containment bag.

FIGS. 3A-3C illustrate one procedure for placing a powered driver 200 within containment bag 170 incorporating teachings of the present disclosure. Containment bag 170 may be formed from generally flexible, fluid impervious material such as a plastic, which may also be sterilized using conventional sterilization techniques. Containment bag 170 may be used to prevent a non-sterile powered driver 200 from contaminating a sterile intraosseous device 100 and/or a patient, particularly during an IO therapeutic and/or IO diagnostic procedure. Containment bag 170 may be operable to form a fluid barrier with adjacent portions of housing assembly 270 of coupler assembly 250. At the same time, coupler assembly 250 may allow powered driver to rotate an intraosseous device 100 releasably engaged with first end 251 of coupler assembly 250 without damage to containment bag 170.

A non-sterile person (not expressly shown) may next insert power driver 200 into coupler assembly 250 and extend containment bag 170 (FIGS. 3A-3C). First end 181 and second end 182 of flexible stay 180 may be removed from respective clamps or holders in medical procedure tray 20c to allow manually lifting second opening 172 upwardly relative to powered driver 200. See FIGS. 2A-2B and 3A-3C. Containment bag 170 may continue to be raised to a fully extended position with powered driver 200 disposed therein. See FIG. 3B. Flap 174 may then be placed over second opening 172 and further sealed using the adhesive strip 4 proximate 172. Containment bag 170 with powered driver 200 disposed therein and coupler assembly 250 may then be removed from holder 58 of medical procedure tray 20c (FIGS. 2A-2B). Various commercially available low strength adhesive materials may be satisfactorily used to provide releasable engagement between flap 174 proximate opening 172 of containment bag 170.

Housing assembly 270 and/or housing segments 280 and 290 of coupler assembly 250 may remain relatively stationary during rotation of elongated core 260. In some embodiments, spinner 10 may be rotated for insertion and securing of IO device at end 251. See FIGS. 3A-3C and 4A-4B. For example portions of housing assembly 270 such as flange 254 extending from second end 252 of coupler assembly 250 may be attached to containment bag 170 and remain relatively stationary while powered driver 200 rotates elongated core 260 and IO needle set 100 extending therefrom.

For some applications, powered driver 200 may be directly placed into a containment bag 170 and engaged with coupler assembly 250. For other applications, a non-sterile powered driver may be inserted into containment bag 170 in connection with removing coupler assembly 250 from a medical procedure tray.

For some applications, a protective cover (not expressly shown) may be removed from medical procedure tray 20c. End 224 extending from drive shaft 222 of powered driver 200 may then be inserted through opening 172 of containment bag 170 and releasably engaged with second end 252 of coupler assembly 250 (see FIG. 4C and FIGS. 3A-3C).

Typical procedures associated with using a medical procedure tray or kit incorporating teachings of the present disclosure may include the following steps. Medical procedure tray 20 may be placed at a desired location for performing an associated medical procedure. For example medical procedure tray 20 may be placed on a table or cart adjacent to a surgical table on which a bone therapeutic procedure, a vertebral procedure, a bone or bone marrow biopsy procedure, and/or a bone marrow aspiration procedure may be performed.

An associated cover 2 may be removed from medical procedure tray 20 by a sterile person. A non-sterile person may then pick up and insert non-sterile powered driver 200 into flexible stay 180 such as shown in FIG. 3A. End 224 of drive shaft 222 of powered driver 200 may "snap" into place within second end 252 of coupler assembly 250. A sterile person may then lift containment bag 170 up and over powered driver 200 (as shown in FIG. 3B), and fold flap 174 over to secure with adhesive strip 4 which will result in containing the power driver 200 (not expressly shown).

The sterile person may then grasp handle 214 of powered driver 200 through containment bag 170 and lift powered driver 200 with coupler assembly 250 attached thereto from holder 58 disposed in tray 20c. The sterile person may then remove an intraosseous (IO) device/needle 100 from medical procedure trays 20a or 20b and insert second end 102 of IO device/needle 100 into first end 251 of coupler assembly 250.

A "snap" may be felt when second end 102 of IO device/ needle 100 (or any other intraosseous device incorporating teachings of the present disclosure) is releasably latched within first end 251 of coupler assembly 250. A needle safety cap (not expressly shown) may be removed from first end 101 of IO needle 100 after releasably engaging second end 102 with first end 251 of coupler assembly 250.

Powered driver 200 disposed within containment bag 170 along with coupler assembly 250 and IO needle 100 extending there from may be held in one hand while a sterile person identifies the insertion site with the other hand. Powered driver 200 may be positioned over the insertion site to introduce first end 101 of IO needle set 100 through the skin in the direction and towards the bone. Upon contact with the bone the operator may squeeze button or trigger 246 and apply relatively steady gentle pressure to handle 214 of powered driver 200. Upon penetration of the bone cortex, the operator may release trigger 246 to stop further insertion of first end 101 of IO needle 100.

First housing segment 280 may then be activated to release second end 102 of IO needle 110a from engagement with coupler assembly 250. Second hub 150a may then be rotated counterclockwise to disengage second hub 150a and associated stylet 120 from first hub 140a. See FIGS. 5A-5B and 6A-6C. Stylet 120 may then be pulled out and removed from IO needle or cannula 111a. First end 121 of stylet 120 (FIG. 6C) may then be inserted into sharps protector 64 of medical procedure tray 20. Upon completion of an appropriate IO procedure second hub 150a may be reengaged with first hub 140a (see FIGS. 6A and 6B). First end 251 of coupler assembly 250 may then be reengaged with second end 102 of IO needle set 100a to rotate or spin IO needle set 100a while withdrawing from the insertion site. After removal from the insertion site, second end 102 of IO needle set 100a may be disengaged from coupler assembly 250. First end 101 of IO needle set 100a may then be inserted into sharps container 64.

In general, after completion of a bone related medical procedure, such as vertebroplasty, other spinal procedures, delivery of a medicament to a bone, a bone marrow aspiration procedure, a bone and/or bone marrow biopsy procedure and/or other medical procedures using an IO device 100, the sharp end or sharp tip of all components of the intraosseous device may be inserted into material 66 in sharp protector 64 for further disposal in accordance with the appropriate procedures.

Powered driver 200 as shown in FIGS. 3A-3C, and 4A-4C may be satisfactorily used to insert an intraosseous device incorporating teachings of the present disclosure into a bone and associated bone marrow. However the disclosure is not limited to this particular power driver and any power driver may be used to practice the present embodiments.

Powered driver 200 may include housing 210 having a general configuration similar to a small pistol defined in part by handle 214. Various components associated with powered driver 200 may be disposed within housing 210 including handle 214. For example a power source such as battery pack 216 may be disposed within handle 214. Battery pack 216 may have various configurations and dimensions. Battery pack may comprise a lithium chloride battery.

Housing 210 including handle 214 may be formed from relatively strong, heavy duty polymeric materials such as polycarbonates or other satisfactory materials. For some applications housing 210 may be formed in two halves (not expressly shown) which may be joined together with a fluid tight seal to protect various components of powered driver 200 disposed therein.

Motor 218 and gear assembly 220 may be disposed within portions of housing 210 adjacent to handle 214. Motor 218 and gear assembly 220 may be generally aligned with each other. Motor 218 may be rotatably engaged with one end of gear assembly 220. Drive shaft 222 may be rotatably engaged with and extend from another end of gear assembly 220 opposite from motor 218. For some applications both motor 218 and gear assembly 220 may have generally cylindrical configurations.

Motors and gear assemblies satisfactory for use with powered driver 200 may be obtained from various vendors. Such motor and gear assemblies may be ordered as "sets" with one end of each motor securely attached to an adjacent end of an associated gear assembly. A drive shaft having various dimensions and/or configurations may extend from the gear assembly opposite from the motor. Such gear assemblies may sometimes be referred to as "reduction gears" or "planetary gears". The dimensions and/or configuration of housing 210 may be modified to accommodate an associated motor and gear assembly.

Distal end or first end 211 of housing 210 may include an opening (not expressly shown) with portions of drive shaft 222 extending therefrom. For some applications end 224 or the portion of drive shaft 222 extending from first end 211 of housing 210 may have a generally hexagonal cross section with surfaces 226 disposed thereon. Receptacle 263 disposed in second end 252 of coupler assembly 250 may have a matching generally hexagonal cross section. See FIGS. 5A-5B.

Surfaces 226 may extend generally parallel with each other and parallel with respect to a longitudinal axis or rotational axis (not expressly shown) associated with drive shaft 222. One or more tapered surfaces 228 may also be formed on end 224 to assist with releasably engaging powered driver 200 with coupler assembly 250. See FIGS. 5A-5B. The end of a drive shaft extending from a powered driver may have a wide variety of configurations.

A drive shaft having desired dimensions and configuration may extend from the gear assembly opposite from the motor. The drive shaft may be provided as part of each motor and gear assembly set. The dimensions and/or configuration of an associated housing may be modified in accordance with teachings of the present disclosure to accommodate various types of motors, gear assemblies and/or drive shafts. For example, powered drivers used with vertebral IO needles, aspiration needles and/or biopsy needles may include gear assemblies with larger dimensions required to accommodate larger speed reduction ratios, for example between 60:1 and 80:1, resulting in slower drive shaft RPM's. Powered drivers used to provide intraosseous access during emergency medical procedures may operate at a higher speed and may include gear assemblies having a smaller speed reduction ratio, for example between 10:1 and 30:1, resulting in higher drive shaft RPM's. For some applications, the difference in size for gear assemblies may result in increasing the inside diameter of an associated housing by approximately two to three millimeters to accommodate larger gear assemblies associated with powered drivers used to insert vertebral IO needles, biopsy needles and/or aspiration needles.

Coupler assemblies having corresponding openings or receptacles may be releasably engaged with end 224 extending from first end 211 of powered driver 200 or end 224a extending from first end 211 of powered driver 200a. For example, end 224 extending from first end 211 of housing 210 may be releasably engaged with receptacle 264 disposed proximate second end 252 of coupler assembly 250 as shown in FIGS. 1A-1B, 2A-2B, 3A-3C and 5A-5D.

For some applications thrust bearing 241 may be disposed between first end or distal end 211 of housing 210 and adjacent portions of gear assembly 220. See FIG. 4C. Thrust bearing 242 may be disposed between second end or proximal end 212 of housing 210 and adjacent portions of motor 218. Thrust bearings 241 and 242 may limit longitudinal movement of motor 218, gear assembly 220 and drive shaft 222 within associated portions of housing 210.

Trigger assembly 244 may also be disposed within housing 210 proximate handle 214. Trigger assembly 244 may include trigger or contact switch 246. See FIG. 4C. Motor 218 may be energized and deenergized by alternately depressing and releasing trigger 246. Electrical circuit board 247 may also be disposed within housing 210. Electrical circuit board 247 may be electrically coupled with trigger assembly 244, motor 218, power supply 216 and indicator light 248.

For some applications indicator light 248 may be a light emitting diode (LED) or a small more conventional light bulb. For some applications indicator light 248 may be activated when ninety percent (90%) of electrical storage capacity of battery pack 216 has been used.

The configuration and dimensions of an intraosseous device formed in accordance with teachings of the present disclosure may vary depending upon respective intended applications for each intraosseous device. For example, the length of a vertebral IO needle formed in accordance with teachings of the present disclosure may vary from approximately about 5 inches to about 10 inches. In one non-limiting example a vertebral IO needle may be about 6 inches (or 152 millimeters). However, vertebral needles with other lengths may also be made in accordance with the teachings of this disclosure.

The length of a biopsy needle formed in accordance with teachings of the present disclosure may vary from approximately five (5) millimeters to thirty (30) millimeters. However, biopsy needles having other lengths may also be formed in accordance with teachings of the present disclosure.

Aspiration needles formed in accordance with teachings of the present disclosure may have lengths of approximately twenty five (25) millimeters, sixty (60) millimeters and ninety (90) millimeters. For some applications an aspiration needle having a length of ninety (90) millimeters or more may also include one or more side ports. See for example FIGS. 6A-6C.

Further details about IO biopsy systems and needle sets and IO aspirations systems may be found in co-pending U.S. patent application Ser. No. 11/853,678 filed on Sep. 11, 2007 (073252.0204).

Intraosseous (IO) devices formed in accordance with teachings of the present disclosure may have outside diameters and longitudinal bores or lumens corresponding generally with eighteen (18) gauge to ten (10) gauge needles. For example, a vertebral IO needle may have a cannula with an eight (8) gauge to eleven (11) gauge diameter while an biopsy needle that may be inserted inside the vertebral cannula may have a diameter of fifteen (15) gauge to sixteen (16) gauge. The configuration and dimensions of each IO device may depend upon the size of an associated bone and desired depth of penetration of associated bone marrow. In one specific non-limiting example, a vertebral IO needle set may comprise a beveled cutting tip and a stylet and may be an 11 gauge, 152 millimeter needle, made of 304 stainless steel.

Combining a powered driver with a coupler assembly and a vertebral needle set in accordance with teachings of the present disclosure may allow rapid access to the vertebral or spinal bones or other insertion sites. Vertebral access systems incorporating teachings of the present disclosure may be capable of inserting a vertebral needle to a desired depth in cancellous bone in ten (10) to fifteen (15) seconds. This same capability may be used to obtain bone marrow using the bone marrow aspiration systems as well as biopsy specimen of bone and/or bone marrow using the biopsy needles of the present disclosure.

Intraosseous (IO) needle sets, such as vertebral IO needles 100a and 100b, biopsy needles 100c and 100d and aspiration needle 100e as shown in FIGS. 1A-1B and/or FIGS. 6A-6C represent only some examples of intraosseous devices formed in accordance with teachings of the present disclosure. All the IO needles may have similar outer penetrators or cannulas 110a and similar inner penetrators to stylets 120. See FIGS. 6A-6C. Similar or different hub assemblies 130 or 130a may be used.

For embodiments represented by IO needle sets 100 and 100a, first end 111a of cannula 110a and first end 121 of stylet 120 may be operable to penetrate a bone and/or associated bone marrow. Various features of first end 111a of cannula 110a and first end 121 of stylet 120 are shown in more detail in FIGS. 7A-7F. First end 101 of IO needle sets 100 and 100a may correspond generally with first end 111a of cannula 110a and first end 121 of stylet 120.

Cannula 110a may have a plurality of markings 104 disposed on exterior portions thereof. Markings 104 may sometimes be referred to as "positioning marks" or "depth indicators." Markings 104 may be used to indicate the depth of penetration of the IO needle set 100 or 100a into a bone (e.g. vertebral bone) and/or associated bone marrow. For some applications cannula 110a may have a length of approximately sixty (60) millimeters and may have a nominal outside diameter of approximately 0.017 inches corresponding generally with a sixteen (16) gauge needle. In some applications, a cannula 110a may be an 8-11 gauge needle and an inner trocar such as a biopsy or cement trocar may be a 15-16 gauge needle. Cannula 111a may be formed from stainless steel or other suitable biocompatible materials. Positioning marks 104 may be spaced approximately one (1) centimeter from each other on exterior portions of cannula 110a.

Hub assembly 130 as shown in FIGS. 6A-6C may be used to releasably dispose stylet 120 within longitudinal bore or lumen 118 of cannula 110a. Hub assembly 130 may include first hub 140 and second hub 150. The second end of cannula 110a, opposite from first end 111a, may be securely engaged with the second end of cannula 110a. The second end of stylet 120, opposite from first end 121, may be securely engaged with the first end of hub 150.

As shown in FIG. 6A cannula 110a may extend longitudinally from first end 141 of hub 140. Stylet 120 may also extend from the first end of hub 150 (not expressly shown). The second end of hub 140 may include a standard Luer lock fitting which may be releasably engaged with a corresponding Luer lock fitting disposed within the first end of second hub 150. Threaded connections may be present between the second end of first hub 140 and the first end of second hub 150 (not expressly shown). Examples of Luer lock connections and/or fittings are shown in more detail in FIGS. 6A-6C. The Luer lock fitting disposed on the second end of hub 140 may be operable to be releasably engaged with a standard syringe type fitting and/or a standard intravenous (IV) connection.

Hub 150 includes second end 152 which generally corresponds with second end 132 of hub assembly 130 and second end 102 of IO needle set 100. Hub 140 may include first end 141 which may generally correspond with first end 131 of hub assembly 130. Cannula 110a may extend longitudinally from first end 141 of hub 140 and first end 131 of hub assembly 130.

Figure 4A:
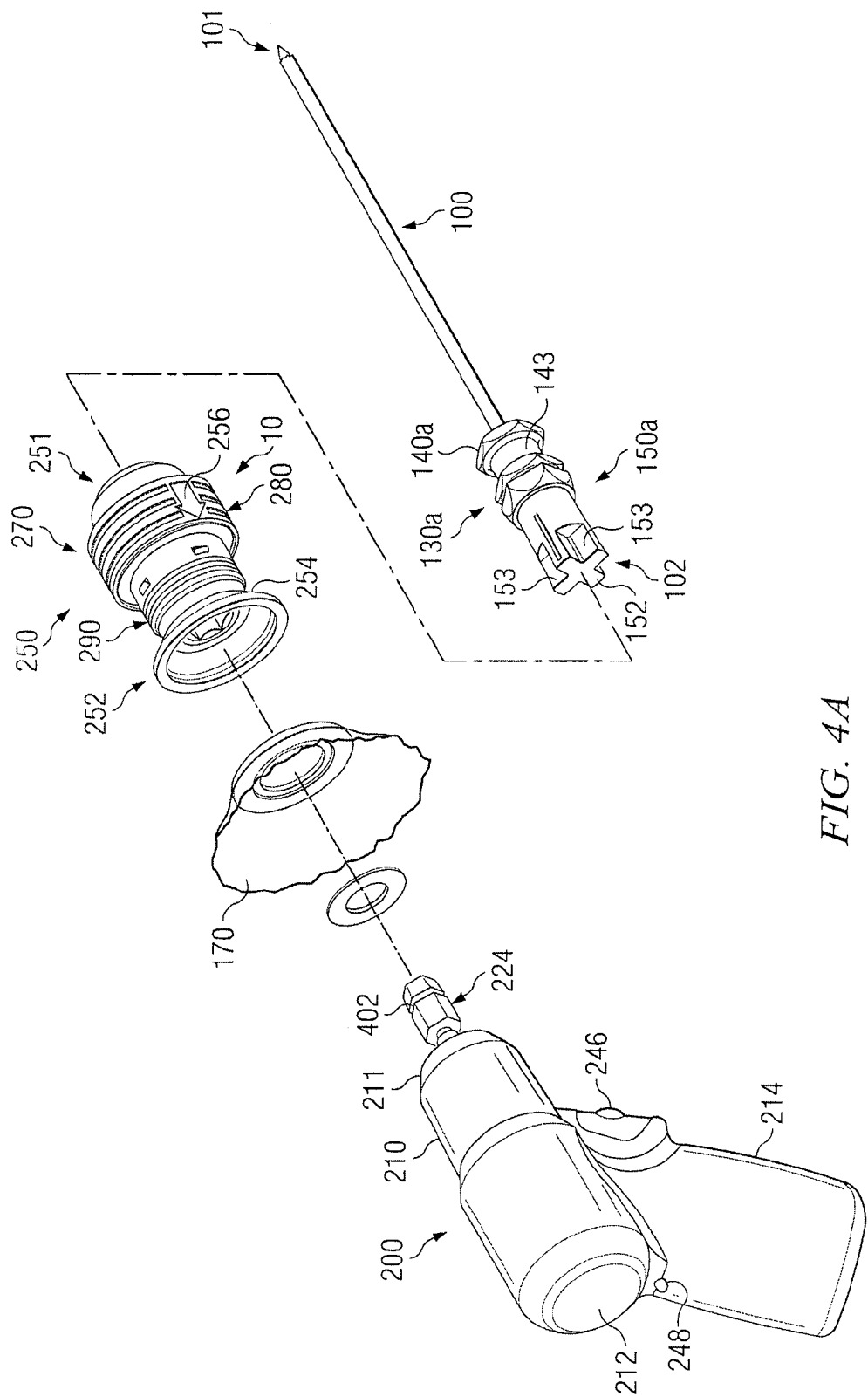
FIG. 4A is a schematic drawing showing an exploded, isometric view of a powered driver, coupler assembly with a sterile bag and an intraosseous device incorporating teachings of the present disclosure.
Figure 4B:
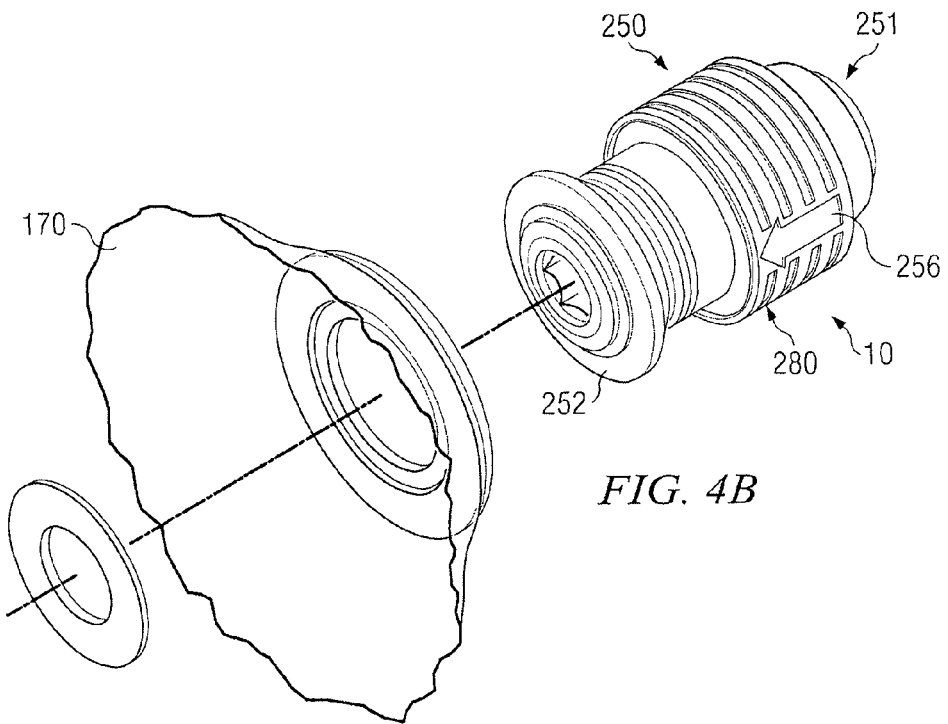
FIG. 4B is a schematic drawing showing another exploded, isometric view of the coupler assembly with the sterile bag of FIG. 4A incorporating teachings of the present disclosure.
Figure 4C:
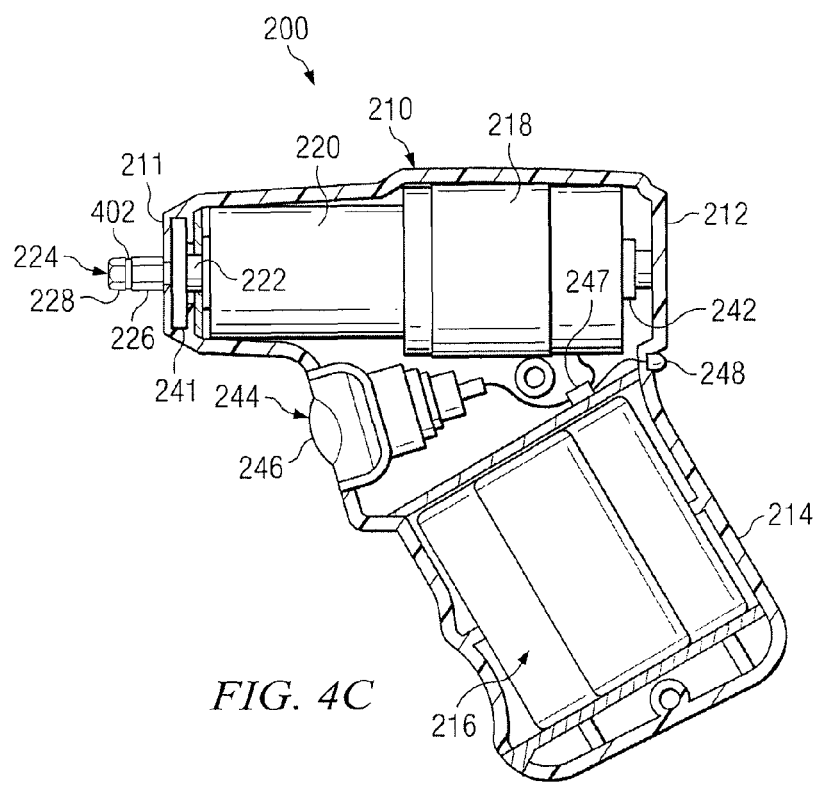
FIG. 4C is a schematic drawing showing one example of a powered driver operable for use with intraosseous (IO) devices incorporating teachings of the present disclosure.

Various types of receptacles may be satisfactory disposed in second end 152 of hub 150 for use in releasably engaging hub assembly 130 with a powered driver. For example, a receptacle having a generally tapered configuration corresponding with the tapered configuration of one end of a drive shaft extending from a powered driver may be releasably engaged with second end 152 of hub 150. Powered driver 200 as shown in FIGS. 4A-4C may represent one example of a powered driver having a drive shaft extending from a housing with a tapered portion operable to be releasably engaged with a receptacle having a corresponding generally tapered configuration. For some applications such powered drivers may be secured to an intraosseous device by a magnet (not expressly shown) disposed on the end of the tapered shaft extending from the powered driver and a metal disk disposed within a corresponding receptacle in the intraosseous devices. Such powered drivers may also be used with intraosseous devices used to obtain emergency vascular access (EVA).

Figure 5A:
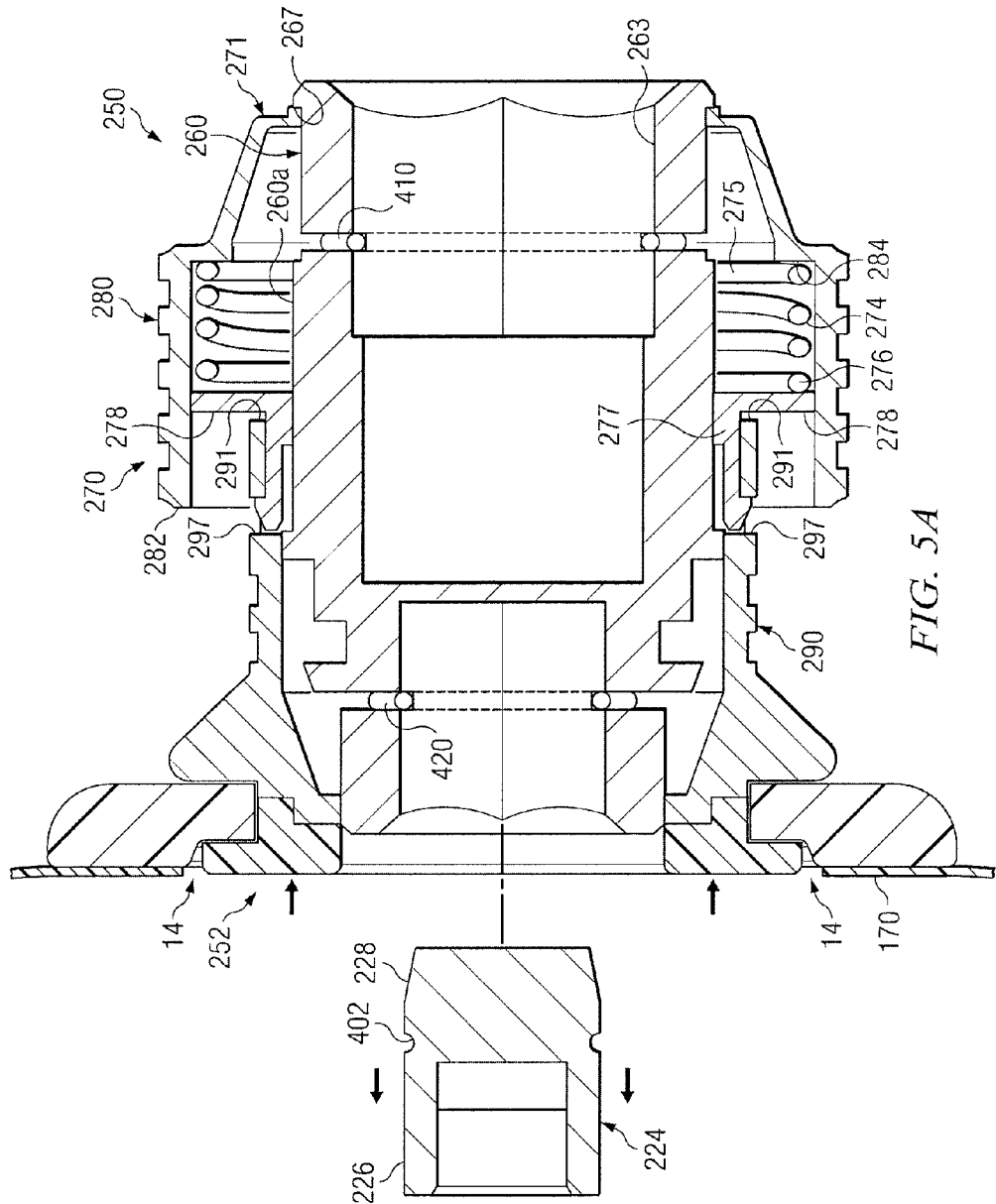
FIG. 5A is a schematic drawing in section with portions broken away showing a coupler assembly such as in FIGS. 4A and 4B in a second position showing release of a powered driver from a receptacle disposed in the first end of the coupler assembly and showing attachment of a sterile containment bag and a tortuous path disposed proximate attachment site of containment bag, incorporating the teachings of the present disclosure.
Figure 5B:
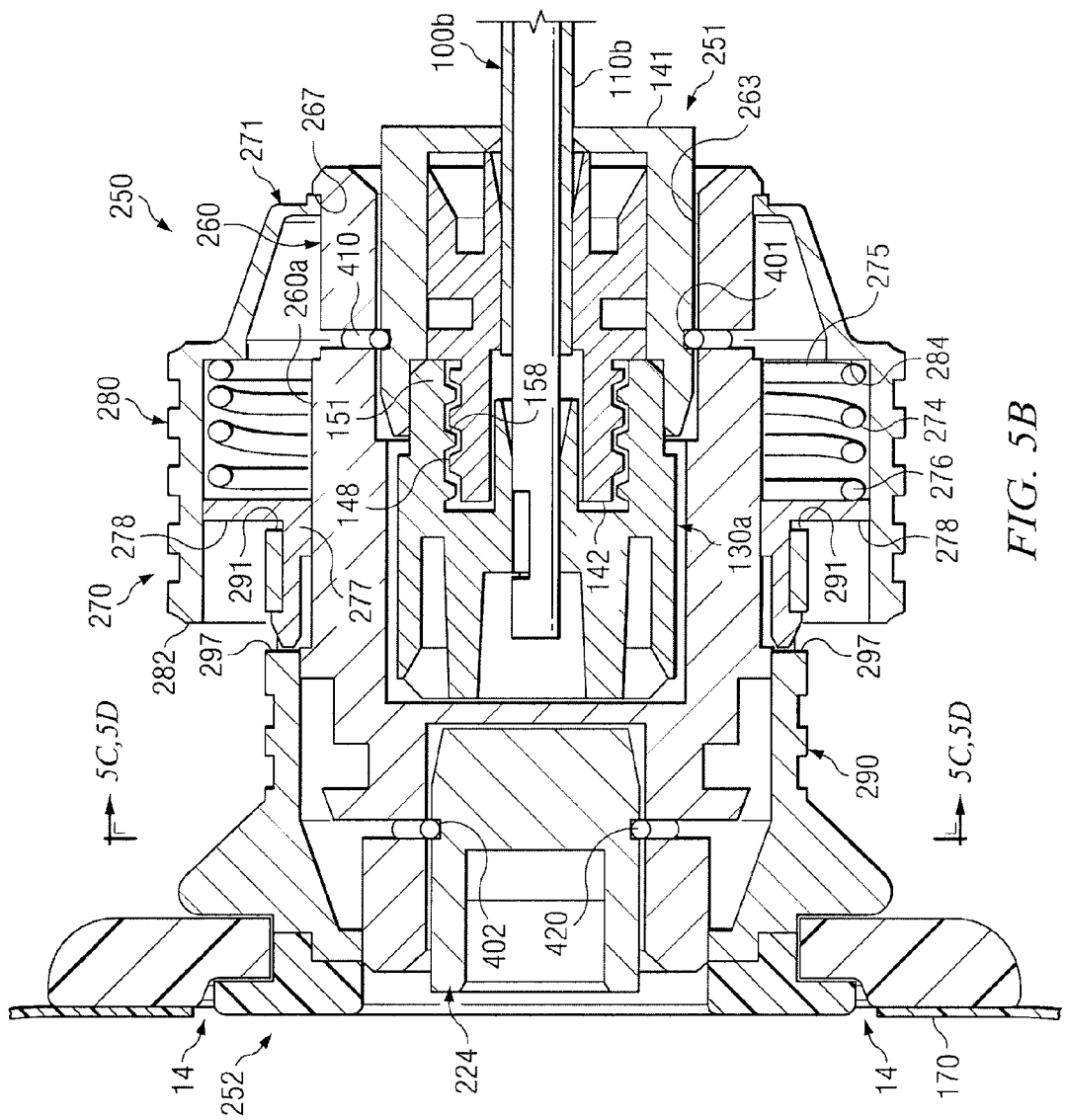
FIG. 5B is a schematic drawing in section with portions broken away showing another example of a coupler assembly incorporating teachings of the present disclosure.

The coupler assembly as depicted in FIGS. 5A and 5B depicts how containment bag 170 is attached to the coupler. Containment bag 170 is attached proximate end 252 of the coupler. In some embodiments, the containment bag may be attached using a hot glue gun. However, a wide variety of attachment mechanisms such as but not limited to coupler assemblies, port assemblies, connectors, receptacles, fittings, hubs, hub assemblies, latching mechanisms and/or other types of connecting devices incorporating teachings of the present disclosure may be satisfactorily used to attach the container bag with the coupler assembly.

A "tortuous path" 14 is defined proximate attachment of bag 170 and the body of the coupler. A tortuous path 14 may be a non-linear path such that bodily fluids that may contain bacteria, viruses or other pathogens cannot easily traverse to cause contamination of a sterile IO device attached at end 251 of the coupler. A tortuous path may comprise sharp curves. If a pathogen falls into a part of the torturous tortuous path the sharp curves and edges prevent the pathogen from reaching sterile surfaces on the other side.

For other embodiments, the second end of a hub assembly may be operable to be disposed within a receptacle formed in a coupler assembly incorporating teachings of the present disclosure. One feature of the present disclosure may include forming a hub assembly which may be releasably engaged within a first receptacle disposed in a first end 251 of a coupler assembly 250. See for example receptacle 263 proximate first end 261 of elongated core 260 as shown in FIG. 5A-5D. The dimensions and configuration of receptacle 263 may be selected to prevent rotation of hub 150a relative to hub 140a while inserting (rotating) an IO device into a bone and associated bone marrow. The powered driver may be releasably engaged with a second receptacle disposed in a second end 252 of the coupler assembly. See for example receptacle 264 proximate second end 262 of elongated core 260 as shown in FIGS. 5A-5B.

At least one portion of hub assembly 130a may have a generally hexagonal cross section operable to be received within the generally hexagonal cross section of receptacle 264 disposed proximate first end 251 of coupler assembly 250. See FIGS. 5C and 5D. For some applications portions of first hub 140a disposed adjacent to reduced outside diameter portion 143 may have generally hexagonal cross sections. See FIGS. 6A and 6B. Various cross sections other than hexagonal may be satisfactorily used to releasably engage a powered driver with one end of a coupler assembly and an intraosseous device with an opposite end of the coupler assembly.

Aspiration needle sets may often include a trocar, stylet or penetrator in combination with an associated cannula, catheter or outer penetrator. However, biopsy needles formed in accordance with teachings of the present disclosure may or may not include a trocar, stylet or inner penetrator. For example, biopsy needle 100c is shown in FIG. 6B attached to first end of hub 140a. A stylet or inner penetrator is not attached to first end 151 of hub 150a.

For embodiments represented by biopsy needle 100c, hub 140a may be used to releasably engage biopsy needle 100c in a receptacle formed in a coupler assembly incorporating teachings of the present disclosure. Hub 150a may be attached to close of end 141 of hub 140a. However, for many applications hub 140a without hub 150a may be connected with one end of a coupler assembly in accordance with teachings of the present disclosure. Biopsy needle 100c may be used to capture a biopsy specimen of a bone and associated bone marrow. Placing a trocar within biopsy needle 100c may result in substantial damage to the bone specimen during penetration of the bone by the combined tips of the trocar and biopsy needle 100c.

Hub 140a may include second end 142 with opening 144 formed therein. Passageway 146 may extend from second end 142 towards first end 141 of hub 140a. Passageway 146 may be operable to communicate fluids with lumen 118 of cannula 100a. See FIGS. 6A-6C and FIGS. 7A-7F. Second end 142 of hub 140 may include various features of a conventional Luer lock connection or fitting, including threads 148. Corresponding threads 158 may be formed within first end 151 of hub 150a. The dimensions and configuration of receptacle 263 in first end 251 of coupler assembly 250 may be selected to prevent relative movement between hub 140a and hub 150a during insertion (rotation) of an IO device into a bone and associated bone marrow. If such relative movement occurs, threads 148 and 158 may be disconnected.

For some applications hub 140a and hub 150a may be formed using injection molding techniques. For such embodiments hub 140a may include reduced outside diameter portion 143 disposed between first end 141 and second end 142. In a similar manner a plurality of void spaces or cutouts 153 may be formed in hub 150a adjacent to and extending from second end 152 in the direction of first end 151. See for example FIGS. 6A, 6B and 4A. The configuration and dimensions of reduced diameter portion 143 and/or cutouts 153 may be varied to optimize associated injection molding techniques and at the same time provide required configurations, dimensions and material strength to allow associated hub assembly 130a to function in accordance with teachings of the present disclosure.

Figure 7A:
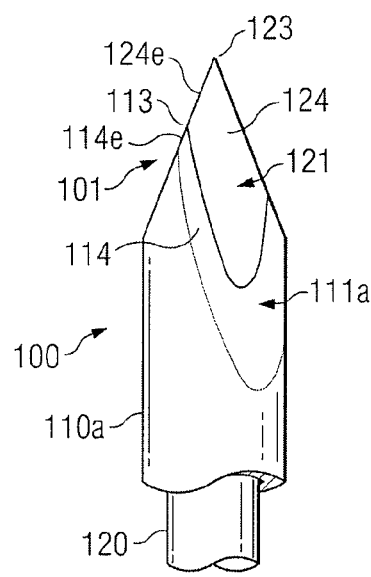
FIG. 7A is a schematic drawing showing an exploded view with portions broken away of the tips of an intraosseous needle set incorporating teachings of the present disclosure.
Figure 7B:
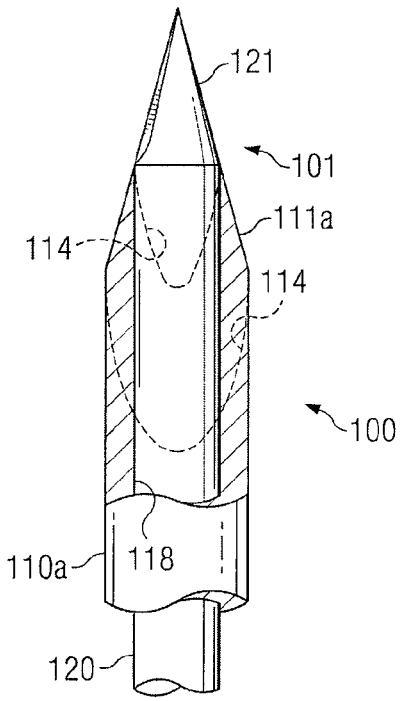
FIG. 7B is a schematic drawing showing an exploded view with portions broken away of a beleved tip of an intraosseous needle set incorporating teachings of the present disclosure.

FIGS. 7A and 7B show one example of cutting surfaces and tips which may be formed adjacent to the ends of a cannula and an associated trocar in accordance with teachings of the present disclosure. For embodiments represented by cannula or outer penetrator 110a and trocar or inner penetrator 120a, tip 123 of stylet 120 may be disposed relatively close to tip 113 of cannula 110a. For some applications, first end 121 of trocar 120 and first end 111a of cannula 110a may be ground at the same time to form adjacent cutting surfaces 114 and 124. Grinding ends 111a and 121 at the same time may result in forming a single cutting unit to form generally matching cutting edges 124e and 114e such as shown in FIGS. 7A and 7B. Beveled cutting surfaced and/or serrated cutting surfaces may be used in some embodiments. Other types of cutting surfaces formed in accordance with teachings of the present disclosure may be discussed later.

First end 121 of trocar 120 may extend through opening 144 in second end 142 of hub 140a. See FIG. 6A. Hub 150a disposed on the second end of trocar 120 may be releasably engaged with the second end of cannula 110*a* represented by hub 140*a*. See FIG. 6B.

Human bones may generally be described as having a hard outer lamellae or layer of osseous tissue known as "cortical bone". Cancellous bone (also known as trabecular or spongy bone) typically fills an inner cavity associated with cortical bone. Cancellous bone is another type of osseous tissue with generally low density and strength but high surface area. Cancellous bone typically includes spicules or trabeculae which form a latticework of interstices filled with connective tissue or bone marrow. Exterior portions of cancellous bone generally contain red bone marrow which produces blood cellular components. Most of the arteries and veins of a bone are located in the associated cancellous bone.

One of the benefits of the present disclosure may include providing various vertebral intraosseous devices including, but not limited to, vertebroplasty needles, vertebral biopsy needle sets configured to reliably provide a therapeutic agent and adapted to obtain biopsy specimens of cortical bone and/or cancellous bone by reducing need for multiple procedures/insertions in a patient.

The configuration of the tip of a cannula or outer penetrator may be modified in accordance with teachings of the present disclosure to provide optimum torque during insertion of the cannula or outer penetrator by a powered driver to penetrate bone for a therapeutic or diagnostic procedure. A controlled, steady feed rate when using a powered driver may result in higher quality delivery of therapeutic agent (cement) and/or obtaining biopsy specimens as compared to manually inserted IO needles. A needle comprising a beveled cutting tip, such as a stylet may be used to initially penetrate bone. The cutting tip may be retractable and withdrawn after insertion of a cannula comprising the beveled cutting tip. A rod shaped needle/cannula, containing one or more therapeutic agents (such as but not limited to a bone cement), configured to inject the therapeutic agent, may be disposed within the hollow cannula that has a tip making contact with the interior of the bone. In embodiments wherein a biopsy sample is desired, a biopsy rod/trocar may also be inserted into the hollow cannula. A biopsy rod may have a helical thread disposed within proximate an associate tip or first end to assist with capturing a bone and/or bone marrow biopsy specimen.

The quality and reliability of a medical procedure incorporating teachings of the present disclosure may be substantially improved by using an optimum feed rate for inserting and IO needle into a bone and associated bone marrow. Feed rate or speed of insertion of an IO biopsy needle incorporating teachings of the present disclosure may be a function of the pitch of at least one thread disposed on an interior portion of the biopsy needle and revolutions per minute (RPM) of the biopsy needle.

RPM=Feed rate×Pitch of threads

Helical thread 190 as shown in FIGS. 8A-8D may have a pitch of approximately twenty four (24) threads per inch. An optimum pitch may vary based on factors such as reduction gear ratio (77:1 for some embodiments) and load placed on an associated motor.

Further technical benefits may include reducing physical requirements and mental stress on users and decreasing pain and stress on patients by increasing speed and control of the needle set insertion during vertebral procedures or other bone procedures and by decreasing the number of procedures performed and the number of times a bone is drilled into.

For some applications, an IO needle formed in accordance with teachings of the present disclosure may include a hollow cannula or catheter having one end formed by electrical discharge machining (EDM) techniques, grinding techniques and/or other machining techniques. A plurality of teeth may be formed on one end of the cannula or catheter using EDM techniques, grinding techniques and/or other machining techniques.

For some embodiments a stylet or trocar may also be disposed within the cannula or catheter with a first end of the stylet extending from a first end of the cannula or catheter. Increasing the length of the first end of the stylet or trocar extending from the first end of the cannula or catheter may reduce the amount of torque or force required to penetrate a bone and may reduce time required for an associated IO needle set, vertebral needle set, biopsy needle set, aspiration needle set or to penetrate the bone and associated bone marrow.

A specific powered driver, intraosseous device and tip configuration will generally produce the same torque when drilling in a hard bone or a soft bone. However, the time required to drill to a first depth in a hard bone will generally be greater than the time required to drill to similar depth in a soft bone.

For still other embodiments, teeth formed on one end of a cannula or catheter may be bent radially outward to reduce the amount of time and/or force required to penetrate a bone and associated bone marrow using the cannula or catheter. For some applications a powered driver and vertebral needle set, aspiration needle set or biopsy needle set formed in accordance with teachings of the present disclosure may provide access to a patient's bone using a similar amount of torque. The length of time for penetrating a relatively hard bone may be increased as compared with the length of time required to penetrate a relatively softer bone.

The tips of several stylets and cannulas incorporating teachings of the present disclosure were slowly ground with coolant to prevent possible thermal damage to metal alloys or spring material used to form the stylets and cannulas. The stylets and cannulas were assembled into respective IO needle sets. The tips of each needle set were inserted into sawbones blocks under controlled test conditions. Some testing was conducted with Pacific Research sawbones blocks. The tips of the needle sets were inserted to a depth of approximately two centimeters with ten pounds (10 lbs) of force and twelve volts direct current (12 VDC) applied to an associated powered driver. There was no measurable or visual wear of the stylet or cannula tips after completion of the testing.

For some embodiments a generally hollow biopsy needle may be substantially continuously rotated at an optimum speed or RPM during insertion into a selected target area to obtain a biopsy specimen. The biopsy needle may include a longitudinal bore extending from a first, open end of the needle to a second, open end of the needle. A small helical thread may be formed on interior portions of the longitudinal bore proximate the first end. For some embodiments the thread may have a pitch similar to threads used on conventional wood screws. The rate of rotation or revolutions per minute (RPM) of the biopsy needle may be selected by installing a gear assembly with a desired speed reduction ratio (typically between 60:1 and 80:1) between a motor and an associated drive shaft. For some applications the gear assembly may reduce speed of rotation of an attached motor at a ratio of approximately 66:1 or 77:1.

Figure 7C:
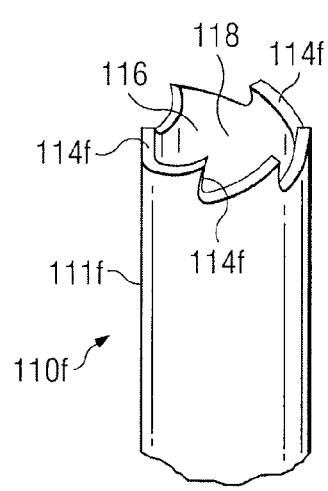
FIG. 7C is a schematic drawing showing an exploded view with portions broken away of the tips of an intraosseous needle set or a cannula incorporating teachings of the present disclosure.

Outer penetrator or cannula 110*f* as shown in FIG. 7C may include first end 111*f* having a plurality of cutting surfaces 114*f* formed adjacent to opening 116 in first end 111*f*. Opening 116 may communicate with and form a portion of an associated longitudinal bore or lumen 118. For some applications cutting surfaces 114*f* may be formed using electrical discharge machining (EDM) techniques. Cannula 110*f* as shown in FIG. 7C may have a cutting surface or tooth 114*f* protruding outward followed by the next cutting surface or tooth 114*f* protruding inward resulting in a cross-cut saw-type pattern. For some medical applications, a cannula such as 110*f* may be used effectively. The pattern of the cutting surfaces may be effective to obtain a biopsy sample since the teeth extending outward may form a passageway (not expressly shown) with an inside diameter larger than a corresponding outside diameter of the cannula. The teeth extending inward may form a sample of bone and/or bone marrow (not expressly shown), having a generally cylindrical configuration with an outside diameter smaller than a corresponding inside diameter of the cannula. The result of such "cross cutting" may be less friction between exterior portions of the cannula and adjacent bone and/or bone marrow and less damage to a biopsy sample disposed within the lumen of the cannula.

Figure 7D:
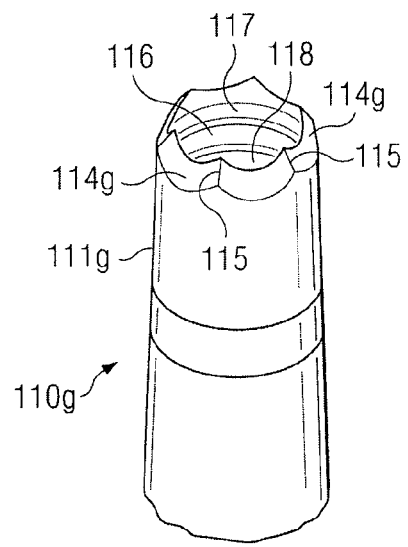
FIG. 7D is a schematic drawing showing an exploded view with portions broken away of the tips of an intraosseous needle set or a cannula incorporating teachings of the present disclosure.

For embodiments such as shown in FIG. 7D, outer penetrator or cannula 110*g* may include first end 111*g* having a generally tapered configuration or reduced outside diameter as compared with other portions of cannula 110*g*. A plurality of cutting surfaces 114*g* may be disposed on end 111*g* adjacent to respective opening 116. For some applications, cutting surfaces 114*g* may be formed using machine grinding techniques. For some embodiments end 111*g* of cannula 110*g* may include six ground cutting surfaces 114*g* with respective crowns 115 may be formed therebetween. Forming a biopsy needle set and/or biopsy needle with tapered end 111*g* and a plurality of cutting surfaces 114*g* and crowns 115 may provide improved drilling performance when the resulting biopsy needle set and/or biopsy needle is used with a powered driver in accordance with teachings of the present disclosure.

For some applications, helical groove 117 may be formed within longitudinal bore 118 proximate respective opening 116. Helical groove 117 may assist with retaining a biopsy specimen or a bone marrow specimen within longitudinal bore 118.

Testing conducted with cannulas or outer penetrators formed in accordance with teachings of the present disclosure indicated that forming cutting surfaces or cutting teeth with electrical discharge machining (EDM) sometimes resulted in the associated cannula or outer penetrator being able to drill through a bone and associated bone marrow slightly faster than a cannula or outer penetrator having cutting surfaces formed using grinding techniques. Some test results also indicated that bending cutting surfaces formed on one end of a cannula or outer penetrator in accordance with teachings of the present disclosure may reduce the amount of time and/or the amount of force required to remove a bone and/or bone marrow specimen from a target area.

Figure 7E:
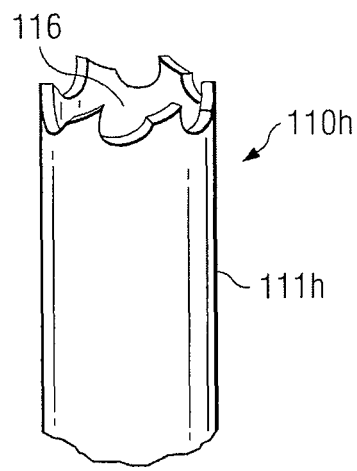
FIG. 7E is a schematic drawing showing an exploded view of one embodiment of the tip of an intraosseous device or cannula incorporating teachings of the present disclosure.
Figure 7F:
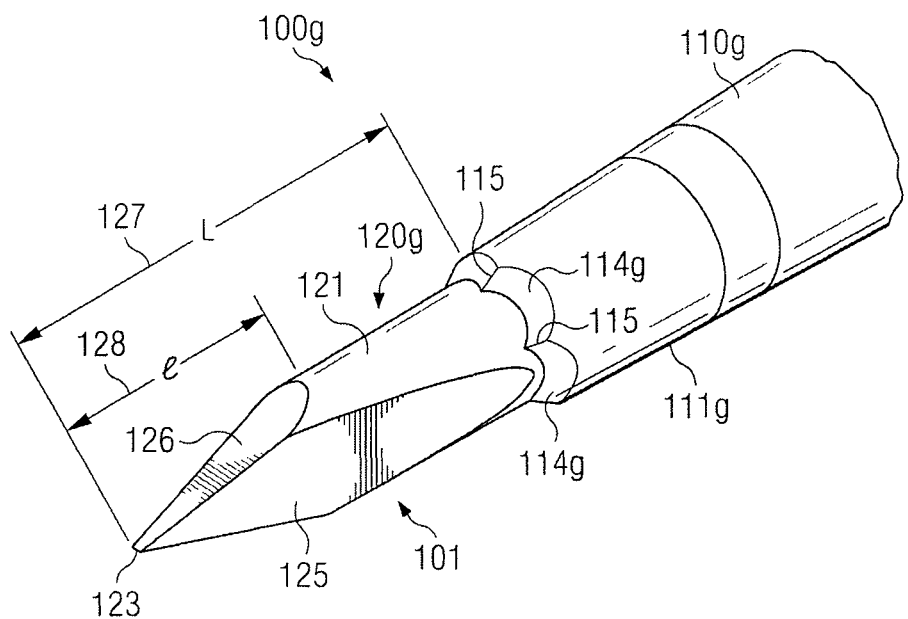
FIG. 7F is a schematic drawing showing an exploded view of still another embodiment of a tip of an intraosseous needle or device incorporating teachings of the present disclosure.

Intraosseous needle set or biopsy needle set 100*g* is shown in FIGS. 7E and 7F. Biopsy needle set 100*g* may include cannula or outer penetrator 110*g* with stylet or inner penetrator 120*g* slidably disposed therein. First end 101 of biopsy needle set 100*g* is shown in FIGS. 7E and 7F. For some applications first end 101 of biopsy needle set 100*g* may minimize damage to skin and soft body tissue at an insertion site.

For some applications inner penetrator or trocar 120*g* may include first end 121 having a plurality of cutting surfaces 125 and 126 formed on exterior portions thereof extending from associated tip 123 towards second end of trocar or inner penetrator 120*g*. For some applications one or more cutting surfaces 125 may be formed having length 127 extending from tip 123 to associated cutting surfaces 114*g* in associated cannula 110*g*. One or more cutting surfaces 126 may be formed adjacent to each cutting surface 125 with second length 128. First length 127 may be greater than second length 128. The ratio of first length 127 and second length 128 may be varied in accordance with teachings of the present disclosure to provide optimum performance for penetrating a selected bone and associated bone marrow.

For some applications, a single thread may be disposed within the longitudinal bore or lumen of a biopsy needle, cannula, catheter or outer penetrator in accordance with teachings of the present disclosure. Various techniques and procedures may be satisfactorily used to place the single thread within a generally hollow cannula or outer penetrator proximate one end of the cannula or outer penetrator having one end operable to penetrate a bone and/or associated bone marrow. For some embodiments, a helical coil having a configuration and dimensions associated with the resulting single thread may be placed on one end of a mandrel such as a spot welding electrode assembly. The mandrel or electrode assembly may then be inserted through an opening in the one end of the cannula or outer penetrator operable to penetrate a bone and/or associated bone marrow. The helical coil may then be bonded with adjacent portions of cannula. Coils having a wide variety of dimensions and configurations may be satisfactorily used to place a single thread in a biopsy needle.

Figure 8A:
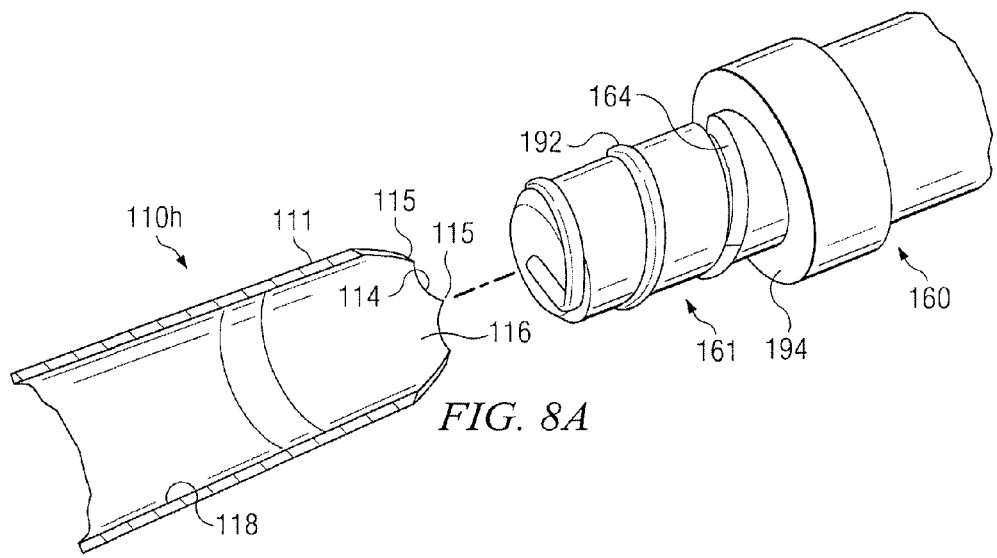
FIG. 8A is a schematic drawing partially in section and partially in elevation with portions broken away showing an exploded isometric view of a mandrel operable to install a thread insert within portions of an intraosseous biopsy needle in accordance with teachings of the present disclosure.

For embodiments such as shown in FIGS. 8A-8E, examples of helical threads are shown disposed in biopsy needles or cannulas incorporating teachings of the present disclosure. Outer penetrator or cannula 110*h* as shown in FIG. 8A may be formed with longitudinal bore 118 or lumen 118 extending from open 116 through cannula 110*h*. Electrode assembly or mandrel 160 may be used to install (spot weld) a single helical thread in lumen 118 proximate opening 116.

Figure 8B:
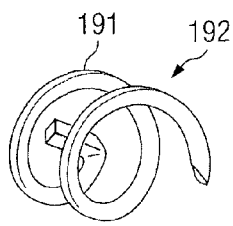
FIG. 8B is a schematic drawing showing one example of a thread insert which may be disposed within the longitudinal bore of an intraosseous biopsy needle in accordance with teachings of the present disclosure.

Helical coil 192 as shown in FIG. 8B may be placed on first end 161 of electrode assembly 160. Helical coil 192 may have the cross section of a right triangle. First end or copper electrode 161 may have an appropriate configuration and dimensions to be slidably received within opening 116 formed in first end 111 of cannula or outer penetrator 110*h*. First end or copper electrode 161 of mandrel 160 may include corresponding groove 164 with a configuration and dimensions satisfactory to receive helical coil 192 therein. Groove 164 may be formed with a desired pitch for resulting thread 190 when attached to or bonded with interior portions of cannula 110*h*.

For some applications electrode assembly 160 may include enlarged outside diameter portion or plastic insulator 194 disposed adjacent to first end 161. The dimensions and/or configuration of copper electrode 161 and plastic insulator 194 may be selected to accommodate installing helical coil 192 at an optimum location relative to end 116 for retaining biopsy specimens in lumen 118. For example, the dimensions and configuration of plastic insulator 194 may be selected to contact the extreme end of outer penetrator or cannula 110*h* proximate crowns 115.

Copper electrode 161 of electrode assembly 160 with helical coil 192 attached thereto may be inserted into opening 116 in first end 111*h* of cannula 110*h*. Electrode assembly 160 may be operable to conduct electricity to copper electrode 161 to accommodate spot welding helical coil 192 with adjacent interior portions of longitudinal bore 118 of cannula 110*h*. For some embodiments mandrel 160 may be formed from materials compatible with laser welding helical coil 192 with interior portions of lumen or longitudinal bore 118 of cannula 110*h*. When attached to interior portions of a cannula or outer penetrator 110*h*, helical coil 192 may form a single thread having shoulder 191 extending generally perpendicular to adjacent interior portions of lumen 118. The resulting dimensions and configuration of helical thread 190 may be selected to optimize retaining a specimen of bone and/or bone marrow on shoulder 191 of thread 190 within lumen 118.

Figure 8C:
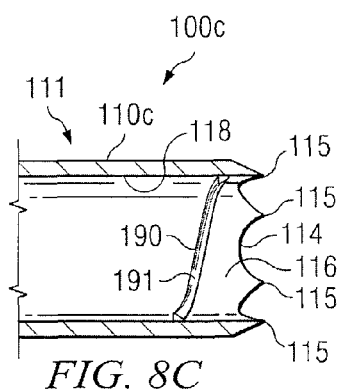
FIG. 8C is a schematic drawing in section with portions broken away showing one example of an intraosseous biopsy needle with a single helical thread disposed within one end of the biopsy needle incorporating teachings of the present disclosure.

Cannula 110c of biopsy needle 100c is shown in FIG. 8C with helical thread 190 disposed therein. The combination of helical thread 190 with shoulder 191 extending substantially perpendicular to interior portions of lumen 118 may increase the reliability of biopsy needle 100c to retain a specimen of bone and/or bone marrow. For some applications combining helical thread 190 with cutting surfaces 114 and crowns 115 may substantially increase the reliability of obtaining a satisfactory bone specimen when using biopsy needle 100c with a powered driver in accordance with teachings of the present disclosure.

Helical thread 190 may be positioned at an optimum location relative to opening 116 in cannula 110c to begin capture of a bone marrow specimen or cancellous bone core. By inserting biopsy needle 100c at an optimum feed corresponding with the pitch of helical thread 190, helical thread 190 may be "screwed in" cancellous bone entering opening 116 to substantially increase the probability of capturing a satisfactory biopsy specimen or bone marrow core.

Figure 8D:
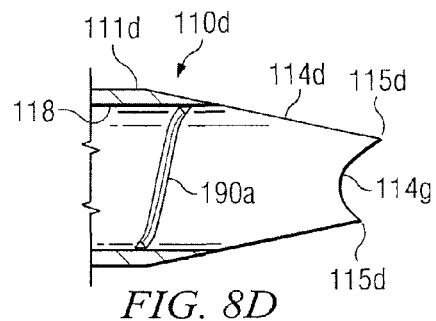
FIG. 8D is a schematic drawing in section with portions broken away showing another example of an intraosseous biopsy needle with a single helical thread disposed within one end of the biopsy needle in accordance with teachings of the present disclosure.

For embodiments such as shown in FIG. 8D cannula or outer penetrator 110d may include first end 111d having a plurality of exterior cutting surfaces 114d formed thereon and extending therefrom. The length of cutting surfaces 114d may be longer than the length of corresponding cutting surfaces 114. Respective crowns 115d may be formed between adjacent cutting surfaces 114d and 114g.

For some applications a helical thread having a generally "wedge shaped" cross section similar to an equilateral triangle may be disposed within the longitudinal bore or lumen of an outer penetrator or cannula incorporating teachings of the present disclosure. For example cannula 110d may include helical thread 190a having a generally wedge shaped cross section corresponding approximately with an equilateral triangle. Helical thread 190a may be installed within cannula 110d using apparatus and procedures as previously described with respect to helical thread 190.

Figure 8E:
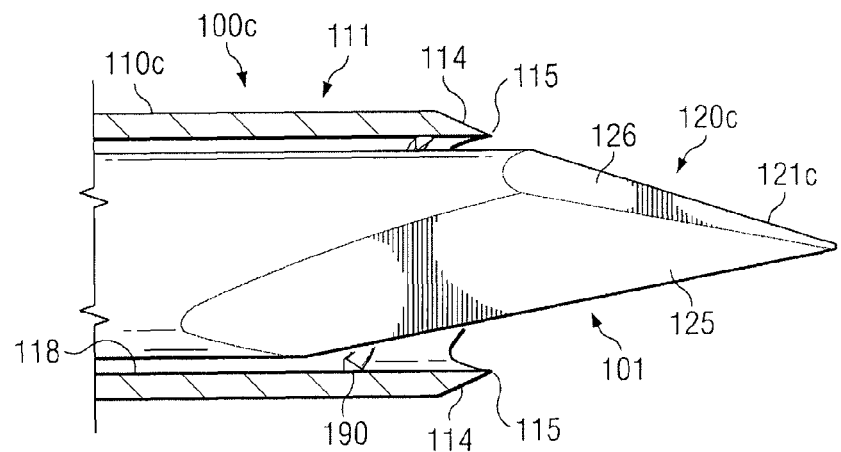
FIG. 8E is a schematic drawing in section and in elevation with portions broken away showing an intraosseous biopsy needle set including a trocar and a single helical thread disposed proximate one end of a generally hollow cannula in accordance with teachings of the present disclosure.

FIG. 8E shows an example of combining inner penetrator or stylet 120c with cannula or outer penetrator 110c having helical thread 190 disposed therein to form biopsy needle set 100c in accordance with teachings of the present disclosure. Biopsy needle 100c is shown in FIGS. 6B and 8C without a stylet or trocar. Biopsy needle set 100c is shown in FIG. 8E with trocar or stylet 120c disposed in cannula 110c. Trocar 120c may include end 121c with a pair of cutting surfaces 125 and a pair of cutting surface 126 as shown in FIG. 7F. Surfaces 125 and 126 may cooperate with each other to form a cutting tip on trocar or stylet 120c similar to a "chisel point" drill bit. The pair of cutting surfaces 125 may be offset (relief angle) approximately eight degrees relative to the pair of cutting surfaces 126. The included angle of cutting surfaces 125 may be approximately thirty four degrees (34°) plus or minus four degrees (±4°). The included angle of cutting surfaces 126 may be approximately sixteen degrees (16°) plus or minus three degrees (±3°).

For some applications end 121 of trocar 120c may extend from end 111c of cannula 110c with respective cutting surfaces 114 of cannula 110g disposed adjacent to the end of each cutting surface 126 (short cutting surface) opposite from tip 123 of trocar 120c. See FIG. 8E. As a result portions of each cutting surface 125 (long cutting surface) of trocar 120c may be disposed within end 111 of cannula 110c. See FIG. 8E.

Placing portions of cutting surfaces 125 within end 111 of cannula 110c may result in more uniform forces being applied to end 101 of intraosseous device 100c while penetrating the cortex of an associated bone using biopsy needle set 100c and a powered driver in accordance with teachings of the present disclosure. When the cortex has been penetrated, forces applied to end 101 of biopsy needle set 100c may decrease sufficiently to indicate that end 101 has now entered associated bone marrow. An operator may then withdraw trocar 120c from cannula 110c and position end 111c of cannula 110c at a desired target area to perform a bone marrow biopsy.

For some embodiments threads 190 and 190a may extend approximately 0.005 inch from adjacent portions of an associated longitudinal bore or lumen 118. The outside diameter of an associated trocar such as trocar 120c as shown in FIG. 8E may be reduced to accommodate the height of thread 190 or 190a. The following test results were obtained during insertion of intraosseous devices such as biopsy needle set 100c shown in FIG. 8E into sawbones material or blocks with three millimeters (3 mm) of fifty pound (50#) and forty millimeters (40 mm) of forty pound (40#) material.

| Test # | Motor Torque(g-cm) | Time(s) |
| --- | --- | --- |
| 44 | 1101 | 2.23 |
| 45 | 1081 | 2.49 |
| 46 | 1071 | 2.36 |
| 47 | 1081 | 2.50 |
| 48 | 1030 | 2.46 |
| 49 | 1070 | 2.33 |
| Average | 1072 | 2.40 |

The distance between the end of cutting surface 126 or trocar 120c and adjacent cutting surface 114 on cannula 110c was approximately 0.14 inches. End 111 of cannula 110c had six (6) ground cutting surfaces 114. The outside diameter of trocar 120c was approximately 0.086 inches.

Coupler assemblies incorporating teachings of the present disclosure may function as "quick release mechanisms" operable to engage and disengage an IO device from a powered driver disposed within a flexible containment bag or sterile sleeve. Such coupler assemblies may allow rotation of an IO device without damage to the flexible containment bag or sterile sleeve. For some applications the IO device may be a vertebral IO needle or a biopsy needle. One end of the coupler assembly may be operable to form a fluid seal or fluid barrier with adjacent portions of the containment bag or sterile sleeve. A coupler assembly incorporating teachings of the present disclosure may be used in "non-sterile" environments and/or medical procedures which do not require the use of a containment bag or sterile sleeve.

Coupler assemblies incorporating various teachings of the present disclosure may be placed in a medical procedure tray or kit with one end down and an opposite end looking up to allow "hands free" releasable engagement with a powered driver or a manual driver. For example, coupler assembly 250 may be disposed in medical procedure tray 20c with first end 251 insert into holders 58 and second end 252 looking up. See FIGS. 1C and 1D. As a result, end 224 of drive shaft 222 extending from powered driver 200 may be inserted into and releasably engaged with second end 252 of coupler assembly 250 without requiring an operator or user (not expressly shown) to physically contact or manipulate any portion of coupler assembly 250. Various features of associated "hands free" latching mechanisms are depicted in FIGS. 5A-5B.

As shown in FIGS. 5A-5D, coupler assembly 250 may include elongated core 260 with housing assembly 270 slidably disposed on exterior portions of elongated core 260.

Housing assembly 270 may include first end 271 and second end 272 which may be generally aligned with respective first end 261 and respective second end 262 of elongated core 260. For some applications, elongated core 260 may have a generally cylindrical configuration defined in first exterior portion 260a and second exterior portion 260b with various shoulders and/or recesses formed thereon. For some embodiments first exterior portion 260a may have a larger diameter than second exterior portion 260b.

Coupler assembly 250a and coupler assembly 250b may include respective elongated cores 260a and 260b having similar features and functions as described with respect to coupler assembly 250. Coupler assembly 250a may include housing assembly 270a with substantially the same components, functions and features as described with respect to housing assembly 270 except for second end 272a of housing assembly 270a. Coupler assembly 250b may include housing assembly 270b having substantially similar components, functions and features as described with respect to housing assembly 270 except for second end 272b of housing assembly 270b.

Housing assembly 270 may be described as having a generally hollow, cylindrical configuration defined in part by first housing segment 280 and second housing segment 290. See FIGS. 5A and 5B. The first end of housing segment 280 may generally correspond with first end 271 of housing assembly 270. The second end of second housing segment 290 may generally correspond with second end 272 of housing assembly 270.

First end 291 of second housing segment 290 may be described as having a generally cylindrical configuration with an outside diameter smaller than the adjacent inside diameter of second end 282 of first housing segment 280. First end 291 of second housing segment 290 may slide longitudinally from a first position to a second position within second end 282 of first housing segment 280 to release one end of a drive shaft engaged with second end 252 of coupler assembly 250 (See FIGS. 5A-5D).

A biasing mechanism such as coiled spring 274 may be disposed around exterior portion 260a of generally elongated core 260. See for example FIGS. 5A, 5B, 5C and 5D. First end 275 of coiled spring 274 may contact annular shoulder 284 formed on interior portions of first housing segment 280. Second end 276 of coiled spring 274 may contact annular shoulder 278 disposed proximate first end 291 of second housing segment 290. Coil spring 274, annular shoulder 284 and annular shoulder 278 may cooperate with each other to generally maintain first housing segment 280 and second housing segment 290 in a first extended position relative to each other. See FIGS. 4A and 5A-5D. Other biasing mechanisms such as, but not limited to, leaf springs and bellows (not expressly shown) may also be disposed between annular shoulder 284 and annular shoulder 278.

Annular shoulder 278, associated with second end 276 of coiled spring 274, may extend radially outward from generally cylindrical ring 277. Generally cylindrical ring 277 may be slidably and rotatably disposed on exterior portion 260a of elongated core 260. Annular shoulder 279 may be disposed on interior portions of generally cylindrical ring 277 and may extend radially inward toward adjacent portions of elongated core 260.

Annular shoulder 268 may be formed on exterior portion 260a of elongated core 260 intermediate first end 261 and second end 262. The configuration and dimensions of annular shoulder 268 and annular shoulder 279 are selected to be compatible with each other such that engagement between annular shoulder 279 of generally cylindrical ring 277 with annular shoulder 268 of elongated core 260 may limit movement of second housing segment 290 longitudinally in the direction of second end 262 of elongated core 260.

For some applications a plurality of flexible collets or fingers 477 may extend from generally cylindrical ring 277 opposite from annular shoulder 278. Respective collet heads 478 may be formed on the end of each collet 477 opposite from annular shoulder 278. The dimensions and configuration of collet heads 478 may be selected to be received within respective slots or openings 297 formed in second housing 290. During manufacture of coupler assembly 250, each collet head 478 may be disposed within respective slot or opening 297 to securely engage generally cylindrical ring 277 and annular shoulder 278 proximate first end 291 of second housing segment 290. As a result, second housing segment 290 and annular shoulder 278 may generally move as a single unit relative to elongated core 260 and first housing segment 280.

During disengagement of an intraosseous device from first end 251 of coupler assembly 250, first housing segment 280 may move or slide longitudinally toward second housing segment 290. In a similar manner, second housing segment 290 may move or slide longitudinally toward first housing segment 280 during disengagement of a powered driver from second end 252 of coupler assembly 250.

Annular shoulder 267 may be formed on exterior portions of elongated core 260 proximate first end 261. Annular shoulder 267 may engage portions of first end 271 of housing 270 to limit longitudinal movement of first housing segment 280 during longitudinal movement of second housing segment 290 towards first end 261 of elongated core 260 during disengagement of a powered driver from second end 252 of coupler assembly 250.

As previously noted, annular shoulder 268 may be formed on exterior portions of elongated core 260 between first end 261 and second end 262. Engagement between annular shoulder 268 and annular shoulder 279 of generally cylindrical ring 277 may limit movement of second housing segment 290 toward second end 262 of elongated core 260. Contact between spring 274 and annular shoulder 278 and annular shoulder 284 of first housing segment 280 may limit the longitudinal movement of first housing segment 280 in the direction of second end 262 of elongated core 260 during disengagement of an intraosseous device from first end 251 of coupler assembly 250.

Generally cylindrical ring 277 and attached annular shoulder 279 may slide longitudinally on exterior portions of annular core 260 between annual shoulder 268 and annular shoulder 267. First housing segment 280 may move longitudinally toward second end 262 of elongated core 260 to release one end of intraosseous device from engagement with first end 251 of coupler assembly 250. In a similar manner, second housing segment 290 may move longitudinally toward first end 261 of elongated core 260 to release one end of a drive shaft extending from a powered driver engaged with second end 252 of coupler assembly 250.

A wide variety of latches and latch mechanisms may be satisfactorily used to releasably engage one end of an intraosseous device within a first end of a coupler assembly incorporating teachings of the present disclosure. In a similar manner, a wide variety of latches and latch mechanisms may be satisfactorily used to releasably engage one end of a drive shaft extending from a powered driver or manual driver within a second end of the coupler assembly incorporating teachings of the present disclosure.

For embodiments represented by coupler assemblies 250, 250a and 250b, first latch 410 may be disposed on exterior portions of elongated core 260 proximate receptacle 263 adjacent to first end 261 to releasably engage one end of an IO device such as second end 102 of an IO needle set 100 within receptacle 263 of coupler assembly 250, 250a and/or 250b. Second latch mechanism 420 may be disposed on exterior portions of elongated core 260 proximate receptacle 264 adjacent to second end 262 to releasably engage one end of a drive shaft with second end 252 of coupler assembly 250. See FIGS. 4A-4C and FIGS. 5A-5D.

Second latch 420 may be used to releasably engage one portion of a drive shaft such as end 224 of drive shaft 222 extending from powered driver 200 within second end 252 of coupler assembly 250, 250a and/or 250b. Latch 410 may releasably engage an intraosseous device with first end 251 of coupler assembly 250 substantially the same latch 420 may releasably engage a powered driver with second end 252 of coupler assembly 250.

Figure 5C:
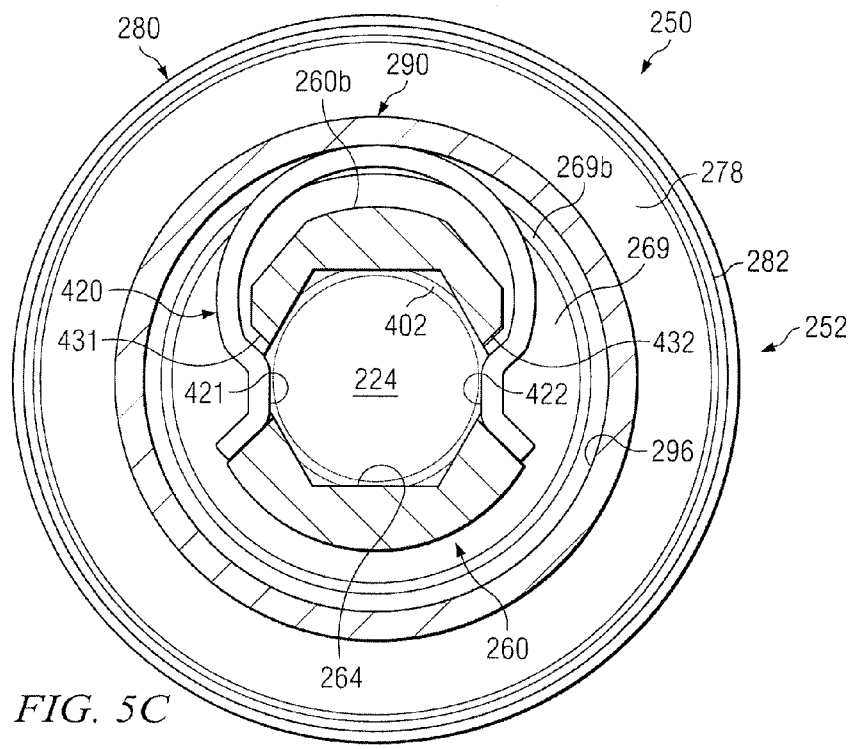
FIG. 5C is a schematic drawing in section taken along lines 5C-5C of FIG. 5B, incorporating teachings of the present disclosure.
Figure 5D:
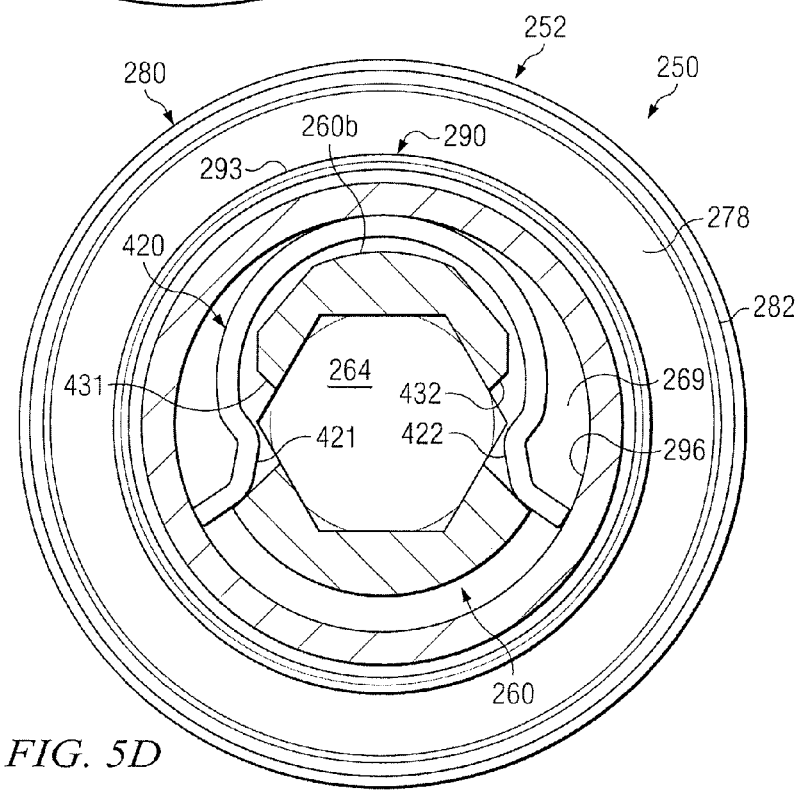
FIG. 5D is a schematic drawing in section taken along lines 5D-5D of FIG. 5A, incorporating teachings of the present disclosure.

For some applications, latches 410 and 420 may have similar configurations such as a general "omega" shape. See latch 420 in FIGS. 5C and 5D. However, latch 410 may have larger dimensions corresponding generally with exterior portion 260a of elongated core 260. Latch 420 may have smaller dimensions corresponding generally with exterior portion 260b of elongated core 260. Various features of the present disclosure may be described with respect to latch mechanism 420 as shown in FIGS. 5C and 5D along with adjacent portions of second housing segment 290 and exterior portion 260b of elongated core 260.

Respective detents 421 and 422 may be formed on opposite ends of generally omega shaped latch 420. See FIGS. 5C and 5D. In a similar manner, respective detents (not expressly shown) may be formed on the ends of generally omega shaped latch 410. The configuration and dimensions of detents 421 and 422 may be compatible with placing each detent 421 and 422 in respective slot or opening 431 and 432 extending between exterior portion 260b of elongated core 260 to interior portions of receptacle 264 disposed proximate second end 252 of coupler assembly 250.

Latch 420 may have a first position such as shown in FIGS. 5A-5D in which portions of detents 421 and 422 may extend through respective slots 431 and 432. The dimensions and configuration of detent 421 and 422 may be operable to be securely engaged with annular groove 402 formed in end 224 of powered driver 200. In a similar manner, respective detents on associated latch 410 may be releasably engaged with annular groove 401 disposed in second end 102 of an IO needle 100.

For some applications, a plurality of tapered surfaces 403 may be formed on exterior portions of hub 140a proximate first end 142 (See FIG. 5A) to radially expand detent mechanisms associated with omega shaped latch 410 radially outward while inserting second end 102 of biopsy needle 100b into first end 251 of coupler assembly 250, 250a or 250b. The detent mechanism may "snap" into annular groove 401 when aligned therewith. In a similar manner, a plurality of tapered surfaces 228 may be formed on exterior portions of end 224 of drive shaft 222 extending from powered driver 200 to radially expand detent mechanisms 421 and 422 radially outward during the insertion of end 224 of powered driver 200 into second end 252 of coupler assembly 250. Detent mechanisms 421 and 422 will "snap" into annular groove 402 when aligned therewith. See FIG. 5A.

Engagement between detent mechanisms associated with latch 410 with annular groove 401 of hub assembly 130a will generally retain second end 102 of biopsy needle 100b securely engaged with first end 251 of coupler assembly 250. This engagement may allow powered driver 200 to rotate or spin cannula or biopsy needle 110 while withdrawing cannula or biopsy needle 110 from an insertion site. In a similar manner, engagement between detent mechanisms 421 and 422 of omega shaped latch 420 and annular groove 402 of end 224 of powered driver 200 will generally retain second end 252 of coupler assembly 250 engaged with powered driver 100 during withdrawal of cannula 110b from an insertion site.

IO needle set 100 may be released from first end 251 of coupler assembly 250 by sliding first housing segment 280 longitudinally toward second end 262 of elongated core 260. Such movement of first housing segment 280 will result in interior tapered surface 286 contacting exterior portions of omega shaped latch 410 and compressing omega shaped latch 410 to radially expand associated detent mechanisms (not expressly shown) from engagement with annular groove 401 of hub assembly 130a. As a result, IO needle set 100 may be easily withdrawn from first end 251 of coupler assembly 250.

In a similar manner, longitudinal movement of second housing segment 290 toward first end 251 of coupler assembly 250 will result in interior tapered surface 296 contacting exterior portions of omega shaped latch 420 to compress generally omega shaped latch 420 and withdraw or retract detent mechanisms 421 and 422 from engagement with annular groove 402 of end 224. See FIG. 5B. As a result, powered driver 200 and second end 252 of coupler assembly 250 may be easily disconnected from each other.

Coupler assemblies 250 and 250a may have substantially the same overall configuration and dimensions including respective flange 254 extending radially from second end 252 and 252a. Flange 254 may be generally described as having an enlarged funnel shaped or bell shaped configuration. The dimensions and configuration of flange 254 may be selected to be compatible with end 211 of powered driver 200. In some embodiments a coupler assembly 250b may not have a respective flange 254 (not expressly shown). Second end 272b of housing assembly 270b may terminate proximate first end 262 of associated elongated core 260 and associated second end 252b of coupler assembly 250b.

Further details about coupler assemblies and other latch mechanisms and release mechanisms may be found in co-pending U.S. patent application Ser. No. 11/853,678, filed on Sep. 11, 2007 entitled "Apparatus And Methods For Biopsy And Aspiration Of Bone Marrow."

Figure 9:
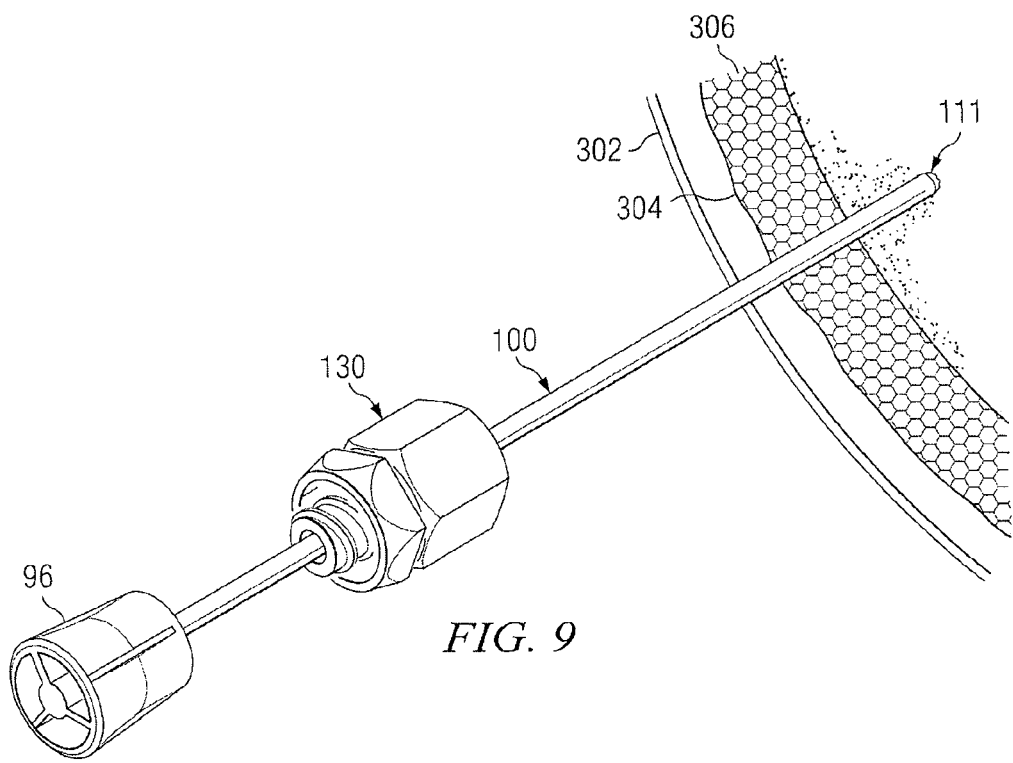
FIG. 9 is a schematic drawing partially in section showing an isometric view of an intraosseous needle set penetrating bone incorporating teachings of the present disclosure.

FIG. 9 depicts an example of apparatus and methods which may be used to insert a first end 111 of the generally hollow cannula or IO needle 100 into the cortex of a bone and/or associated bone marrow. Skin and soft tissue 302 generally cover insertion sites in crest 304 of the bone. All bones generally include a tough, hard to penetrate layer of cortex 306. FIG. 9 shows enlarged skin and soft tissue layer 302 and cortex layer 306 for illustration purposes only. A typical thickness for skin and soft tissue layer 302 may be seven to eight millimeters (7 mm to 8 mm). A typical thickness for cortex layer 306 may be approximately two millimeters (2 mm).

As previously discussed an intraosseous (IO) device or IO needle set 100 may be inserted in the cortex of a bone with minimum trauma to deliver a therapeutic medicament and/or obtain bone and/or bone marrow samples in accordance with teachings of the present disclosure.

The medical devices, medical procedure trays, kits and diagnostic methods and therapeutic methods of the present disclosure may be used to treat or evaluate any bone, such as but not limited to, bones of the vertebrae, neck bones, sternum, rib, clavicle, femoral, pelvic, wrist and the distal ends of the long bones. Some exemplary conditions that may be diagnosed or treated may include fractures, osteoporosis, degenerative bone diseases, bone cancers, metastatic bone disease, osteolytic bone disease, osteomalacia, osteitis fibrosa, Paget's disease, bone deficiency, hyperparathyroidism. Fractures or degeneration of bone may result from osteoporosis which may be age-related osteoporosis, post-menopausal osteoporosis, juvenile osteoporosis, Cushing's syndrome osteoporosis, multiple myeloma osteoporosis, leukemia osteoporosis, Turner's syndrome osteoporosis, alcohol osteoporosis, chronic liver disease osteoporosis, glucocorticoid-induced osteoporosis, chronic inflammatory disease induced osteoporosis and disuse osteoporosis.

FIGS. 10A-10D depict an exemplary medical procedure performed on a vertebral disc of a human patient using the methods, devices, medical procedure trays and kits of the disclosure. In a non-limiting example, the vertebral procedure may be vertebroplasty. The teachings of the present disclosure are however not limited to vertebroplasty or vertebral procedures and medicaments or therapeutic agents of any type may be delivered to a vertebral bone (or any other bone) and/or a biological sample may be obtained for analysis during the same procedure.

In an example vertebroplasty procedure, depicted in FIGS. 10A-10D, an operator may obtain a medical procedures tray 20 comprising a vertebral IO device as set forth in the present disclosure, comprising a vertebral IO needle system/set 100, power driver 200, coupler assembly 250 comprising sterile sleeve 170. An example vertebral IO device may comprise a vertebroplasty needle set and may include a beveled needle comprising a cannula 100a and a stylet with a beveled cutting tip and a serrated cutting edge (see FIGS. 7B and 7F). The IO device may also comprise a biopsy needle set, and may comprise a cannula 100d with a helical thread 192 for capturing a bone sample (see FIGS. 8A and 8B). The coupler assembly 250 may be operable to releasably attach different vertebral IO needles 100 at end 251 and releasably attach power driver 200 at end 252.

The operator may assemble the vertebral system apparatus by unwrapping a sterile medical procedure tray and attaching a non-sterile power driver 200 to end 252 of the coupler assembly 250 and covering power driver 250 with sterile glove 170 as shown in FIGS. 3A and 3B. Sterile vertebral needle 100a may be then attached to end 251 of the coupler 250 as shown in FIG. 3C. The sterile vertebral needle 100a attached to the vertebral apparatus as in FIG. 3C may then be inserted into a vertebral disc "powered in." Generally, an operator trained to perform such a procedure, may insert a vertebral needle 100 through the cortex 306 of a vertebral bone into the vertebral body 307 using powered drill 200 under the guidance of fluoroscopy or other visual imaging methods. Following powering in, driver 200 may be released from the coupler 250 and the stylet comprising a beveled cutting tip and/or a serrated cutting surface and/or any other suitable cutting tip may be withdrawn from the cannula 100 of the vertebral needle, thereby leaving the cannula 100 firmly seated in the vertebral body 307 (see FIG. 10B).

Figure 10A:
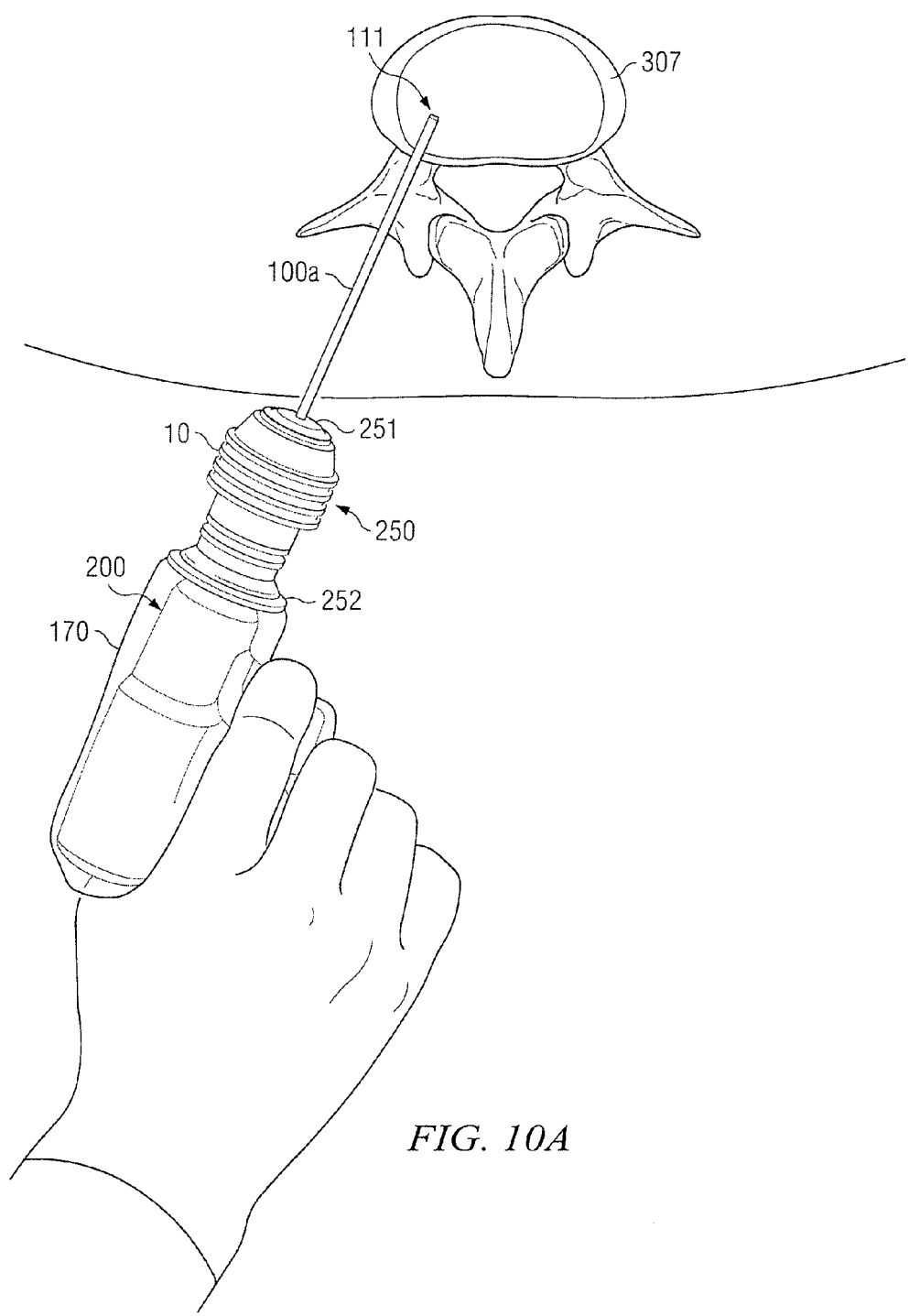
FIG. 10A is a schematic drawing partially in section showing an example of a vertebral procedure using the intraosseous (IO) medical devices and medical procedures tray, wherein a powered driver is used to insert an IO device (needle/cannula) into a vertebral bone, incorporating teachings of the present disclosure.
Figure 10B:
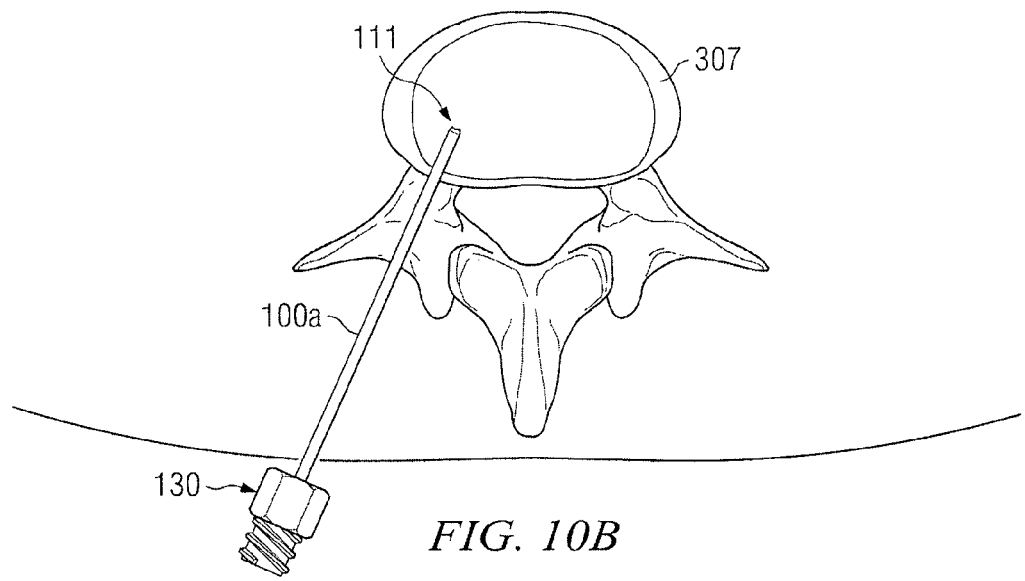
FIG. 10B is a schematic drawing showing partially in section an example of a vertebral procedure using the intraosseous (IO) medical devices and medical procedures tray, wherein the powered device is detached from the intraosseous medical devices leaving the IO needle/cannula attached to the vertebral bone, incorporating teachings of the present disclosure.
Figure 10C:
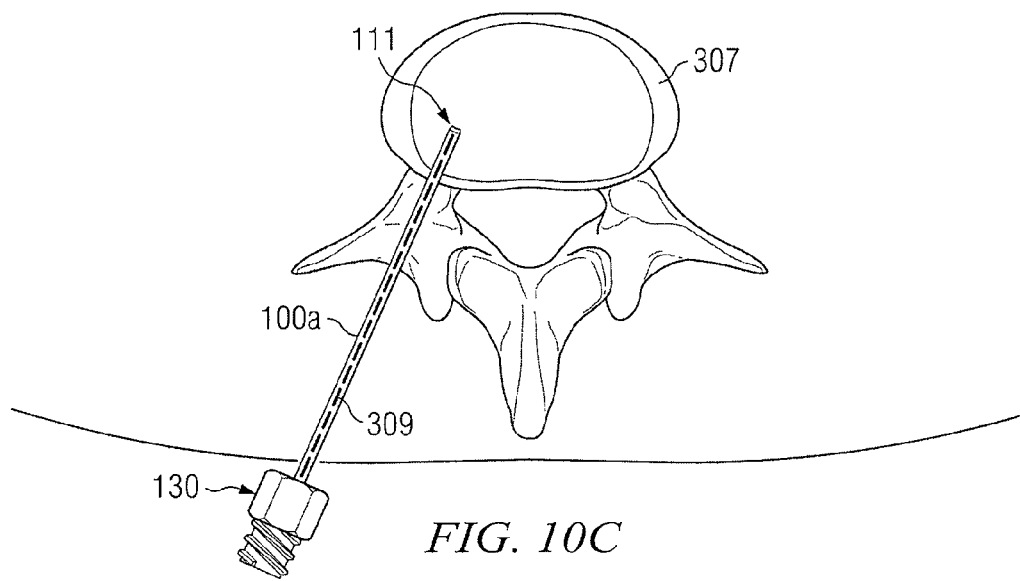
FIG. 10C is a schematic drawing partially in section showing an example of a vertebral procedure using the intraosseous medical devices and medical procedures tray, a therapeutic agent may be delivered into the IO needle/cannula, incorporating teachings of the present disclosure.

A trocar, and/or needle, and/or ejector rod, and/or syringe filled with a bone cement 309 (and/or other medicaments) may be slidably disposed into cannula 100a as shown in FIG. 10C (trocar/needle/rod/syringe 100b not expressly shown) and bone cement 309 may be injected into the vertebral body 307. A connection (such as a Luer lock) may be used to attach 100b with 100a. The trocar 100b may comprise one or more therapeutic agents to be delivered into a bone such as a vertebral disc. For example, a bone strengthening agent/factor may be delivered with the bone cement. In some embodiments, the bone cement or therapeutic agent may be delivered directly through the cannula 100a into the vertebral body (without requiring trocar 100b). The injected bone cement will typically solidify and strengthen a fractured and/or compressed vertebra.

Figure 10D:
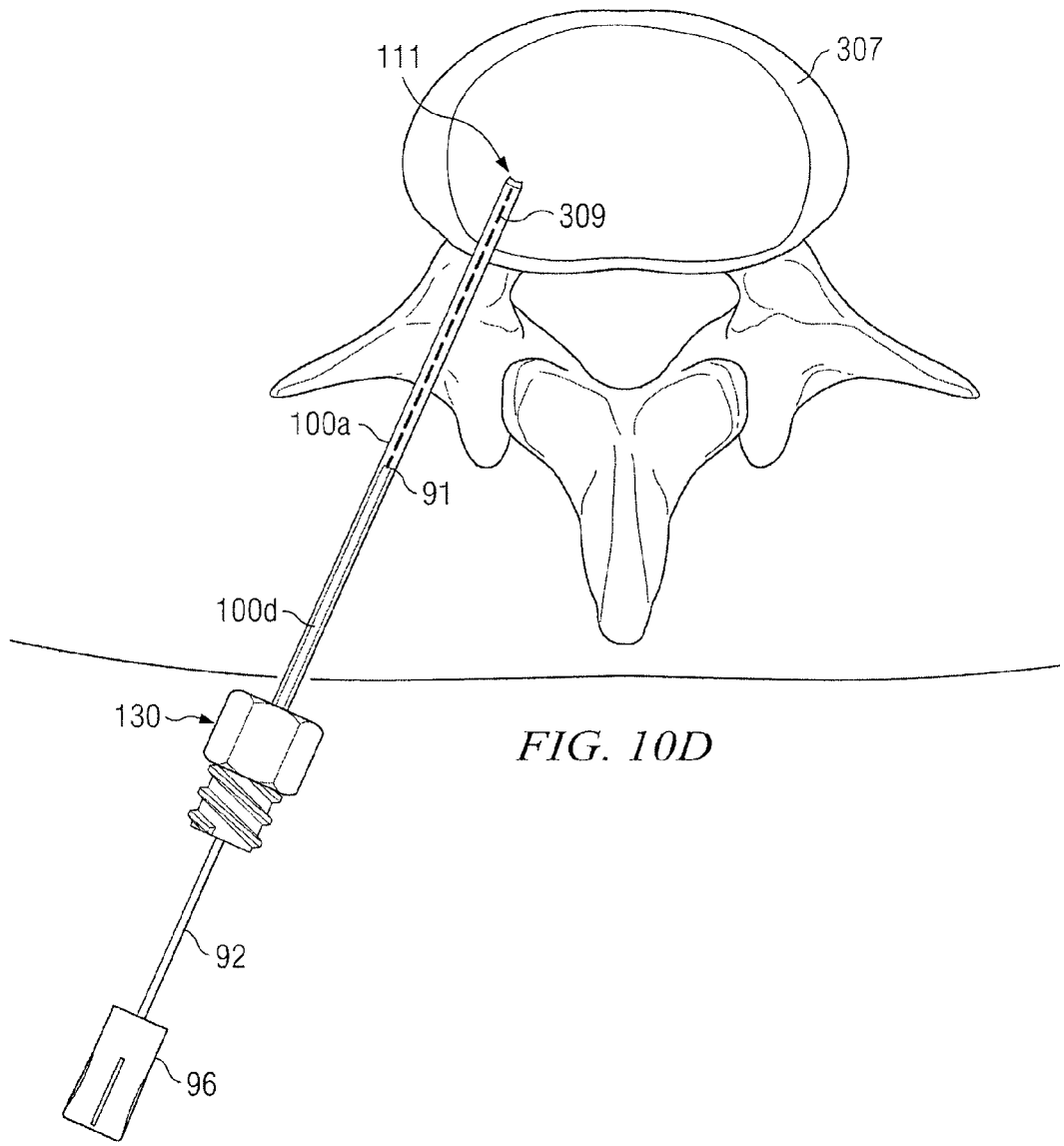
FIG. 10D is a schematic drawing partially in section showing an example of a vertebral procedure using the intraosseous medical devices and medical procedures tray, wherein a trocar (e.g., for delivering a therapeutic agent, or for obtaining a biopsy) is inserted into the cannula attached to a vertebral bone, incorporating teachings of the present disclosure.

Either preceding or following injection of the bone cement 309 into the vertebral body 307, a biopsy needle 100d comprising handle 96, first end 91 and second end 92 may be inserted into cannula 100 and used to obtain a specimen of bone tissue for diagnostic analysis (see FIG. 10D). The biopsy needle 100d may then be withdrawn, power driver 200 reattached to coupler assembly 250 at end 251 and the cannula 100 may be withdrawn from the patient "powered out" (not expressly shown). Thus, a therapeutic procedure may be combined with a diagnostic procedure using the IO needles, IO devices, methods, kits and trays of the present disclosure.

Following the medical and/or diagnostic procedures, the driver 200 may be detached from the coupler assembly and cleaned and stored for further use. A non-sterile power driver 200 maybe used with disposable needles 100 and a disposable coupler 250, comprising a sterile sleeve 170, thereby allowing multiple use of the non-sterile power driver.

As described above, for delivery of a therapeutic agent to bone and/or for removal of a biological specimen from a bone the needles 100b or 100d as depicted in FIGS. 10A-10D may also be referred to as an "ejector rod". An ejector rod, such as 100b or 100d, may be slidably disposed into a hollow cannula 100a of an IO needle to deliver a medicament or obtain a biological sample from a bone.

The length of ejector 100b or 100d may be selected to be greater than the length of a lumen in an associated IO needle 100a. Handle or hub 96 may be disposed on second end 92 of ejector 100b or 100d. The dimensions and configuration of first end 91 of ejector rod 100b or 100d may be selected to be compatible with inserting first end 91 through an opening in the first end of an associated IO needle 100a. As set forth above, the teachings of the present disclosure are not limited to vertebroplasty or vertebral procedures and medical procedures for delivery of a therapeutic agent and possibly combining such a therapeutic procedure with a diagnostic procedure are provided by this disclosure for any bone and any bone related condition.

Benefits of the present disclosure may include reducing physical requirements and mental stress on operators and decreasing pain and stress on patients by increasing speed and control of the needle set insertion during vertebral procedures or other bone procedures and by decreasing the number of procedures performed and the number of times a bone is drilled into.

Although the present disclosure and its advantages have been described in detail, it should be understood that various changes, substitutions and alternations can be made herein without departing from the spirit and scope of the invention as defined by the following claims.

What is claimed is:
1. A coupler assembly operable to releasably attach a plurality of IO devices and releasably attach a non-sterile powered driver comprising:
 a coupler housing;
 a first end operable to releasably attach the plurality of intraosseous (IO) devices;
 a first latch configured to resist detachment of an IO device from the first end;
 a second end operable to releasably attach the non-sterile powered driver such that the powered driver can rotate the intraosseous device attached to the first end around a rotational axis extending through the first end and the second end;

a second latch configured to resist detachment of the driver from the second end;

a sterile containment bag proximate the second end comprising an opening operable to insert and enclose the non-sterile powered driver to prevent contamination of the IO devices by the non-sterile powered driver;

a tortuous path proximate the second end and proximate the sterile containment bag, wherein the tortuous path prevents contamination of the coupler housing following attachment with the non-sterile driver at the second end; and where at least a portion of the coupler housing is operable to be rotated relative to another portion of the coupler housing and relative to the containment bag around the rotational axis for insertion and securing of the IO device at the first end of the coupler assembly.

2. The coupler assembly of claim 1, wherein the sterile containment bag further comprises:

a flexible stay engaged with portions of the opening;

a first end and a second end of the flexible stay configured to be releasably engaged with respective holders in a medical tray to retain the containment bag in an open position to allow inserting the powered driver therein; and a flap operable to wrap around the flexible stay to enclose the opening.

3. The coupler assembly of claim 1, wherein the containment bag is attached proximate the second end using an attachment means.

4. The coupler assembly of claim 3, wherein the attachment means is a hot glue.

* * * * *